(12) United States Patent
Sello

(10) Patent No.: US 10,106,580 B2
(45) Date of Patent: *Oct. 23, 2018

(54) ENOPEPTINS, USES THEREOF, AND METHODS OF SYNTHESIS THERETO

(71) Applicant: Brown University, Providence, RI (US)

(72) Inventor: Jason K. Sello, Providence, RI (US)

(73) Assignee: Brown University, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/924,667

(22) Filed: Oct. 27, 2015

(65) Prior Publication Data

US 2016/0046674 A1  Feb. 18, 2016

Related U.S. Application Data

(63) Continuation of application No. 14/008,062, filed as application No. PCT/US2012/031443 on Mar. 30, 2012, now Pat. No. 9,193,767.

(60) Provisional application No. 61/477,061, filed on Apr. 19, 2011, provisional application No. 61/469,493, filed on Mar. 30, 2011.

(51) Int. Cl.
| | |
|---|---|
| *A61K 38/08* | (2006.01) |
| *C07K 7/56* | (2006.01) |
| *A61K 38/15* | (2006.01) |
| *A61K 31/407* | (2006.01) |
| *C07D 498/14* | (2006.01) |
| *C07D 498/22* | (2006.01) |
| *A61K 38/12* | (2006.01) |
| *A61K 45/06* | (2006.01) |
| *A61K 38/00* | (2006.01) |

(52) U.S. Cl.
CPC .............. *C07K 7/56* (2013.01); *A61K 31/407* (2013.01); *A61K 38/08* (2013.01); *A61K 38/12* (2013.01); *A61K 38/15* (2013.01); *A61K 45/06* (2013.01); *C07D 498/14* (2013.01); *C07D 498/22* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,270,537 A | 6/1981 | Romaine | |
| 4,492,650 A | 1/1985 | Michel et al. | |
| 4,596,556 A | 6/1986 | Morrow et al. | |
| 4,790,824 A | 12/1988 | Morrow et al. | |
| 4,886,499 A | 12/1989 | Cirelli et al. | |
| 4,940,460 A | 7/1990 | Casey et al. | |
| 4,941,880 A | 7/1990 | Burns | |
| 5,015,235 A | 5/1991 | Crossman | |
| 5,064,413 A | 11/1991 | McKinnon et al. | |
| 5,141,496 A | 8/1992 | Dalto et al. | |
| 5,190,521 A | 3/1993 | Hubbard et al. | |
| 5,312,335 A | 5/1994 | McKinnon et al. | |
| 5,328,483 A | 7/1994 | Jacoby | |
| 5,334,114 A | 8/1994 | Ando et al. | |
| 5,339,163 A | 8/1994 | Homma et al. | |
| 5,383,851 A | 1/1995 | McKinnon et al. | |
| 5,417,662 A | 5/1995 | Hjertman et al. | |
| 5,466,220 A | 11/1995 | Brenneman | |
| 5,480,381 A | 1/1996 | Weston | |
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,599,302 A | 2/1997 | Lilley et al. | |
| 5,649,912 A | 7/1997 | Peterson | |
| 5,704,911 A | 1/1998 | Parsons | |
| 5,893,397 A | 4/1999 | Peterson et al. | |
| 5,993,412 A | 11/1999 | Deily et al. | |
| 7,405,201 B2 | 7/2008 | Hinzen et al. | |
| 9,193,767 B2 * | 11/2015 | Sello | A61K 31/407 |
| 2005/0026973 A1 | 2/2005 | Leclerc et al. | |
| 2005/0107288 A1 * | 5/2005 | Hinzen | C07K 7/06 514/19.1 |
| 2009/0306021 A1 | 12/2009 | Nizet et al. | |

FOREIGN PATENT DOCUMENTS

| | | |
|---|---|---|
| CN | 1280009 A | 1/2001 |
| CN | 102838523 A | 12/2012 |

(Continued)

OTHER PUBLICATIONS

Socha, Aaron M. et al, "Diversity oriented synthesis of cyclic acyldepsipeptides leads to the discovery of a potent antibacterial agent." Bioorg. Med. Chem. (2010) 18 p. 7193-7202.*

(Continued)

*Primary Examiner* — Fred H Reynolds
(74) *Attorney, Agent, or Firm* — Wolf, Greenfield & Sacks, P.C.

(57) ABSTRACT

Provided herein are inventive enopeptin compounds of Formula (I):

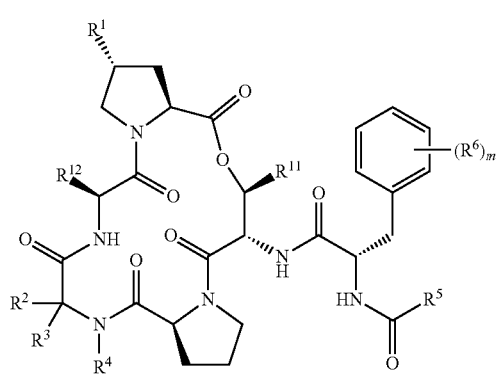

and pharmaceutically acceptable salts thereof, and pharmaceutical compositions thereof. Further provided are methods of preparation, use, and treatment.

23 Claims, 13 Drawing Sheets

(56) References Cited

FOREIGN PATENT DOCUMENTS

| | | |
|---|---|---|
| CN | 103130710 A | 6/2013 |
| CN | 103145608 A | 6/2013 |
| DE | 101 64 147 A1 | 7/2003 |
| DE | 102 19 225 A1 | 11/2003 |
| DE | 103 08 107 A1 | 9/2004 |
| JP | 5065297 B2 | 10/2012 |
| WO | WO 97/06162 A1 | 2/1997 |
| WO | WO 97/13537 A1 | 4/1997 |
| WO | WO 97/37705 A1 | 10/1997 |
| WO | WO 99/34850 A1 | 7/1999 |
| WO | WO 01/55106 A2 | 8/2001 |
| WO | WO 2003/024996 A2 | 3/2003 |
| WO | WO 2012/135615 A2 | 10/2012 |
| WO | WO 2016/037072 A2 | 3/2016 |

OTHER PUBLICATIONS

Extended European Search Report for EP 12764282.5, dated Aug. 5, 2014.

International Search Report and Written Opinion for International Application No. PCT/US/2012/031443, dated Oct. 31, 2012.

International Preliminary Report on Patentability for International Application No. PCT/US/2012/031443, dated Oct. 10, 2013.

[No Author Listed] National Nosocomial Infections Surveillance System. National Nosocomial Infections Surveillance (NNIS) System Report, data summary from Jan. 1992 through Jun. 2004, issued Oct. 2004. Am J Infect Control. Dec. 2004;32(8):470-85.

Alexopoulos et al., ClpP: a structurally dynamic protease regulated by AAA+ proteins. J Struct Biol. Aug. 2012;179(2):202-10. doi: 10.1016/j.jsb.2012.05.003. Epub May 14, 2012.

Baer et al., Phase 3 study of the multidrug resistance modulator PSC-833 in previously untreated patients 60 years of age and older with acute myeloid leukemia: Cancer and Leukemia Group B Study 9720. Blood. Aug. 15, 2002;100(4):1224-32.

Baker et al., ATP-dependent proteases of bacteria: recognition logic and operating principles. Trends Biochem Sci. Dec. 2006;31(12):647-53. Epub Oct. 30, 2006. Review.

Balsano et al., Effect of picotamide on the clinical progression of peripheral vascular disease. A double-blind placebo-controlled study. The ADEP Group. Circulation. May 1993;87(5):1563-9.

Barreiro et al., The methylation effect in medicinal chemistry. Chem Rev. Sep. 14, 2011;111(9):5215-46. doi: 10.1021/cr200060g. Epub Jun. 1, 2011.

Benfield et al., Ligand preorganization may be accompanied by entropic penalties in protein-ligand interactions. Angew Chem Int Ed Engl. Oct. 20, 2006;45(41):6830-5.

Berge et al., Pharmaceutical salts. J Pharm Sci. Jan. 1977; 66(1):1-19.

Bock et al., Getting in shape: controlling peptide bioactivity and bioavailability using conformational constraints. ACS Chem Biol. Mar. 15, 2013;8(3):488-99. doi: 10.1021/cb300515u. Epub Nov. 30, 2012.

Böhm et al., What Can We Learn from Molecular Recognition in Protein—Ligand Complexes for the Design of New Drugs? Angew Chem Int Ed Engl. 1996, 35, 2588-614.

Böttcher et al., Beta-lactones as specific inhibitors of ClpP attenuate the production of extracellular virulence factors of Staphylococcus aureus. J Am Chem Soc. Nov. 5, 2008;130(44):14400-1. doi: 10.1021/ja8051365. Epub Oct. 11, 2008.

Böttcher et al., Beta-lactones decrease the intracellular virulence of Listeria monocytogenes in macrophages. ChemMedChem. Aug. 2009;4(8):1260-3. doi: 10.1002/cmdc.200900157.

Böttcher et al., Structurally refined beta-lactones as potent inhibitors of devastating bacterial virulence factors. Chembiochem. Mar. 2, 2009;10(4):663-6. doi: 10.1002/cbic.200800743.

Boucher et al., Bad bugs, no drugs: no ESKAPE! An update from the Infectious Diseases Society of America. Clin Infect Dis. Jan. 1, 2009;48(1):1-12. doi: 10.1086/595011. Review.

Brötz-Oesterhelt et al., Dysregulation of bacterial proteolytic machinery by a new class of antibiotics. Nat Med. Oct. 2005;11(10):1082-7. Epub Oct. 2, 2005. Erratum in: Nat Med. Dec. 2005;11(12):1361.

Burton et al., Effects of protein stability and structure on substrate processing by the ClpXP unfolding and degradation machine. EMBO J. Jun. 15, 2001;20(12):3092-100.

Carney et al., Investigation of the configurational stabilities of chiral isocyanoacetates in multicomponent reactions. J Org Chem. Dec. 16, 2011;76(24):10279-85. doi: 10.1021/jo201817k. Epub Nov. 10, 2011.

Carney et al., Restriction of the conformational dynamics of the cyclic acyldepsipeptide antibiotics improves their antibacterial activity. J Am Chem Soc. Feb. 5, 2014;136(5):1922-9. doi: 10.1021/ja410385c. Epub Jan. 24, 2014.

Clardy et al., New antibiotics from bacterial natural products. Nat Biotechnol. Dec. 2006;24(12):1541-50. Review.

Compton et al., Antibacterial activity of and resistance to small molecule inhibitors of the ClpP peptidase. ACS Chem Biol. Dec. 20, 2013;8(12):2669-77. doi: 10.1021/cb400577b. Epub Oct. 4, 2013.

Conlon et al., Activated ClpP kills persisters and eradicates a chronic biofilm infection. Nature. Nov. 21, 2013;503(7476):365-70. doi: 10.1038/nature12790. Epub Nov. 13, 2013.

Daga et al., Rapid microwave-assisted deprotection of N-Cbz and N-Bn derivatives. Tetrahedron Letters. Jul. 2001; 42(31): 5191-94.

Davis et al., Novel cyclic sugar imines: carbohydrate mimics and easily elaborated scaffolds for aza-sugars. Org Lett. Jan. 10, 2002;4(1):103-6.

Dömling et al., Multicomponent Reactions with Isocyanides. Angew Chem Int Ed Engl. Sep. 15, 2000;39(18):3168-3210.

Dömling, Recent developments in isocyanide based multicomponent reactions in applied chemistry. Chem Rev. Jan. 2006;106(1):17-89. Review.

Frees et al., Alternative roles of ClpX and ClpP in Staphylococcus aureus stress tolerance and virulence. Mol Microbiol. Jun. 2003;48(6):1565-78.

Frees et al., Global virulence regulation in Staphylococcus aureus: pinpointing the roles of ClpP and ClpX in the sar/agr regulatory network. Infect Immun. Dec. 2005;73(12):8100-8.

Gaillot et al., The ClpP serine protease is essential for the intracellular parasitism and virulence of Listeria monocytogenes. Mol Microbiol. Mar. 2000;35(6):1286-94.

Giordanetto et al., Macrocyclic drugs and clinical candidates: what can medicinal chemists learn from their properties? J Med Chem. Jan. 23, 2014;57(2):278-95. doi: 10.1021/jm400887j. Epub Sep. 17, 2013.

Gominet et al., Acyl depsipeptide (ADEP) resistance in Streptomyces. Microbiology. Aug. 2011;157(Pt 8):2226-34. doi: 10.1099/mic.0.048454-0. Epub Jun. 2, 2011.

Gottesman et al., Protein quality control: triage by chaperones and proteases. Genes Dev. Apr. 1, 1997;11(7):815-23. Review.

Gottesman, Proteolysis in bacterial regulatory circuits. Annu Rev Cell Dev Biol. 2003;19:565-87. Review.

Gottesman et al., The ClpXP and ClpAP proteases degrade proteins with carboxy-terminal peptide tails added by the SsrA-tagging system. Genes Dev. May 1, 1998;12(9):1338-47.

Han et al., Recent development of peptide coupling reagents in organic synthesis. Tetrahedron. Mar. 2004; 60(11): 2447-67.

Hinzen et al., Medicinal chemistry optimization of acyldepsipeptides of the enopeptin class antibiotics. ChemMedChem. Jul. 2006;1(7):689-93.

Joshi et al., Communication between ClpX and ClpP during substrate processing and degradation. Nat Struct Mol Biol. May 2004;11(5):404-11. Epub Apr. 4, 2004.

Karle et al., Structural characteristics of alpha-helical peptide molecules containing Aib residues. Biochemistry. Jul. 24, 1990;29(29):6747-56. Review.

Kessel et al., Homology in structural organization between E. coli ClpAP protease and the eukaryotic 26 S proteasome. J Mol Biol. Jul. 28, 1995;250(5):587-94.

Khan et al., Lowering the entropic barrier for binding conformationally flexible inhibitors to enzymes. Biochemistry. Dec. 1, 1998;37(48):16839-45.

(56) References Cited

OTHER PUBLICATIONS

Kim et al., Dynamics of substrate denaturation and translocation by the ClpXP degradation machine. Mol Cell. Apr. 2000;5(4):639-48.
Kirstein et al., The antibiotic ADEP reprogrammes ClpP, switching it from a regulated to an uncontrolled protease. EMBO Mol Med. Apr. 2009;1(1):37-49. doi: 10.1002/emmm.200900002.
Kolitz et al., Cancer and Leukemia Group B. P-glycoprotein inhibition using valspodar (PSC-833) does not improve outcomes for patients younger than age 60 years with newly diagnosed acute myeloid leukemia: Cancer and Leukemia Group B study 19808. Blood. Sep. 2, 2010;116(9):1413-21. doi: 10.1182/blood-2009-07-229492. Epub Jun. 3, 2010.
Kwon et al., Effect of heat shock and mutations in ClpL and ClpP on virulence gene expression in Streptococcus pneumoniae. Infect Immun. Jul. 2003;71(7):3757-65.
Kwon et al., The ClpP protease of Streptococcus pneumoniae modulates virulence gene expression and protects against fatal pneumococcal challenge. Infect Immun. Oct. 2004;72(10):5646-53.
Laplante et al., Impact of high-inoculum Staphylococcus aureus on the activities of nafcillin, vancomycin, linezolid, and daptomycin, alone and in combination with gentamicin, in an in vitro pharmacodynamic model. Antimicrob Agents Chemother. Dec. 2004;48(12):4665-72.
Lee et al., Control of substrate gating and translocation into ClpP by channel residues and ClpX binding. J Mol Biol. Jun. 25, 2010;399(5):707-18. doi: 10.1016/j.jmb.2010.04.027. Epub Apr. 21, 2010.
Lee et al., Structures of ClpP in complex with acyldepsipeptide antibiotics reveal its activation mechanism. Nat Struct Mol Biol. Apr. 2010;17(4):471-8. doi: 10.1038/nsmb.1787. Epub Mar. 21, 2010.
Leung et al., Activators of cylindrical proteases as antimicrobials: identification and development of small molecule activators of ClpP protease. Chem Biol. Sep. 23, 2011;18(9):1167-78. doi: 10.1016/j.chembiol.2011.07.023.
Leung et al., Methyl effects on protein-ligand binding. J Med Chem. May 10, 2010;55(9):4489-500. doi: 10.1021/jm3003697. Epub Apr. 23, 2012.
Li et al., Acyldepsipeptide antibiotics induce the formation of a structured axial channel in ClpP: A model for the ClpX/ClpA-bound state of ClpP. Chem Biol. Sep. 24, 2010;17(9):959-69. doi: 10.1016/j.chembiol.2010.07.008.
Liang et al., Syntheses, structures and antibiotic activities of LpxC inhibitors based on the diacetylene scaffold. Bioorg Med Chem. Jan. 15, 2011;19(2):852-60. doi: 10.1016/j.bmc.2010.12.017. Epub Dec. 9, 2010.
Lowe, Bacteria: Respect Must Be Paid. In the Pipeline Blog. Mar. 11, 2009. http://blogs.sciencemag.org/pipeline/archives/2009/03/11/bacteria_respect_must_be_paid.
Marsault et al., Macrocycles are great cycles: applications, opportunities, and challenges of synthetic macrocycles in drug discovery. J Med Chem. Apr. 14, 2011;54(7):1961-2004. doi: 10.1021/jm1012374. Epub Mar. 7, 2011.
Marshall et al., Factors governing helical preference of peptides containing multiple alpha,alpha-dialkyl amino acids. Proc Natl Acad Sci U S A. Jan. 1990;87(1):487-91.
Martin et al., Distinct static and dynamic interactions control ATPase-peptidase communication in a AAA+ protease. Mol Cell. Jul. 6, 2007;27(1):41-52.
Martin et al., Rebuilt AAA+ motors reveal operating principles for ATP-fuelled machines. Nature. Oct. 20, 2005;437(7062):1115-20.
Maurizi et al., Endopeptidase Clp: ATP-dependent Clp protease from Escherichia coli. Methods Enzymol. 1994;244:314-31.
Maurizi et al., Molecular properties of ClpAP protease of Escherichia coli: ATP-dependent association of ClpA and clpP. Biochemistry. May 26, 1998;37(21):7778-86.
Nathan, Antibiotics at the crossroads. Nature. Oct. 21, 2004;431(7011):899-902.
Nenajdenko et al., The Ugi reaction with 2-substituted cyclic imines. Synthesis of substituted proline and homoproline derivatives. Tetrahedron. Jun. 2006; 62(25): 5922-30.
Nutt et al., Four-Component Condensation: a New Versatile Method for the Synthesis of Substituted Prolyl Peptides. J Am Chem Soc. 1982; 104: 5852-3.
Osada et al., A novel depsipeptide antibiotic with anti-bacteriophage activity. J Antibiot (Tokyo). Dec. 1991;44(12):1463-6.
Poehlsgaard et al., The bacterial ribosome as a target for antibiotics. Nat Rev Microbiol. Nov. 2005;3(11):870-81.
Raju et al., Bacterial proteolytic complexes as therapeutic targets. Nat Rev Drug Discov. Oct. 2012;11(10):777-89. doi: 10.1038/nrd3846.
Rezai et al., Conformational flexibility, internal hydrogen bonding, and passive membrane permeability: successful in silico prediction of the relative permeabilities of cyclic peptides. J Am Chem Soc. Nov. 1, 2006;128(43):14073-80.
Rezai et al., Testing the conformational hypothesis of passive membrane permeability using synthetic cyclic peptide diastereomers. J Am Chem Soc. Mar. 1, 2006;128(8):2510-1.
Roberts et al., Proteases in Mycobacterium tuberculosis pathogenesis: potential as drug targets. Future Microbiol. May 2013;8(5):621-31. doi: 10.2217/fmb.13.25.
Robertson et al., Global transcriptional analysis of clpP mutations of type 2 Streptococcus pneumoniae and their effects on physiology and virulence. J Bacteriol. Jul. 2002;184(13):3508-20.
Sass et al., Antibiotic acyldepsipeptides activate ClpP peptidase to degrade the cell division protein FtsZ. Proc Natl Acad Sci U S A. Oct. 18, 2011;108(42):17474-9. doi: 10.1073/pnas.1110385108. Epub Oct. 3, 2011.
Sauer et al., AAA+ proteases: ATP-fueled machines of protein destruction. Annu Rev Biochem. 2011;80:587-612. doi: 10.1146/annurev-biochem-060408-172623.
Schmidt et al., Synthesis of Enopeptin B from Streptomyces sp RK-1051. Angew Chem Int Ed Engl 1997; 36: 1110-12.
Schmitz et al., Crystal structure of Mycobacterium tuberculosis ClpP1P2 suggests a model for peptidase activation by AAA+ partner binding and substrate delivery, Proc. Natl Acad. Sci. USA. Oct. 28, 2014;111(43):E4587-95. doi: 10.1073/pnas.1417120111. Epub Sep. 29, 2014.
Searle et al., The cost of conformational order: entropy changes in molecular associations. J Am Chem Soc. 1992, 114(27): 10690-7.
Simila et al., Applications of the Ugi reaction with ketones. Tetrahedron Lett. 2008;49(29-30):4501-4504.
Singh et al., Unfolding and internalization of proteins by the ATP-dependent proteases ClpXP and ClpAP. Proc Natl Acad Sci U S A. Aug. 1, 2000;97(16):8898-903.
Socha et al., Diversity-oriented synthesis of cyclic acyldepsipeptides leads to the discovery of a potent antibacterial agent. Bioorg Med Chem. Oct. 15, 2010;18(20):7193-202. doi: 10.1016/j.bmc.2010.08.032. Epub Aug. 19, 2010.
Socha et al., New bisanthraquinone antibiotics and semi-synthetic derivatives with potent activity against clinical Staphylococcus aureus and Enterococcus faecium isolates. Bioorg Med Chem. Dec. 15, 2006;14(24):8446-54. Epub Sep. 18, 2006.
Steffel et al., Deuterium exchange as an indicator of hydrogen bond donors and acceptors. J Am Chem Soc. Oct. 31, 2007;129(43):12956-7. Epub Oct. 4, 2007.
Szyk et al., Crystal structure at 1.9A of E. coli ClpP with a peptide covalently bound at the active site. J Struct Biol. Oct. 2006;156(1):165-74. Epub Apr. 21, 2006.
Thompson et al., Processive degradation of proteins by the ATP-dependent Clp protease from Escherichia coli. Requirement for the multiple array of active sites in ClpP but not ATP hydrolysis. J Biol Chem. Jul. 8, 1994;269(27):18209-15.
Udugamasooriya et al., Conformational constraint in protein ligand design and the inconsistency of binding entropy. Biopolymers. Aug. 2008;89(8):653-67. doi: 10.1002/bip.20983.
Veber et al., Molecular properties that influence the oral bioavailability of drug candidates. J Med Chem. Jun. 6, 2002;45(12):2615-23.

(56) References Cited

OTHER PUBLICATIONS

Von Nussbaum et al., Antibacterial natural products in medicinal chemistry—exodus or revival? Angew Chem Int Ed Engl. Aug. 4, 2006;45(31):5072-129. Review.
Waki et al., Efficient preparation of N alpha-formylamino acid tert-butyl esters. J Org Chem. May 27, 1977;42(11):2019-20.
Wang et al., Crystal structure determination of *Escherichia coli* ClpP starting from an EM-derived mask. J Struct Biol. Dec. 15, 1998;124(2-3):151-63.
Wang et al., The structure of ClpP at 2.3 A resolution suggests a model for ATP-dependent proteolysis. Cell. Nov. 14, 1997;91(4):447-56.
Webb et al., Effects of DksA and ClpP protease on sigma S production and virulence in *Salmonella typhimurium*. Mol Microbiol. Oct. 1999;34(1):112-23.
Yonath, Antibiotics targeting ribosomes: resistance, selectivity, synergism and cellular regulation. Annu Rev Biochem. 2005;74:649-79. Review.
Young et al., Solution conformation of enopeptin A, a depsipeptide antibiotic, using 2D NMR and restrained molecular dynamics studies. J Antibiot (Tokyo). Aug. 1994;47(8):922-31.
Yu et al., ClpP: a distinctive family of cylindrical energy-dependent serine proteases. FEBS Lett. Jul. 31, 2007;581(19):3749-57. Epub May 8, 2007. Review.
Zhong et al., Practical and efficient synthesis of N-halo compounds. Tetrahedron Lett. Feb. 14, 2005; 46(7): 1099-101.
Zhu et al., On the Preparation of Enantiomerically Pure Isonitriles from Amino Acid Esters and Peptides. Tetrahedron Lett. Feb. 4, 2009;50(5):577-579.
International Search Report and Written Opinion for PCT/US2015/048568, dated Jun. 15, 2016.
Bachas et al., Structural contributions to multidrug recognition in the multidrug resistance (MDR) gene regulator, BmrR .Proc Natl Acad Sci U S A. Jul. 5, 2011;108(27):11046-51. Doi: 10.1073/pnas.1104850108. Epub Jun. 20, 2011.
Balganesh et al., Efflux pumps of *Mycobacterium tuberculosis* play a significant role in antituberculosis activity of potential drug candidates. Antimicrob Agents Chemother. May 2012;56(5):2643-51. Doi: 10.1128/AAC.06003-11. Epub Feb. 6, 2012.
Borges-Walmsley et al., Structure and function of efflux pumps that confer resistance to drugs. Biochem J. Dec. 1, 2003;376(Pt 2):313-38.
Cariello et al., Comparison of the computer programs DEREK and TOPKAT to predict bacterial mutagenicity. Deductive Estimate of Risk from Existing Knowledge. Toxicity Prediction by Komputer Assisted Technology. Mutagenesis. Jul. 2002;17(4):321-9.
Carney et al., A simple fragment of cyclic acyldepsipeptides is necessary and sufficient for ClpP activation and antibacterial activity. Chembiochem. Oct. 13, 2014;15(15):2216-20. doi: 10.1002/cbic.201402358. Epub Sep. 11, 2014.
Chen et al., Internal duplication and homology with bacterial transport proteins in the mdrl (P-glycoprotein) gene from multidrug-resistant human cells.Cell. Nov. 7, 1986;47(3):381-9.
Cole et al., Deciphering the biology of *Mycobacterium tuberculosis* from the complete genome sequence. Nature. Jun. 11, 1998;393(6685):537-44.
Compton et al., Fragment-based strategy for investigating and suppressing the efflux of bioactive small molecules. ACS Infectious Diseases. Dec. 1, 2014;1(1):53-58.
Congreve et al., Recent developments in fragment-based drug discovery.J Med Chem. Jul. 10, 2008;51(13):3661-80. doi: 10.1021/jm8000373. Epub May 6, 2008.
Edwards et al., Peptides as drugs.QJM. Jan. 1999;92(1):1-4.
Erlanson et al., Fragment-based drug discovery.J Med Chem. Jul. 1, 2004;47(14):3463-82.
Frees et al., Clp chaperones and proteases are central in stress survival, virulence and antibiotic resistance of *Staphylococcus aureus*. Int J Med Microbiol. Mar. 2014;304(2):142-9. doi: 10.1016/j.ijmm.2013.11.009. Epub Dec. 1, 2013.
Georgiev et al., Anti-tyrosinase, antioxidant and antimicrobial activities of hydroxycinnamoylamides. Med Chem Res. 2013;22:4173-82.
Gottesman et al., Biochemistry of multidrug resistance mediated by the multidrug transporter.Annu Rev Biochem. 1993;62:385-427.
Gupta et al., Microarray analysis of efflux pump genes in multidrug-resistant *Mycobacterium tuberculosis* during stress induced by common anti-tuberculous drugs. Microb Drug Resist. Mar. 2010;16(1):21-8. doi: 10.1089/mdr.2009.0054.
Gutmann et al., Understanding polyspecificity of multidrug ABC transporters: closing in on the gaps in ABCB1.Trends Biochem Sci. Jan. 2010;35(1):36-42. doi: 10.1016/j.tibs.2009.07.009. Epub Oct. 12, 2009.
Hajduk et al., A decade of fragment-based drug design: strategic advances and lessons learned.Nat Rev Drug Discov. Mar. 2007;6(3):211-9. Epub Feb. 9, 2007.
Hung et al., Route to three-dimensional fragments using diversity-oriented synthesis. Proc Natl Acad Sci U S A. Apr. 26, 2011;108(17):6799-804. doi: 10.1073/pnas.1015271108. Epub Apr. 11, 2011.
Kenniston et al., Partitioning between unfolding and release of native domains during ClpXP degradation determines substrate selectivity and partial processing. Proc Natl Acad Sci U S A. Feb. 1, 2005;102(5):1390-5. Epub Jan. 25, 2005.
Kim et al., Apolipoprotein E polymorphism and clinical course in childhood nephrotic syndrome.Pediatr Nephrol. Mar. 2003;18(3):230-3. Epub Feb. 13, 2003.
Koshino et al., The structure of enopeptins A and B, novel depsipeptide antibiotics. Tetra Lett. 1991;32(52):7707-10.
Lavis et al., Bright ideas for chemical biology.ACS Chem Biol. Mar. 20, 2008;3(3):142-55. doi: 10.1021/cb700248m.
Lee et al., Spectinamides: a new class of semisynthetic antituberculosis agents that overcome native drug efflux.Nat Med. Feb. 2014;20(2):152-8. doi: 10.1038/nm.3458. Epub Jan. 26, 2014.
Loffet, Peptides as drugs: is there a market? J Pept Sci. Jan. 2002;8(1):1-7.
Lomovskaya et al., Identification and characterization of inhibitors of multidrug resistance efflux pumps in Pseudomonas aeruginosa: novel agents for combination therapy. Antimicrob Agents Chemother. Jan. 2001;45(1):105-16.
Lomovskaya et al., Practical applications and feasibility of efflux pump inhibitors in the clinic—a vision for applied use. Biochem Pharmacol. Mar. 30, 2006;71(7):910-8. Epub Jan. 19, 2006.
Lomovskaya et al.,Waltzing transporters and 'the dance macabre' between humans and bacteria. Nat Rev Drug Discov. Jan. 2007;6(1):56-65. Epub Dec. 8, 2006.
Lynch, Efflux systems in bacterial pathogens: an opportunity for therapeutic intervention? An industry view.Biochem Pharmacol. Mar. 30, 2006;71(7):949-56. Epub Nov. 14, 2005.
Machado et al., Contribution of efflux to the emergence of isoniazid and multidrug resistance in *Mycobacterium tuberculosis*.PLoS One. 2012;7(4):e34538. doi: 10.1371/journal.pone.0034538. Epub Apr. 6, 2012.
Mahamoud et al., Antibiotic efflux pumps in Gram-negative bacteria: the inhibitor response strategy. J Antimicrob Chemother. Jun. 2007;59(6):1223-9. Epub Jan. 17, 2007.
Marquez, Bacterial efflux systems and efflux pumps inhibitors. Biochimie. Dec. 2005;87(12):1137-47.
McCarthy et al., Fragment-based lead discovery and design. J Chem Inf Model. Mar. 24, 2014;54(3):693-704. doi: 10.1021/ci400731w. Epub Feb. 19, 2014.
Murakami et al., Crystal structures of a multidrug transporter reveal a functionally rotating mechanism. Nature. Sep. 14, 2006;443(7108):173-9. Epub Aug. 16, 2006.
Nakano et al., Loss-of-function mutations in yjbD result in ClpX- and ClpP-independent competence development of Bacillus subtilis. Mol Microbiol. Oct. 2001;42(2):383-94.
Nakashima et al., Structural basis for the inhibition of bacterial multidrug exporters. Nature. Aug. 1, 2013;500(7460):102-6. doi: 10.1038/nature12300. Epub Jun. 30, 2013.

(56) References Cited

OTHER PUBLICATIONS

Nelson et al., Molecular requirements for the inhibition of the tetracycline antiport protein and the effect of potent inhibitors on the growth of tetracycline-resistant bacteria. J Med Chem. Apr. 29, 1994;37(9):1355-61.
Nikaido et al., Broad-specificity efflux pumps and their role in multidrug resistance of Gram-negative bacteria. FEMS Microbiol Rev. Mar. 2012;36(2):340-63. doi: 10.1111/j.1574-6976.2011.00290. x. Epub Jul. 29, 2011.
Nikaido et al., Prevention of drug access to bacterial targets: permeability barriers and active efflux.Science. Apr. 15, 1994;264(5157):382-8.
Okandeji et al., Synthesis and evaluation of inhibitors of bacterial drug efflux pumps of the major facilitator superfamily. Bioorg Med Chem. Dec. 15, 2011;19(24):7679-89. doi: 10.1016/j.bmc.2011.10. 011. Epub Oct. 13, 2011.
Ollinger et al., Validation of the essential ClpP protease in *Mycobacterium tuberculosis* as a novel drug target. J Bacteriol. Feb. 2012;194(3):663-8. doi: 10.1128/JB.06142-11. Epub Nov. 28, 2011.
Pages et al., Mechanisms of drug efflux and strategies to combat them: challenging the efflux pump of Gram-negative bacteria. Biochim Biophys Acta. May 2009;1794(5):826-33. doi: 10.1016/j. bbapap.2008.12.011. Epub Dec. 25, 2008.
Piddock, Multidrug-resistance efflux pumps—not just for resistance. Nat Rev Microbiol. Aug. 2006;4(8):629-36.
Poole et al., Efflux-mediated antimicrobial resistance. J Antimicrob Chemother. Jul. 2005;56(1):20-51. Epub May 24, 2005.
Rachid et al., Characterization of a novel type of oxidative decarboxylase involved in the biosynthesis of the styryl moiety of chondrochloren from an acylated tyrosine. J Biol Chem. Apr. 23, 2010;285(17):12482-9. doi: 10.1074/jbc.M109.079707. Epub Jan. 15, 2010.
Renau et al., Addressing the stability of C-capped dipeptide efflux pump inhibitors that potentiate the activity of levofloxacin in Pseudomonas aeruginosa. Bioorg Med Chem Lett. Mar. 12, 2001;11(5):663-7.
Renau et al., Inhibitors of efflux pumps in Pseudomonas aeruginosa potentiate the activity of the fluoroquinolone antibacterial levofloxacin. J Med Chem. Dec. 2, 1999;42(24):4928-31.
Rix et al., Target profiling of small molecules by chemical proteomics. Nat Chem Biol. Sep. 2009;5(9):616-24. doi: 10.1038/nchembio. 216.
Rostovtsev et al., A stepwise huisgen cycloaddition process: copper (I)-catalyzed regioselective "ligation" of azides and terminal alkynes. Angew. Chem. Int. Ed. 2002, 114, 2708-11.
Rouviex, Clinical implications of multiple drug resistance efflux pumps of pathogenic bacteria. J Antimicrob Chemother. Jun. 2007;59(6):1208-9.
Sassetti et al., Genetic requirements for mycobacterial survival during infection. Proc Natl Acad Sci U S A. Oct. 28, 2003;100(22):12989-94. Epub Oct. 20, 2003.
Scott et al., Fragment-based approaches in drug discovery and chemical biology.Biochemistry. Jun. 26, 2012;51(25):4990-5003. doi: 10.1021/bi3005126. Epub Jun. 14, 2012.
Stavri et al., Bacterial efflux pump inhibitors from natural sources. J Antimicrob Chemother. Jun. 2007;59(6):1247-60. Epub Dec. 4, 2006.
Vecchione et al., Two distinct major facilitator superfamily drug efflux pumps mediate chloramphenicol resistance in Streptomyces coelicolor. Antimicrob Agents Chemother. Nov. 2009;53(11):4673-7. doi: 10.1128/AAC.00853-09. Epub Aug. 17, 2009.
Viveiros et al., Inhibitors of mycobacterial efflux pumps as potential boosters for anti-tubercular drugs.Expert Rev Anti Infect Ther. Sep. 2012;10(9):983-98. doi: 10.1586/eri.12.89.

Vlieghe et al., Synthetic therapeutic peptides: science and market. Drug Discov Today. Jan. 2010;15(1-2):40-56. doi: 10.1016/j.drudis. 2009.10.009. Epub Oct. 30, 2009.
Webber et al., The importance of efflux pumps in bacterial antibiotic resistance.J Antimicrob Chemother. Jan. 2003;51(1):9-11.
Wei et al., Antimicrobial activities of the cinnamoyl amide of amino acid derivatives. Asian Journal of Chemistry. 2012;24(6):2383-88.
Wong et al., Towards understanding promiscuity in multidrug efflux pumps. Trends Biochem Sci. Jan. 2014;39(1):8-16. doi: 10.1016/j. tibs.2013.11.002. Epub Dec. 6, 2013.
Yu et al., AcrB multidrug efflux pump of *Escherichia coli*: composite substrate-binding cavity of exceptional flexibility generates its extremely wide substrate specificity. J Bacteriol. Oct. 2003;185(19):5657-64.
Yu et al., Structural basis of multiple drug-binding capacity of the AcrB multidrug efflux pump. Science. May 9, 2003;300(5621):976-80.
STN-CAS database Registry No. 1391543-99-9. Entered STN-CAS database on Aug. 15, 2012.
STN-CAS database Registry No. 1359856-11-3. Entered STN-CAS database on Mar. 5, 2012.
STN-CAS database Registry No. 1161070-09-2. Entered STN-CAS database on Jul. 8, 2009.
STN-CAS database Registry No. 784127-14-6. Entered STN-CAS database on Nov. 19, 2004.
STN-CAS database Registry No. 1563579-82-7. Entered STN-CAS database on Mar. 7, 2014.
STN-CAS database Registry No. 1369530-72-2. Entered STN-CAS database on Apr. 17, 2012.
STN-CAS database Registry No. 1308967-24-9. Entered STN-CAS database on Jun. 13, 2011.
STN-CAS database Registry No. 1308972-64-6. Entered STN-CAS database on Jun. 13, 2011.
STN-CAS database Registry No. 1308963-60-1. Entered STN-CAS database on Jun. 13, 2011.
STN-CAS database Registry No. 1308954-71-3. Entered STN-CAS database on Jun. 13, 2011.
STN-CAS database Registry No. 1173662-88-8. Entered STN-CAS database on Aug. 9, 2009.
STN-CAS database Registry No. 1173662-41-3. Entered STN-CAS database on Aug. 9, 2009.
STN-CAS database Registry No. 1132678-39-7. Entered STN-CAS database on Apr. 6, 2009.
STN-CAS database Registry No. 1040202-51-4. Entered STN-CAS database on Aug. 11, 2008.
STN-CAS database Registry No. 1038898-26-8. Entered STN-CAS database on Aug. 5, 2008.
STN-CAS database Registry No. 1308980-53-1. Entered STN-CAS database on Jun. 13, 2011.
STN-CAS database Registry No. 1173684-53-1. Entered STN-CAS database on Aug. 9, 2009.
STN-CAS database Registry No. 1173665-66-1. Entered STN-CAS database on Aug. 9, 2009.
STN-CAS database Registry No. 1041405-14-4. Entered STN-CAS database on Aug. 17, 2008.
STN-CAS database Registry No. 1039648-26-4. Entered STN-CAS database on Aug. 8, 2008.
Supporting Information for Hinzen et al., Medicinal chemistry optimization of acyldepsipeptides of the enopeptin class antibiotics. ChemMedChem. Jul. 2006;1(7):689-93.
International Preliminary Report on Patentability for PCT/US2015/ 048568, dated Mar. 16, 2017.

* cited by examiner (a) HCOOH, DCC, NMM, DMAP, DCM, OC to RT, O/N (72% yield); (b) triphosgene (0.35 eq), NMM (2 eq), DCM, -78 to -30C, 3 hrs (95% yield); (c) tert-BuOH, NaOCl, AcOH, MTBE, OC, 30 min, quantitative; (d) NaOMe, MeOH, 2.5 hrs; (e) Compound 2, N-Boc-(S)-Pro, MeOH, 5 days (76% yield, wherein p = 0); (f) LiOH, 1:1 THF:H$_2$O

ENOPEPTINS, USES THEREOF, AND METHODS OF SYNTHESIS THERETO

RELATED APPLICATIONS

The present application is a continuation of and claims priority under 35 U.S.C. § 120 to U.S. Application, U.S. Ser. No. 14/008,062, filed Dec. 9, 2013, now U.S. Pat. No. 9,193,767, which is a national stage filing under 35 U.S.C. § 371 of international PCT application, PCT/US2012/031443, filed Mar. 30, 2012, which claims priority under 35 U.S.C. § 119(e) to U.S. provisional patent applications, U.S. Ser. No. 61/469,493, filed Mar. 30, 2011, and U.S. Ser. No. 61/477,061, filed Apr. 19, 2011, the entire contents of each of which is incorporated herein by reference.

BACKGROUND OF THE INVENTION

Infectious diseases are the third leading cause of death in developed countries and the second leading cause of death worldwide (see, e.g., World Health Organization (WHO) Geneva, World Health Report (2002); Nathan, *Nature* (2004) 431:899). The efficacy of many antibacterial drugs has been compromised by the emergence of drug resistant, pathogenic bacteria (see, e.g., National Nosocomial Infections Surveillance (NNIS) System, *Am. J. Infect. Control* (2004) 32:470). The Infectious Disease Society of America has recently outlined the deadly implications of a growing number of drug-resistant pathogens (see, e.g., Boucher et al., *J. Clin. Infect. Dis.* (2009) 48:1). Methicillin-resistant *Staphylococcus aureus* (MRSA), vancomycin-resistant *Enterococci* (VRE), and penicillin-resistant *Streptococcus epidermis* are especially worrisome in clinical settings. Unfortunately, the prevalence of multidrug-resistant bacteria has made antibiotics of last resort, like vancomycin, the first-line of therapy. The capacity of bacteria to routinely develop resistance to virtually any antibacterial agent necessitates a continuous search for new drugs. There is much evidence in the literature that natural products derived from microorganisms will continue to be a source of novel antibacterial drugs (see, e.g., Clardy, *Nat. Biotechnol.* (2006) 24:1541). Although natural products often have chemical properties that are incompatible with chemotherapy, it is possible to use medicinal chemistry as a means to enhance their biological activity and/or pharmacological properties (see, e.g., von Nussbaum et al., *Angew. Chem. Int. Ed.* (2006) 45:5072).

A recent case where medicinal chemistry was used to improve the activity of a natural product was that of the enopeptins (see, e.g., Hinzen et al., *Chem Med Chem* (2006) 1:689; U.S. 20050107288). The parent compounds were isolated from the soil-dwelling bacterium *Streptomyces* sp. RK-1051 and are defined by a 16-membered peptidolactone consisting of five L-amino acids to which a lipophilic polyene side chain is appended (see, e.g., Osada et al., *J. Antibiot.* (1991) 44:1463). A group of closely related compounds, called A54556 A and B, were isolated from *Streptomyces hawaiienesis* by a research group at Eli Lilly (U.S. Pat. No. 4,492,650). The enopeptins attracted attention because of their potent activity against drug-resistant bacterial pathogens, including MRSA and VRE (see, e.g., Brötz-Oesterhelt et al., *Nat. Med.* (2005) 11:1082). The apparent lack of cross-resistance for all antibacterial agents on the market or those in clinical development has been ascribed to a peculiar mechanism of action. The enopeptin antibiotics inhibit cell division and cause cell death by binding and deregulating the activity of the casein lytic protease (ClpP) (see, e.g., Brötz-Oesterhelt, supra). Under normal conditions, this fourteen-subunit protease selectively degrades proteins through a physical and functional association with accessory ATPases that recognize and unfold its substrates (see, e.g., Maurizi et al., *Biochemistry* (1999) 37:7778; Singh et al., *Proc. Natl. Acad. Sci., USA.* (2000) 97:8898; Baker et al., *Trends Biochem. Sci.* (2006) 31:647; Hsiung et al., *FEBS Lett.* (2007) 581: 3749). In the presence of the enopeptins, ClpP indiscriminately degrades folded cytoplasmic proteins, which ultimately causes cell death (see, e.g., Brötz-Oesterhelt, supra). Recent structural studies indicate that the enopeptins bind the ClpP core structure and cause it to undergo a conformational change that exposes the enzymatic active sites of its subunits (see, e.g., Lee et al., *Nature Structural Biology* (2010) 17:471-479).

Although the enopeptin natural products have remarkable antibacterial activity in vitro, their chemical lability and poor solubility limit their efficacy in vivo (see, e.g., Hinzen et al., *Chem Med Chem* (2006) 1:689). Therefore, this continues to be a need for the development and study of new and improved enopeptin compounds.

SUMMARY OF THE INVENTION

The present invention provides novel enopeptin compounds, pharmaceutical compositions thereof, and methods of preparation, use, and treatment using these compounds.

In one aspect, provided is a compound of Formula (I):

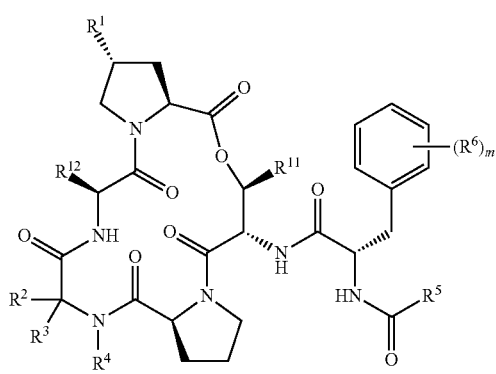

or a pharmaceutically acceptable salt thereof; wherein $R^1$, $R^2$, $R^3$, $R^4$, $R^5$, $R^6$, $R^{11}$, $R^{12}$, and m are as defined herein.

In another aspect, provided is a method of preparing a compound of Formula (I), the method comprising providing a compound of Formula (G):

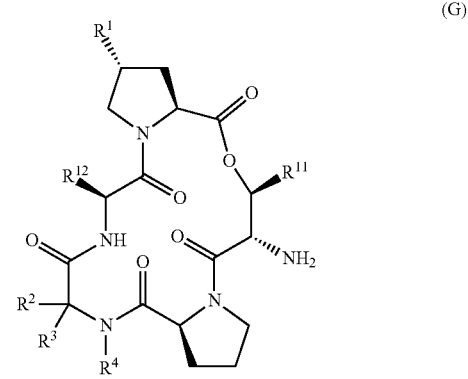

or salt thereof; and coupling the compound of Formula (G), or salt thereof, with a compound of Formula (H)

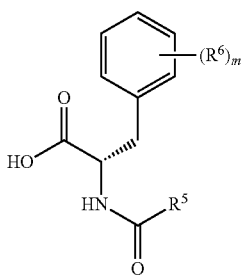

(H)

or salt thereof; to provide a compound of Formula (I), or salt thereof.

In certain embodiments, the compound of Formula (G) is prepared by providing a compound of Formula (E):

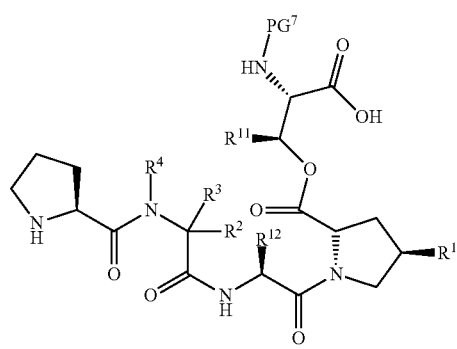

(E)

or salt thereof, wherein $PG^7$ is an amino protecting group; cyclizing the compound of Formula (E), or salt thereof, to provide a compound of Formula (F):

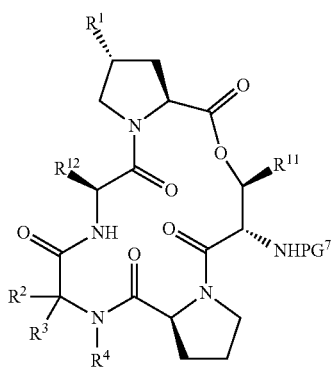

(F)

or salt thereof; and deprotecting the compound of Formula (F), or salt thereof, to provide a compound of Formula (G) or salt thereof.

In certain embodiments, the compound of Formula (E) is prepared by providing a compound of Formula (C):

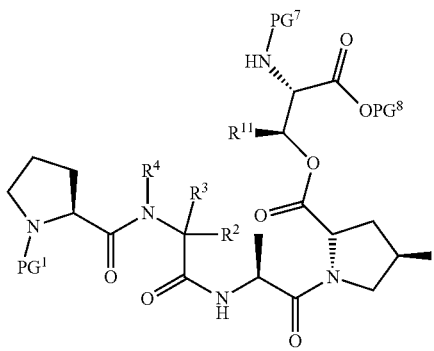

(C)

or salt thereof; wherein $PG^1$ and $PG^7$ are amino protecting groups; and $PG^8$ is an oxygen protecting group; and deprotecting the compound of Formula (C), or salt thereof, to provide a compound of Formula (E) or salt thereof.

In certain embodiments, the compound of Formula (C) is prepared by providing a compound of Formula (A) and a compound of Formula (B):

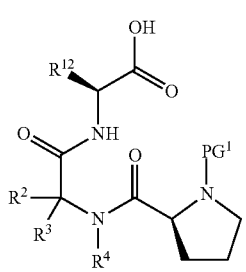

(A)

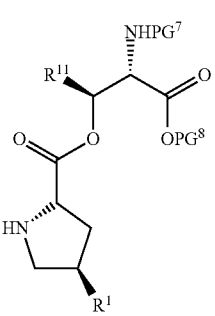

(B)

or salt thereof; and coupling the compound of Formula (A), or salt thereof, with a compound of Formula (B), or salt thereof, to provide a compound of Formula (C), or salt thereof; wherein $PG^1$ and $PG^7$ are amino protecting groups; and $PG^8$ is an oxygen protecting group.

In another aspect, provided is a method of treating a microbial infection in a subject, comprising administering an effective amount of a compound of the present invention, e.g., a compound of Formula (I) or a pharmaceutically acceptable salt thereof, to the subject. In certain embodiments, the microbial infection is a bacterial infection. In certain embodiments, the method further comprises administering the compound in combination with an antibiotic. In certain embodiments, the antibiotic is a ribosome-targeting antibiotic. In certain embodiments, the ribosome-targeting antibiotic is a tetracycline antibiotic.

In another aspect, provided is a method of treating bacterial virulence. Such a method can be conducted in vivo (i.e., by administration to a subject) or in vitro (e.g., upon contact with bacteria in a cell culture). For example, in certain embodiments, provided is a method of treating bacterial virulence comprising administering an effective amount of a compound of the present invention, e.g., a compound of Formula (I) or a pharmaceutically acceptable salt thereof, to a subject with a bacterial infection. In certain embodiments, the compound blocks virulence factor production.

In yet another aspect, provided is a method of treating bacterial infection and/or virulence including the treatment of bacteria or infection caused by bacteria that are resistant to other treatments, are multi-drug tolerant or resistant and/or that neither grow nor die in the presence of or as a result of other treatments. Such a method can be conducted in vivo (i.e., by administration to a subject) or in vitro (e.g., upon contact with bacteria in a cell culture). For example, in certain embodiments, provided is a method of treating bacterial virulence comprising administering an effective amount of a compound of the present invention, e.g., a compound of Formula (I) or a pharmaceutically acceptable salt thereof, to a subject with a bacterial infection. In certain embodiments, the compound blocks virulence factor production.

The details of one or more embodiments of the invention are set forth in the accompanying Figures and the Detailed Description. Other features, objects, and advantages of the invention will be apparent from the description and from the claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N.Y., 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 30 carbon atoms ("$C_{1-30}$ alkyl"). In some embodiments, an alkyl group has 1 to 20 carbon atoms ("$C_{1-20}$ alkyl"). In some embodiments, an alkyl group has 1 to 20 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

"Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-8}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

As used herein, "alkenyl" refers to a radical of a straight-chain or branched hydrocarbon group having from 2 to 30 carbon atoms and one or more carbon-carbon double bonds ("$C_{2-30}$ alkenyl"). In some embodiments, an alkenyl group has 2 to 20 carbon atoms ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "alkynyl" refers to a radical of a straight-chain or branched hydrocarbon group having from 2 to 30 carbon atoms and one or more carbon-carbon triple bonds ("$C_{2-30}$ alkynyl"). In some embodiments, an alkynyl group has 2 to 20 carbon atoms ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "carbocyclyl" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic or tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond.

The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., contains all single bonds.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O) (R$^{aa}$)$_2$, —OP(=O)(R$^{aa}$)$_2$, —OP(=O)(OR$^{cc}$)$_2$, —P(=O)$_2$N (R$^{bb}$)$_2$, —OP(=O)$_2$N(R$^{bb}$)$_2$, —P(=O)(NR$^{bb}$)$_2$, —OP(=O) (NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{cc}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON (R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. The term "substituted amino," by extension, refers to a monosubstituted amino, a disubstituted amino, or a trisubstituted amino, as defined herein.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N (R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$ X$^-$, wherein R$^{bb}$ and X$^-$ are as defined herein.

As used herein, the term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

As used herein, the term "sulfinyl" refers to the group —S(=O)R$^{aa}$, wherein R$^{aa}$ is as defined herein.

As used herein, the term "acyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

As used herein, the term "silyl" refers to the group —Si(R$^{aa}$)$_3$, wherein R$^{aa}$ is as defined herein.

As used herein, the term "boronyl" refers to boranes, boronic acids, boronic esters, borinic acids, and borinic esters, e.g., boronyl groups of Formula —B(R$^{aa}$)$_2$, —B(OR$^{cc}$)$_2$, and —BR$^{aa}$(OR$^{cc}$), wherein R$^{aa}$ and R$^{cc}$ are as defined herein.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F, Cl, Br, I), NO$_3$, ClO$_4$, OH, H$_2$PO$_4$, HSO$_4$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an amino protecting group (also referred to herein as a "nitrogen protecting group"). Amino protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethylbenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is a hydroxyl or thiol protecting group (also respectively referred to herein as an "oxygen protecting group" or "sulfur protecting group"). Hydroxyl and thiol protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Hydroxyl and thiol protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary hydroxyl and thiol protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

These and other exemplary substituents are described in more detail in the Detailed Description, Examples, and claims. The invention is not intended to be limited in any manner by the above exemplary listing of substituents.

Other Definitions

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "salt" refers to any and all salts, including pharmaceutically acceptable salts.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, and unless otherwise specified, the terms "treat," "treating" and "treatment" contemplate an action that occurs while a subject is suffering from the specified infection which reduces the severity of the infection or retards or slows the progression of the infection ("therapeutic treatment"), and also contemplates an action that occurs before a subject begins to suffer from the specified infection and which inhibits or reduces the severity of the infection ("prophylactic treatment").

In general, the "effective amount" of a compound refers to an amount sufficient to elicit the desired biological response, i.e., treating an infection. As will be appreciated by those of ordinary skill in this art, the effective amount of a compound of the invention may vary depending on such factors as the desired biological endpoint, the pharmacokinetics of the compound, the condition being treated, the mode of administration, and the age, health, and condition of the subject. For example, the effective amount of a compound with anti-bacterial activity is the amount that results in a sufficient concentration to inhibit the growth, reduce, or kill bacteria, or make bacteria less virulent. An effective amount encompasses therapeutic and prophylactic treatment.

As used herein, and unless otherwise specified, a "therapeutically effective amount" of a compound is an amount sufficient to provide a therapeutic benefit in the treatment of a infection or to delay or minimize one or more symptoms associated with the infection. A therapeutically effective amount of a compound means an amount of therapeutic agent, alone or in combination with other therapies, which provides a therapeutic benefit in the treatment of the infection. The term "therapeutically effective amount" can encompass an amount that improves overall therapy, reduces or avoids symptoms or causes of infection, or enhances the therapeutic efficacy of another therapeutic agent.

As used herein, and unless otherwise specified, a "prophylactically effective amount" of a compound is an amount sufficient to prevent an infection, or one or more symptoms associated with the infection or prevent its recurrence. A prophylactically effective amount of a compound means an amount of a therapeutic agent, alone or in combination with other agents, which provides a prophylactic benefit in the prevention of the infection. The term "prophylactically effective amount" can encompass an amount that improves overall prophylaxis or enhances the prophylactic efficacy of another prophylactic agent.

As used herein "virulence" refers to the degree of pathogenicity within of a microorganism as indicated by case fatality rates and/or the ability of the organism to invade the issues of the subject; e.g., the ability of the organism to cause an infection. A "reduction of virulence" refers to a reduction of this pathogenic capacity of the organism.

As used herein, use of the phrase "at least one instance" refers to one instance, but also encompasses a range, e.g., for example, from one instance to four instances.

BRIEF DESCRIPTION OF THE DRAWINGS

FIG. 4A: Synthesis of tripeptide fragment using Joullié-Ugi 3CR; FIG. 4B: Coupling of the tripeptide fragment with the ester fragment and ring cyclization; FIG. 4C: Exemplary picolate-derived enopeptin compounds 10a-10d.

FIG. 5A: Synthesis of tripeptide fragment using Ugi 4CR; FIG. 5B: Coupling of the tripeptide fragment with the ester fragment and ring cyclization; FIG. 5C: Exemplary α,α-disubstituted amino acid-derived enopeptin compounds 10e-10h.

FIG. 7A illustrates ADEP1 bound to ClpP; FIG. 7B illustrates ADEP2 bound to ClpP (see Lee et al., *Nature Structural Biology* (2010) 17:471-479).

DETAILED DESCRIPTION OF CERTAIN EMBODIMENTS OF THE INVENTION

Figure 1:
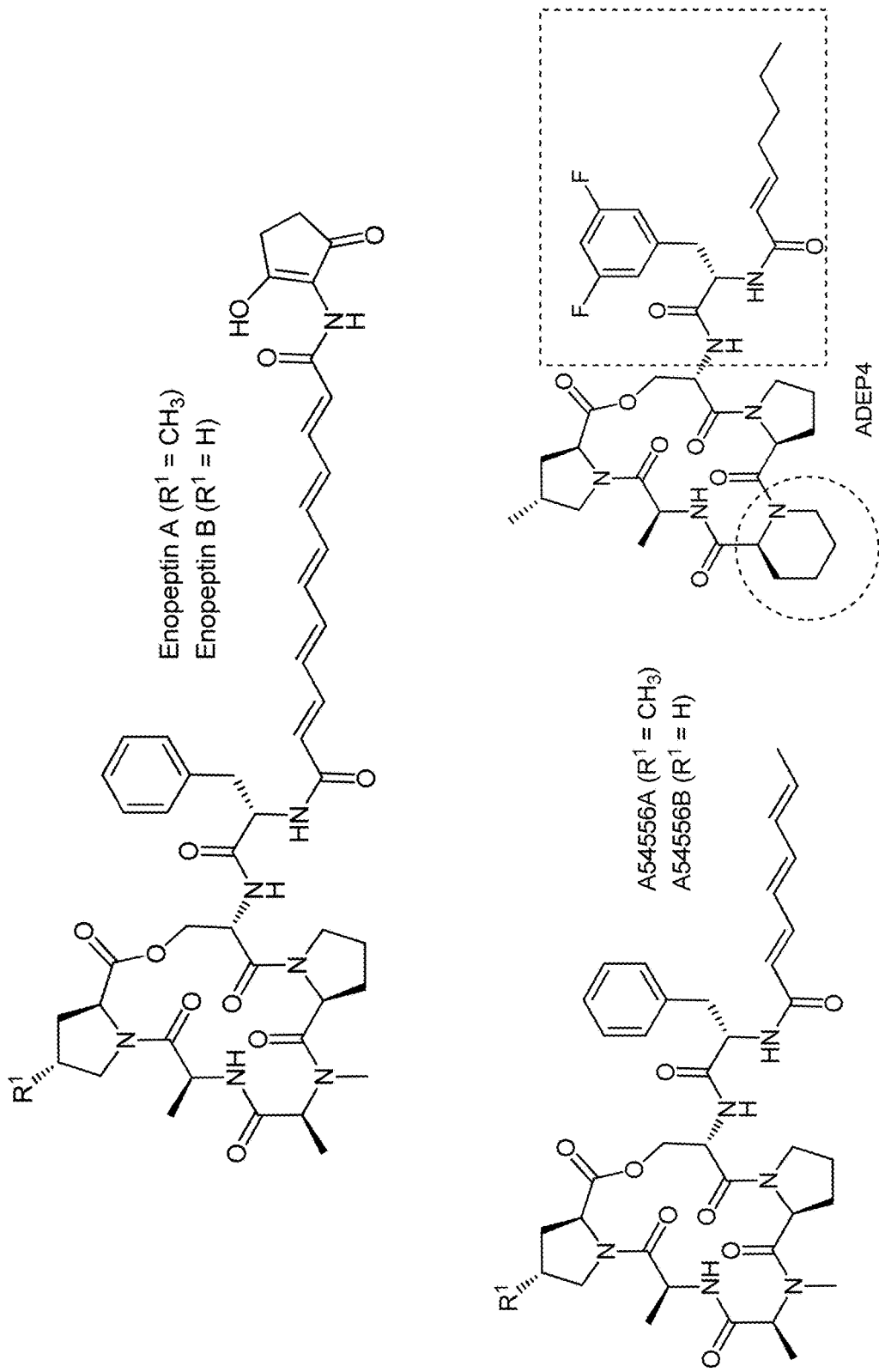
FIG. 1 depicts natural products Enopeptin A and B (*Strepomyces* sp RK-1051), A54556A and B (*Streptomyces hawaiiensis*), and synthetic analog ADEP4.

The present invention provides inventive enopeptin compounds, e.g. a compound of Formula (I):

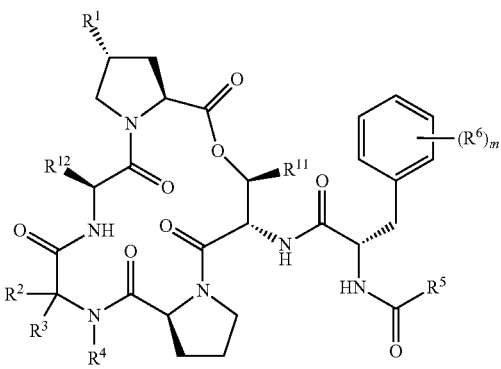

or a pharmaceutically acceptable salt thereof; wherein:

$R^1$ is selected from hydrogen optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^2$ is hydrogen, and $R^3$ and $R^4$ are joined to form an optionally substituted heterocyclyl; or $R^2$ and $R^3$ are joined to form a spiro-fused optionally substituted carbocyclyl or spiro-fused optionally substituted heterocyclyl, and $R^4$ is hydrogen, optionally substituted alkyl, or an amino protecting group; or $R^2$ and $R^3$ are independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided that $R^2$ and $R^3$ are not both hydrogen; and $R^4$ is hydrogen, optionally substituted alkyl, or an amino protecting group;

$R^5$ is —OH, —SH, —NH$_2$, substituted hydroxyl, substituted thiol, substituted amino, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of $R^6$ is independently halogen, —OH, —SH, —NH$_2$, —CN, —NO$_2$, —N$_3$, —SO$_2$H, —SO$_3$H, substituted hydroxyl, substituted thiol, substituted amino, sulfonyl, sulfinyl, acyl, silyl, boronyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

m is 0 or an integer of between 1 and 5, inclusive;

$R^{11}$ is hydrogen, —OH, —SH, —NH$_2$, substituted hydroxyl, substituted thiol, substituted amino, optionally substituted alkyl, optionally substituted alkenyl, optionally substituted alkynyl, optionally substituted carbocyclyl, optionally substituted heterocyclyl, optionally substituted aryl, or optionally substituted heteroaryl; and $R^{12}$ is hydrogen, —OH, —SH, —NH$_2$, substituted hydroxyl, substituted thiol, substituted amino, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, the stereochemistry of the carbon attached to $R^2$ and $R^3$ may be (R) or (S). In certain embodiments, the stereochemistry of the carbon attached to $R^2$ and R³ is (R). In certain embodiments, the stereochemistry of the carbon attached to R² and R³ is (S).

In certain embodiments, R¹ is hydrogen or optionally substituted alkyl. In certain embodiments, R¹ is hydrogen. In certain embodiments, R¹ is optionally substituted alkyl (e.g., —CH₃, —CH₂CH₃).

In certain embodiments, R² is hydrogen, and R³ and R⁴ are joined to form an optionally substituted 5- to 6-membered heterocyclyl.

In certain embodiments, R² is hydrogen, and R³ and R⁴ are joined to form an optionally substituted 5- to 6-membered heterocyclyl, wherein the optionally substituted 5- to 6-membered heterocyclyl contains one or more additional heteroatoms selected from oxygen, nitrogen and sulfur. In certain embodiments, the optionally substituted 5- to 6-membered heterocyclyl contains one additional heteroatom selected from oxygen. In certain embodiments, the optionally substituted 5- to 6-membered heterocyclyl contains one additional heteroatom selected from nitrogen. In certain embodiments, the optionally substituted 5- to 6-membered heterocyclyl contains one additional heteroatom selected from sulfur.

In certain embodiments, R² is hydrogen, and R³ and R⁴ are joined to form an optionally substituted 5- to 6-membered heterocyclyl, wherein the optionally substituted 5- to 6-membered heterocyclyl is partially unsaturated. Alternatively, in certain embodiments, the optionally substituted 5- to 6-membered heterocyclyl is saturated.

In certain embodiments, R² is hydrogen, and R³ and R⁴ are joined to form an optionally substituted 6-membered heterocycyl. In certain embodiments, R² is hydrogen, and R³ and R⁴ are joined to form an optionally substituted piperidinyl. In certain embodiments, R² is hydrogen, and R³ and R⁴ are joined to form a substituted piperidinyl.

In certain embodiments, R² is hydrogen, and R³ and R⁴ are joined to form an optionally substituted 5-membered heterocycyl. In certain embodiments, R² is hydrogen, and R³ and R⁴ are joined to form an optionally substituted pyrrolidinyl. In certain embodiments, R² is hydrogen, and R³ and R⁴ are joined to form a substituted pyrrolidinyl.

For example, in certain embodiments, wherein R² is hydrogen, and R³ and R⁴ are joined to form an optionally substituted heterocyclyl, the compound of Formula (I) is of Formula (II):

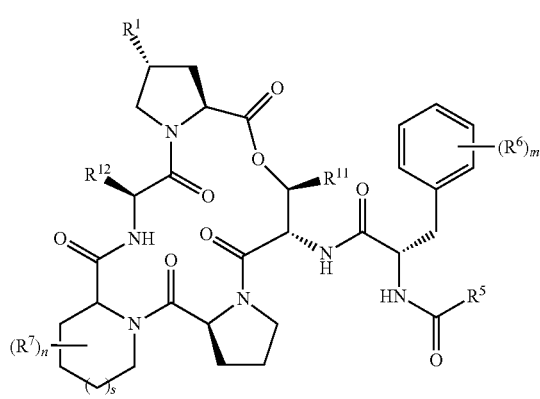

or a pharmaceutically acceptable salt thereof; wherein:
each instance of R⁷ is independently selected from the group consisting of halogen, —OH, —SH, —NH₂, —CN, —NO₂, —N₃, —SO₂H, —SO₃H, substituted hydroxyl, substituted thiol, substituted amino, sulfonyl, sulfinyl, acyl, silyl, boronyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;
n is 0 or an integer of between 1 and 8, inclusive; and s is 0 or 1.

For example, in certain embodiments, wherein n is 1, the compound of Formula (II) is a compound of Formula (II-a):

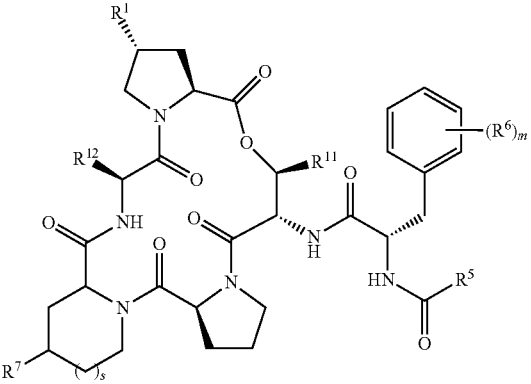

or a pharmaceutically acceptable salt thereof.

In certain embodiments of Formula (I) and (II), the carbon attached to R² and R³ has (S) stereochemistry, e.g., to provide a compound of Formula (II-b):

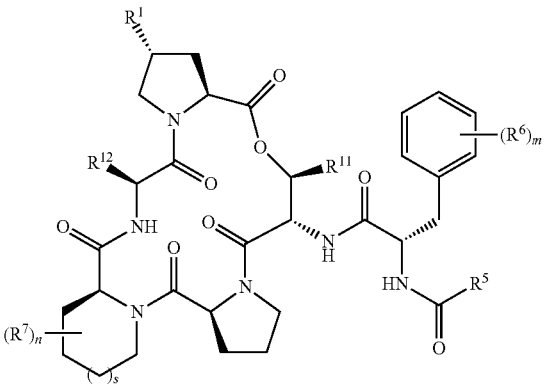

or a pharmaceutically acceptable salt thereof.

In certain embodiments, s is 0, i.e., to provide an optionally substituted pyrrolidinyl. In this instance, in certain embodiments, n is 0, i.e., to provide an unsubstituted pyrrolidinyl. In certain embodiments, n is an integer of between 1 and 8, inclusive, i.e., to provide a substituted pyrrolidinyl. In certain embodiments, n is an integer of between 1 and 7, inclusive. In certain embodiments, n is an integer of between 1 and 6, inclusive. In certain embodiments, n is an integer of between 1 and 5, inclusive. In certain embodiments, n is an integer of between 1 and 4, inclusive. In certain embodiments, n is an integer of between 1 and 3, inclusive. In certain embodiments, n is an integer of between 1 and 2, inclusive. In certain embodiments, n is 1. In certain embodiments, n is 2. In certain embodiments, n is 3. In certain embodiments, n is 4.

In certain embodiments, s is 1, i.e., to provide an optionally substituted piperidinyl. In this instance, in certain embodiments, n is 0, i.e., to provide an unsubstituted piperidinyl. In certain embodiments, n is an integer of between 1 and 8, inclusive, i.e., to provide a substituted piperidinyl. In certain embodiments, n is an integer of between 1 and 7, inclusive. In certain embodiments, n is an integer of between 1 and 6, inclusive. In certain embodiments, n is an integer of between 1 and 5, inclusive. In certain embodiments, n is an integer of between 1 and 4, inclusive. In certain embodiments, n is an integer of between 1 and 3, inclusive. In certain embodiments, n is an integer of between 1 and 2, inclusive. In certain embodiments, n is 1. In certain embodiments, n is 2. In certain embodiments, n is 3. In certain embodiments, n is 4.

As generally defined above, each instance of $R^7$ is independently selected from the group consisting of halogen, —OH, —SH, —NH$_2$, —CN, —NO$_2$, —N$_3$, —SO$_2$H, —SO$_3$H, substituted hydroxyl, substituted thiol, substituted amino, sulfonyl, sulfinyl, acyl, silyl, boronyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, each instance of $R^7$ is independently selected from the group consisting of halogen, —OH, —SH, —NH$_2$, —CN, —NO$_2$, —N$_3$, —SO$_2$H, —SO$_3$H, substituted hydroxyl, substituted thiol, substituted amino, sulfonyl, sulfinyl, acyl, silyl, or boronyl. In certain embodiments, at least one instance of $R^7$ is halogen. In certain embodiments, at least one instance of $R^7$ is —OH. In certain embodiments, at least one instance of $R^7$ is —SH. In certain embodiments, at least one instance of $R^7$ is —NH$_2$. In certain embodiments, at least one instance of $R^7$ is —CN. In certain embodiments, at least one instance of $R^7$ is —NO$_2$. In certain embodiments, at least one instance of $R^7$ is —N$_3$. In certain embodiments, at least one instance of $R^7$ is —SO$_2$H. In certain embodiments, at least one instance of $R^7$ is —SO$_3$H. In certain embodiments, at least one instance of $R^7$ is independently substituted hydroxyl. In certain embodiments, at least one instance of $R^7$ is substituted thiol. In certain embodiments, at least one instance of $R^7$ is substituted amino. In certain embodiments, at least one instance of $R^7$ is sulfonyl. In certain embodiments, at least one instance of $R^7$ is sulfinyl. In certain embodiments, at least one instance of $R^7$ is acyl. In certain embodiments, at least one instance of $R^7$ is silyl. In certain embodiments, at least one instance of $R^7$ is boronyl.

In certain embodiments, each instance of $R^7$ is independently selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl. In certain embodiments, each instance of $R^7$ is independently selected from the group consisting of optionally substituted alkyl, optionally substituted alkenyl, and optionally substituted alkynyl.

In certain embodiments, at least one instance of $R^7$ is optionally substituted alkyl. In certain embodiments, at least one instance of $R^7$ is unsubstituted alkyl. In certain embodiments, at least one instance of $R^7$ is substituted alkyl. In certain embodiments, at least one instance of $R^7$ is optionally substituted $C_{1-10}$alkyl. In certain embodiments, at least one instance of $R^7$ is optionally substituted $C_{1-8}$alkyl. In certain embodiments, at least one instance of $R^7$ is optionally substituted $C_{1-6}$alkyl. In certain embodiments, at least one instance of $R^7$ is optionally substituted $C_{1-4}$alkyl. In certain embodiments, at least one instance of $R^7$ is optionally substituted $C_{1-3}$alkyl. In certain embodiments, at least one instance of $R^7$ is optionally substituted $C_{1-2}$alkyl. In certain embodiments, at least one instance of $R^7$ is optionally substituted $C_1$alkyl. In certain embodiments, at least one instance of $R^7$ is optionally substituted $C_2$alkyl. In certain embodiments, at least one instance of $R^7$ is —CH$_3$, —CH$_2$CH$_3$, —CH(CH$_3$)$_2$, —CH$_2$CH$_2$CH$_3$, or —C(CH$_3$)$_3$, —CH$_2$CH(CH$_3$)$_2$, or —CH$_2$CH$_2$CH(CH$_3$)$_2$.

In certain embodiments, at least one instance of $R^7$ is optionally substituted alkenyl. In certain embodiments, at least one instance of $R^7$ is unsubstituted alkenyl. In certain embodiments, at least one instance of $R^7$ is substituted alkenyl. In certain embodiments, at least one instance of $R^7$ is optionally substituted $C_{2-10}$alkenyl. In certain embodiments, at least one instance of $R^7$ is optionally substituted $C_{2-8}$alkenyl. In certain embodiments, at least one instance of $R^7$ is optionally substituted $C_{2-6}$alkenyl. In certain embodiments, at least one instance of $R^7$ is optionally substituted $C_{2-4}$alkenyl. In certain embodiments, at least one instance of $R^7$ is optionally substituted $C_{2-3}$alkenyl.

In certain embodiments, at least one instance of $R^7$ is optionally substituted alkynyl. In certain embodiments, at least one instance of $R^7$ is unsubstituted alkynyl. In certain embodiments, at least one instance of $R^7$ is substituted alkynyl. In certain embodiments, at least one instance of $R^7$ is optionally substituted $C_{2-10}$alkynyl. In certain embodiments, at least one instance of $R^7$ is optionally substituted $C_{2-8}$alkynyl. In certain embodiments, at least one instance of $R^7$ is optionally substituted $C_{2-6}$alkynyl. In certain embodiments, at least one instance of $R^7$ is optionally substituted $C_{2-4}$alkynyl. In certain embodiments, at least one instance of $R^7$ is optionally substituted $C_{2-3}$alkynyl.

In certain embodiments, at least one instance of $R^7$ is optionally substituted carbocyclyl.

In certain embodiments, at least one instance of $R^7$ is optionally substituted heterocyclyl.

In certain embodiments, at least one instance of $R^7$ is optionally substituted aryl.

In certain embodiments, at least one instance of $R^7$ is optionally substituted heteroaryl.

In certain embodiments of Formula (II), $R^2$ is hydrogen, and $R^3$ and $R^4$ are joined to form an optionally substituted piperidinyl, i.e., to provide a compound of Formula (III):

(III)

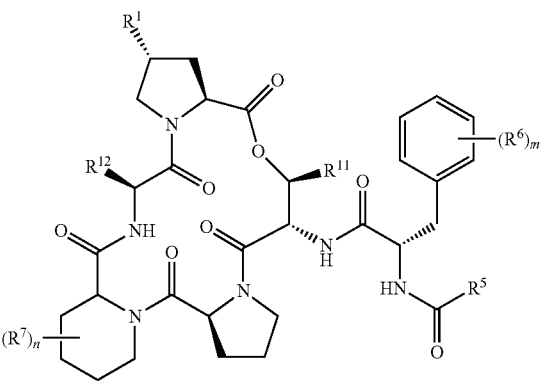

or a pharmaceutically acceptable salt thereof.

In certain embodiments, wherein n is 1, the compound of Formula (III) is a compound of Formula (III-a):

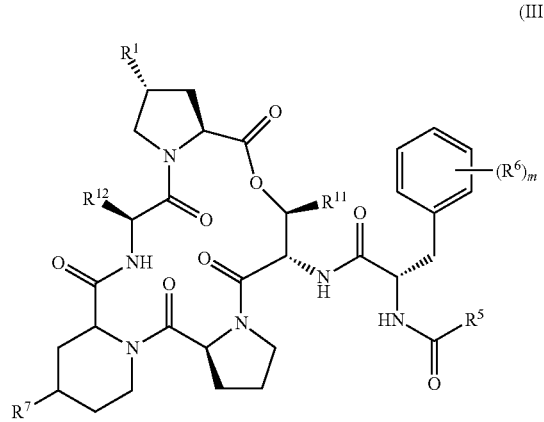

(III-a)

or a pharmaceutically acceptable salt thereof.

In certain embodiments of Formula (I) and (III), the carbon attached to $R^2$ and $R^3$ has (S) stereochemistry, e.g., to provide a compound of Formula (III-b):

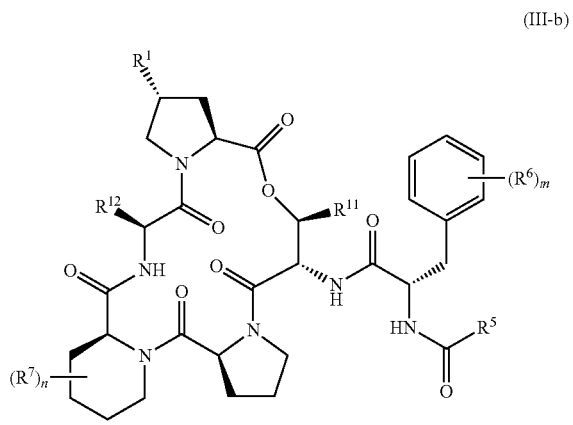

(III-b)

or a pharmaceutically acceptable salt thereof.

In certain embodiments of Formula (II), $R^2$ is hydrogen, and $R^3$ and $R^4$ are joined to form an optionally substituted pyrrolidinyl, i.e., to provide a compound of Formula (IV):

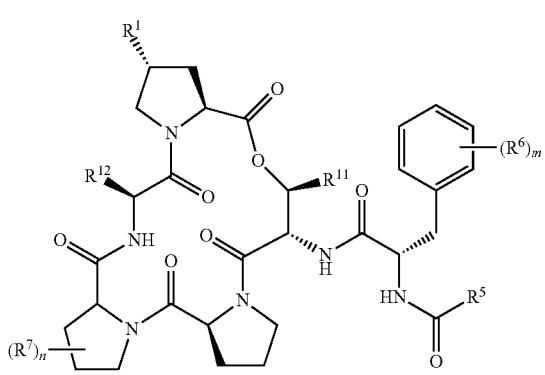

(IV)

or a pharmaceutically acceptable salt thereof.

For example, in certain embodiments, wherein n is 0, the compound of Formula (IV) is a compound of Formula (IV-a):

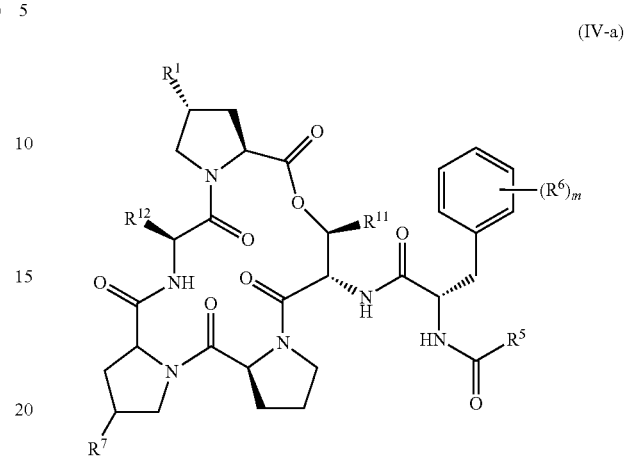

(IV-a)

or a pharmaceutically acceptable salt thereof.

In certain embodiments of Formula (I) and (IV), the carbon attached to $R^2$ and $R^3$ has (S) stereochemistry, e.g., to provide a compound of Formula (IV-b):

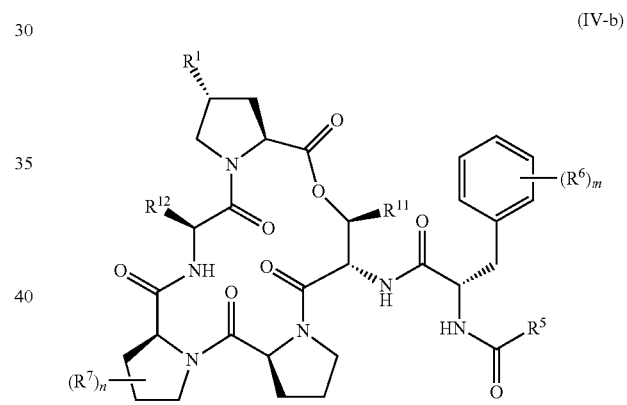

(IV-b)

or a pharmaceutically acceptable salt thereof.

In certain embodiments, $R^2$ and $R^3$ are joined to form a spiro-fused optionally substituted carbocyclyl or spiro-fused optionally substituted heterocyclyl, and $R^4$ is hydrogen, optionally substituted alkyl, or an amino protecting group.

In certain embodiments, $R^2$ and $R^3$ are joined to form a spiro-fused optionally substituted heterocyclyl, and $R^4$ is hydrogen, optionally substituted alkyl, or an amino protecting group. In certain embodiments, $R^2$ and $R^3$ are joined to form a spiro-fused optionally substituted 3-7 membered heterocyclyl. In certain embodiments, $R^2$ and $R^3$ are joined to form a spiro-fused optionally substituted 4-6 membered heterocyclyl. In certain embodiments, $R^2$ and $R^3$ are joined to form a spiro-fused optionally substituted 5-membered heterocyclyl. In certain embodiments, $R^2$ and $R^3$ are joined to form a spiro-fused optionally substituted 6-membered heterocyclyl. In certain embodiments, $R^2$ and $R^3$ are joined to form a spiro-fused optionally substituted 7-membered heterocyclyl. In certain embodiments, the spiro-fused substituted heterocyclyl is substituted.

In certain embodiments, $R^2$ and $R^3$ are joined to form a spiro-fused optionally substituted carbocyclyl and $R^4$ is hydrogen, optionally substituted alkyl, or an amino protecting group. In certain embodiments, $R^2$ and $R^3$ are joined to form a spiro-fused optionally substituted 3-7 membered carbocyclyl. In certain embodiments, $R^2$ and $R^3$ are joined to form a spiro-fused optionally substituted 4-6 membered carbocyclyl. In certain embodiments, $R^2$ and $R^3$ are joined to form a spiro-fused optionally substituted 5-membered carbocyclyl. In certain embodiments, $R^2$ and $R^3$ are joined to form a spiro-fused optionally substituted 6-membered carbocyclyl. In certain embodiments, $R^2$ and $R^3$ are joined to form a spiro-fused optionally substituted 7-membered carbocyclyl. In certain embodiments, the spiro-fused substituted carbocyclyl is substituted.

In certain embodiments, $R^4$ is hydrogen. In certain embodiments, $R^4$ is optionally substituted alkyl (e.g., —CH$_3$, —CH$_2$CH$_3$). In certain embodiments, $R^4$ is an amino protecting group as defined herein.

In certain embodiments, wherein $R^2$ and $R^3$ are joined to form a spiro-fused optionally substituted carbocyclyl, the compound of Formula (I) is a compound of Formula (V):

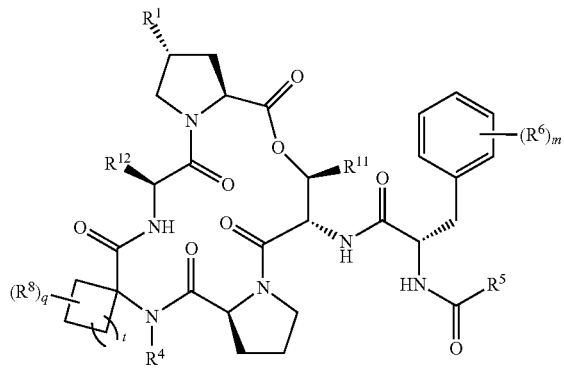

(V)

or a pharmaceutically acceptable salt thereof,
wherein each instance of $R^8$ is independently halogen, —OH, —SH, —NH$_2$, —CN, —NO$_2$, —N$_3$, —SO$_2$H, —SO$_3$H, =O, substituted hydroxyl, substituted thiol, substituted amino, sulfonyl, sulfinyl, acyl, silyl, boronyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
q is 0 or an integer of between 1 and 4, inclusive; and
t is 0 or an integer of between 1 and 4, inclusive.

In certain embodiments, each instance of $R^8$ is independently selected from halogen, —OH, —SH, —NH$_2$, —CN, —NO$_2$, —N$_3$, —SO$_2$H, —SO$_3$H, =O, substituted hydroxyl, substituted thiol, substituted amino, sulfonyl, sulfinyl, acyl, silyl or boronyl. In certain embodiments, at least one instance of $R^8$ is halogen. In certain embodiments, at least one instance of $R^8$ is —OH. In certain embodiments, at least one instance of $R^8$ is —SH. In certain embodiments, at least one instance of $R^8$ is —NH$_2$. In certain embodiments, at least one instance of $R^8$ is —CN. In certain embodiments, at least one instance of $R^8$ is —NO$_2$. In certain embodiments, at least one instance of $R^8$ is —N$_3$. In certain embodiments, at least one instance of $R^8$ is —SO$_2$H. In certain embodiments, at least one instance of $R^8$ is —SO$_3$H. In certain embodiments, at least one instance of $R^8$ is substituted hydroxyl. In certain embodiments, at least one instance of $R^8$ is substituted thiol. In certain embodiments, at least one instance of $R^8$ is substituted amino. In certain embodiments, at least one instance of $R^8$ is sulfonyl. In certain embodiments, at least one instance of $R^8$ is sulfinyl. In certain embodiments, at least one instance of $R^8$ is acyl. In certain embodiments, at least one instance of $R^8$ is silyl. In certain embodiments, at least one instance of $R^8$ is boronyl. In certain embodiments, at least one instance of $R^8$ is =O.

In certain embodiments, each instance of $R^8$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, each instance of $R^8$ is independently optionally substituted alkyl, optionally substituted alkenyl, or optionally substituted alkynyl.

In certain embodiments, at least one instance of $R^8$ is optionally substituted alkyl. In certain embodiments, at least one instance of $R^8$ is unsubstituted alkyl. In certain embodiments, at least one instance of $R^8$ is substituted alkyl. In certain embodiments, at least one instance of $R^8$ is optionally substituted $C_{1-10}$alkyl. In certain embodiments, at least one instance of $R^8$ is optionally substituted $C_{1-8}$alkyl. In certain embodiments, at least one instance of $R^8$ is optionally substituted $C_{1-6}$alkyl. In certain embodiments, at least one instance of $R^8$ is optionally substituted $C_{1-4}$alkyl. In certain embodiments, at least one instance of $R^8$ is optionally substituted $C_{1-3}$alkyl. In certain embodiments, at least one instance of $R^8$ is optionally substituted $C_{1-2}$alkyl. In certain embodiments, at least one instance of $R^8$ is optionally substituted $C_1$alkyl. In certain embodiments, at least one instance of $R^8$ is optionally substituted $C_2$alkyl. In certain embodiments, at least one instance of $R^8$ is —CH$_3$, —CH$_2$CH$_3$, —CH(CH$_3$)$_2$, —CH$_2$CH$_2$CH$_3$, or —C(CH$_3$)$_3$, —CH$_2$CH(CH$_3$)$_2$, or —CH$_2$CH$_2$CH(CH$_3$)$_2$.

In certain embodiments, at least one instance of $R^8$ is optionally substituted alkenyl. In certain embodiments, at least one instance of $R^8$ is unsubstituted alkenyl. In certain embodiments, at least one instance of $R^8$ is substituted alkenyl. In certain embodiments, at least one instance of $R^8$ is optionally substituted $C_{2-10}$alkenyl. In certain embodiments, at least one instance of $R^8$ is optionally substituted $C_{2-8}$alkenyl. In certain embodiments, at least one instance of $R^8$ is optionally substituted $C_{2-6}$alkenyl. In certain embodiments, at least one instance of $R^8$ is optionally substituted $C_{2-4}$alkenyl. In certain embodiments, at least one instance of $R^8$ is optionally substituted $C_{2-3}$alkenyl.

In certain embodiments, at least one instance of $R^8$ is optionally substituted alkynyl. In certain embodiments, at least one instance of $R^8$ is unsubstituted alkynyl. In certain embodiments, at least one instance of $R^8$ is substituted alkynyl. In certain embodiments, at least one instance of $R^8$ is optionally substituted $C_{2-10}$alkynyl. In certain embodiments, at least one instance of $R^8$ is optionally substituted $C_{2-8}$alkynyl. In certain embodiments, at least one instance of $R^8$ is optionally substituted $C_{2-6}$alkynyl. In certain embodiments, at least one instance of $R^8$ is optionally substituted $C_{2-4}$alkynyl. In certain embodiments, at least one instance of $R^8$ is optionally substituted $C_{2-3}$ alkynyl.

In certain embodiments, at least one instance of $R^8$ is optionally substituted carbocyclyl.

In certain embodiments, at least one instance of $R^8$ is optionally substituted heterocyclyl.

In certain embodiments, at least one instance of $R^8$ is optionally substituted aryl.

In certain embodiments, at least one instance of $R^8$ is optionally substituted heteroaryl.

In certain embodiments, q is 0. In certain embodiments, q is an integer of between 1 and 4, inclusive. In certain embodiments, q is an integer of between 1 and 3, inclusive. In certain embodiments, q is an integer of between 1 and 2, inclusive. In certain embodiments, q is 1. In certain embodiments, q is 2. In certain embodiments, q is 3. In certain embodiments, q is 4.

In certain embodiments, t is 0. In certain embodiments, t is 1. In certain embodiments, t is 2. In certain embodiments, t is 3. In certain embodiments, t is 4.

For example, in certain embodiments, wherein t is 0, the compound of Formula (V) is a compound of Formula (V-a):

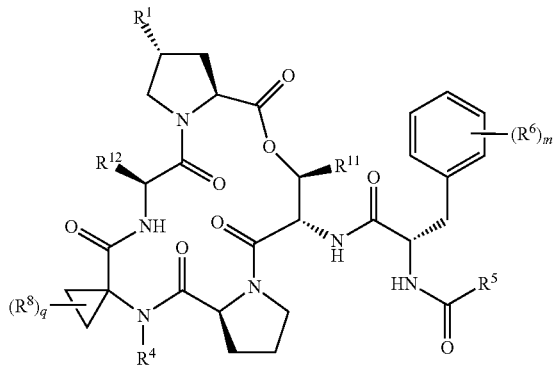

(V-a)

or a pharmaceutically acceptable salt thereof.

In certain embodiments, wherein t is 1, the compound of Formula (V) is a compound of Formula (V-b):

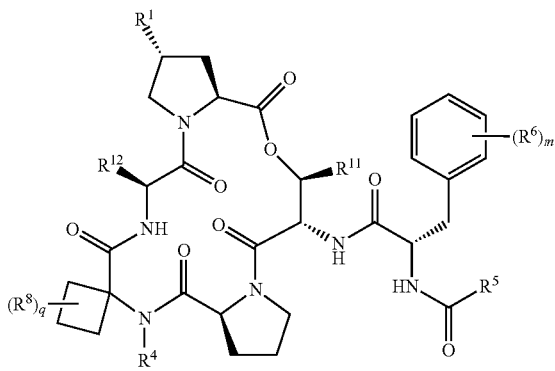

(V-b)

or a pharmaceutically acceptable salt thereof.

In certain embodiments, wherein t is 2, the compound of Formula (V) is a compound of Formula (V-c):

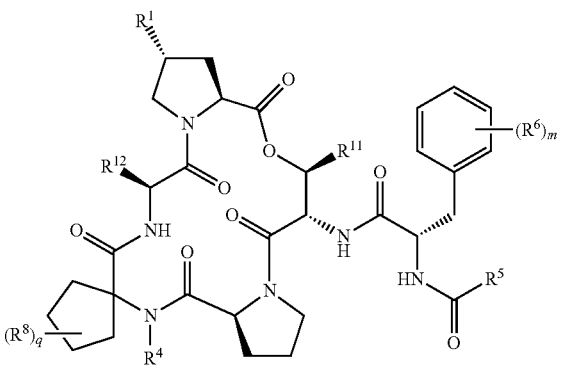

(V-c)

or a pharmaceutically acceptable salt thereof.

In certain embodiments, wherein t is 3, the compound of Formula (V) is a compound of Formula (V-d):

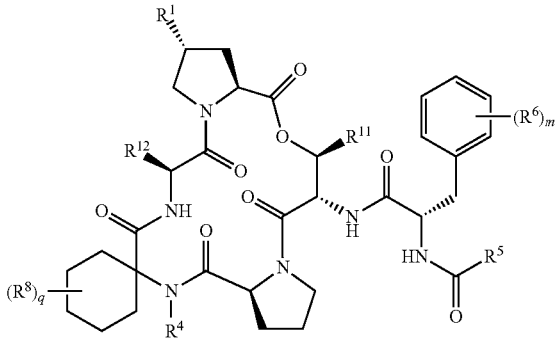

(V-d)

or a pharmaceutically acceptable salt thereof.

In certain embodiments, wherein t is 4, the compound of Formula (V) is a compound of Formula (V-e):

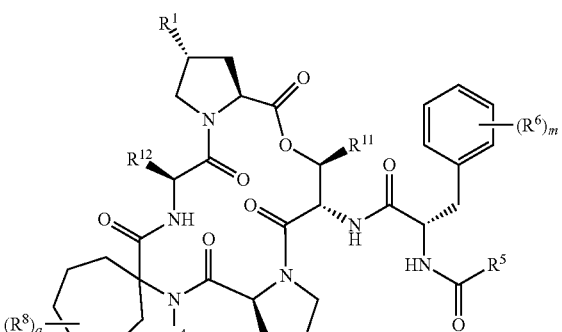

(V-e)

or a pharmaceutically acceptable salt thereof.

In certain embodiments, $R^2$ and $R^3$ are independently selected from hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, with the proviso that $R^2$ and $R^3$ are not both hydrogen; and $R^4$ is hydrogen, an optionally substituted alkyl, or an amino protecting group.

In certain embodiments, $R^4$ is hydrogen. In certain embodiments, $R^4$ is optionally substituted alkyl (e.g., —$CH_3$, —$CH_2CH_3$). In certain embodiments, $R^4$ is an amino protecting group as defined herein.

In certain embodiments, $R^2$ is hydrogen and $R^3$ is independently selected from optionally substituted alkyl, optionally substituted alkenyl, optionally substituted alkynyl, optionally substituted carbocyclyl, optionally substituted heterocyclyl, optionally substituted aryl, and optionally substituted heteroaryl. In certain embodiments, the stereochemistry of the carbon attached to $R^2$ and $R^3$ may be (R) or (S). In certain embodiments, the stereochemistry of the carbon attached to $R^2$ and $R^3$ is (R). In certain embodiments, the stereochemistry of the carbon attached to $R^2$ and $R^3$ is (S).

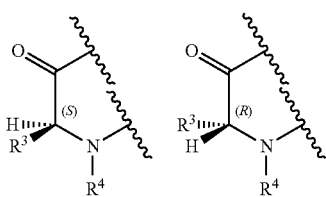

For example, in certain embodiments wherein $R^2$ is hydrogen and the stereochemistry of the carbon attached to $R^2$ and $R^3$ is (S), the compound of Formula (I) is a compound of Formula (VI):

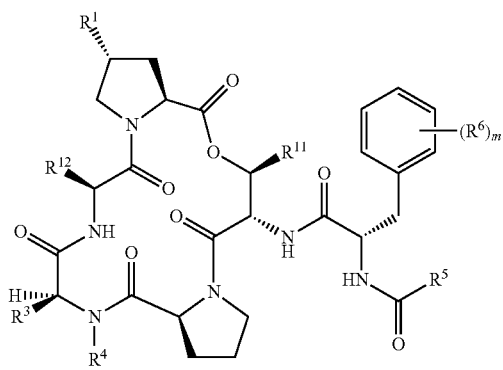

or a pharmaceutically acceptable salt thereof.

In certain embodiments wherein $R^2$ is hydrogen and the stereochemistry of the carbon attached to $R^2$ and $R^3$ is (R), the compound of Formula (I) is a compound of Formula (VII):

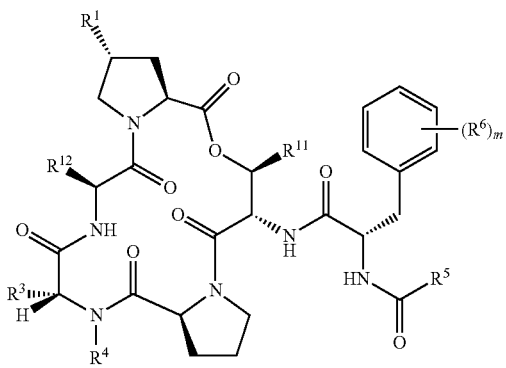

or a pharmaceutically acceptable salt thereof.

In certain embodiments, $R^2$ is hydrogen and $R^3$ is optionally substituted alkyl. In certain embodiments, $R^2$ is hydrogen and $R^3$ is a substituted alkyl. In certain embodiments, $R^2$ is hydrogen and $R^3$ is optionally substituted $C_{1-10}$ alkyl. In certain embodiments, $R^2$ is hydrogen and $R^3$ is optionally substituted $C_{1-8}$ alkyl. In certain embodiments, $R^2$ is hydrogen and $R^3$ is optionally substituted $C_{1-6}$ alkyl. In certain embodiments, $R^2$ is hydrogen and $R^3$ is optionally substituted $C_{1-4}$ alkyl. In certain embodiments, $R^2$ is hydrogen and $R^3$ is optionally substituted $C_{1-3}$ alkyl. In certain embodiments, $R^2$ is hydrogen and $R^3$ is optionally substituted $C_{1-2}$ alkyl. In certain embodiments, $R^2$ is hydrogen and $R^3$ is optionally substituted $C_{2-10}$ alkyl. In certain embodiments, $R^2$ is hydrogen and $R^3$ is optionally substituted $C_{2-8}$ alkyl. However, in certain embodiments, wherein $R^2$ is hydrogen and $R^3$ is optionally substituted alkyl, —$CH_2OR^{10}$ wherein $R^{10}$ is hydrogen or acyl is specifically excluded.

In certain embodiments, $R^2$ is hydrogen and $R^3$ is optionally substituted alkenyl. In certain embodiments, $R^2$ is hydrogen and $R^3$ is a substituted alkenyl. In certain embodiments, $R^2$ is hydrogen and $R^3$ is optionally substituted $C_{2-10}$alkenyl. In certain embodiments, $R^2$ is hydrogen and $R^3$ is optionally substituted $C_{2-8}$alkenyl. In certain embodiments, $R^2$ is hydrogen and $R^3$ is optionally substituted $C_{2-6}$alkenyl. In certain embodiments, $R^2$ is hydrogen and $R^3$ is optionally substituted $C_{2-4}$alkenyl. In certain embodiments, $R^2$ is hydrogen and $R^3$ is optionally substituted $C_{2-3}$alkenyl.

In certain embodiments, $R^2$ is hydrogen and $R^3$ is optionally substituted alkynyl. In certain embodiments, $R^2$ is hydrogen and $R^3$ is a substituted alkynyl. In certain embodiments, $R^2$ is hydrogen and $R^3$ is optionally substituted $C_{2-10}$alkynyl. In certain embodiments, $R^2$ is hydrogen and $R^3$ is optionally substituted $C_{2-8}$alkynyl. In certain embodiments, $R^2$ is hydrogen and $R^3$ is optionally substituted $C_{2-6}$alkynyl. In certain embodiments, $R^2$ is hydrogen and $R^3$ is optionally substituted $C_{2-4}$alkynyl. In certain embodiments, $R^2$ is hydrogen and $R^3$ is optionally substituted $C_{2-3}$ alkynyl.

In certain embodiments, $R^2$ is hydrogen and $R^3$ is optionally substituted carbocyclyl.

In certain embodiments, $R^2$ is hydrogen and $R^3$ is optionally substituted heterocyclyl.

In certain embodiments, $R^2$ is hydrogen and $R^3$ is optionally substituted aryl.

In certain embodiments, $R^2$ is hydrogen and $R^3$ is optionally substituted heteroaryl.

In certain embodiments, neither $R^2$ nor $R^3$ are hydrogen, i.e., $R^2$ and $R^3$ are independently selected from optionally substituted alkyl, optionally substituted alkenyl, optionally substituted alkynyl, optionally substituted carbocyclyl, optionally substituted heterocyclyl, optionally substituted aryl, and optionally substituted heteroaryl. In this instance, $R^2$ and $R^3$ are the same, or $R^2$ and $R^3$ are different.

In certain embodiments, $R^2$ and $R^3$ are the same and are selected from optionally substituted alkyl, optionally substituted alkenyl, optionally substituted alkynyl, optionally substituted carbocyclyl, optionally substituted heterocyclyl, optionally substituted aryl, and optionally substituted heteroaryl. For example, in certain embodiments, $R^2$ and $R^3$ are the same optionally substituted alkyl groups.

In certain embodiments, $R^2$ and $R^3$ are the different and are selected from optionally substituted alkyl, optionally substituted alkenyl, optionally substituted alkynyl, optionally substituted carbocyclyl, optionally substituted aryl, and optionally substituted heteroaryl. For example, in certain embodiments, $R^2$ and $R^3$ are different optionally substituted alkyl groups.

As generally defined above, $R^5$ is —OH, —SH, —$NH_2$, substituted hydroxyl, substituted thiol, substituted amino, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $R^5$ is —OH. In certain embodiments, $R^5$ is —SH. In certain embodiments, $R^5$ is —$NH_2$. In certain embodiments, $R^5$ is substituted hydroxyl. In certain embodiments, $R^5$ is substituted thiol. In certain embodiments, $R^5$ is substituted amino.

In certain embodiments, $R^5$ is optionally substituted alkyl. In certain embodiments, $R^5$ is unsubstituted alkyl. In certain embodiments, $R^5$ is substituted alkyl. In certain embodiments, $R^5$ is optionally substituted $C_{1-30}$alkyl. In certain embodiments, $R^5$ is optionally substituted $C_{1-25}$alkyl. In certain embodiments, $R^5$ is optionally substituted $C_{1-15}$alkyl. In certain embodiments, $R^5$ is optionally substituted $C_{1-10}$alkyl. In certain embodiments, $R^5$ is optionally substituted $C_{2-10}$alkyl. In certain embodiments, $R^5$ is optionally substituted $C_{3-8}$alkyl. In certain embodiments, $R^5$ is optionally substituted $C_{5-15}$alkyl.

In certain embodiments, $R^5$ is optionally substituted alkenyl. In certain embodiments, $R^5$ is an unsubstituted alkenyl. In certain embodiments, $R^5$ is a substituted alkenyl. In certain embodiments, $R^5$ is optionally substituted $C_{2-30}$ alkenyl. In certain embodiments, $R^5$ is optionally substituted $C_{2-25}$ alkenyl. In certain embodiments, $R^5$ is optionally substituted $C_{2-15}$ alkenyl. In certain embodiments, $R^5$ is optionally substituted $C_{2-10}$ alkenyl. In certain embodiments, $R^5$ is optionally substituted $C_{3-8}$ alkenyl. In certain embodiments, $R^5$ is optionally substituted $C_{5-15}$ alkenyl.

In certain embodiments, $R^5$ is a $C_{7-30}$alkyl or $C_{7-30}$alkenyl. In these instances, in certain embodiments, these groups may also collectively be referred to as "hydrocarbon tails." Hydrocarbon tails can be saturated and unsaturated, depending on whether or not the hydrocarbon tail comprises double bonds. The hydrocarbon tail can also comprise different lengths, often categorized as medium (i.e., with tails between 7-12 carbons, e.g., $C_{7-12}$ alkyl or $C_{7-12}$ alkenyl), long (i.e., with tails greater than 12 carbons and up to 22 carbons, e.g., $C_{13-22}$ alkyl or $C_{13-22}$ alkenyl), or very long (i.e., with tails greater than 22 carbons, e.g., $C_{23-30}$ alkyl or $C_{23-30}$ alkenyl).

Exemplary unsaturated hydrocarbon tails include, but are not limited to:

Myristoleic —$(CH_2)_7CH=CH(CH_2)_3CH_3$,
Palmitoliec —$(CH_2)_7CH=CH(CH_2)_5CH_3$,
Sapienic —$(CH_2)_4CH=CH(CH_2)_8CH_3$,
Oleic —$(CH_2)_7CH=CH(CH_2)_7CH_3$,
Linoleic —$(CH_2)_7CH=CHCH_2CH=CH(CH_2)_4CH_3$,
α-Linolenic —$(CH_2)_7CH=CHCH_2CH=CHCH_2CH=CHCH_2CH_3$,
Arachinodonic —$(CH_2)_3CH=CHCH_2CH=CHCH_2CH=CHCH_2CH=CH(CH_2)_4CH_3$,
Eicosapentaenoic —$(CH_2)_3CH=CHCH_2CH=CHCH_2CH=CHCH_2CH=CHCH_2CH=CHCH_2CH_3$,
Erucic —$(CH_2)_{11}CH=CH(CH_2)_7CH_3$, and
Docosahexaenoic —$(CH_2)_2CH=CHCH_2CH=CHCH_2CH=CHCH_2CH=CHCH_2CH=CHCH_2CH=CH—CH_2CH_3$.

Exemplary saturated hydrocarbon tails include, but are not limited to:

Lauric —$(CH_2)_{10}CH_3$,
Myristic —$(CH_2)_{12}CH_3$,
Palmitic —$(CH_2)_{14}CH_3$,
Stearic —$(CH_2)_{16}CH_3$,
Arachidic —$(CH_2)_{18}CH_3$,
Behenic —$(CH_2)_{20}CH_3$,
Lignoceric —$(CH_2)_{22}CH_3$, and
Cerotic —$(CH_2)_{24}CH_3$.

In certain embodiments, $R^5$ is an optionally substituted alkenyl group of formula (a):

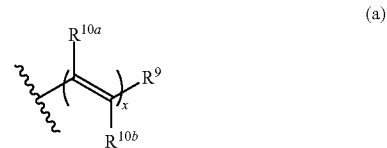

(a)

wherein:
x is an integer between 1 and 10, inclusive;
$R^{10a}$ and $R^{10b}$ are independently hydrogen or optionally substituted alkyl; and
$R^9$ is hydrogen, halogen, —OH, —SH, —$NH_2$, —CN, —$NO_2$, —$N_3$, —$SO_2H$, —$SO_3H$, substituted hydroxyl, substituted thiol, substituted amino, sulfonyl, sulfinyl, acyl, silyl, boronyl, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, x is an integer between 1 and 8, inclusive. In certain embodiments, x is an integer between 1 and 6, inclusive. In certain embodiments, x is an integer between 1 and 5, inclusive. In certain embodiments, x is an integer between 1 and 4, inclusive. In certain embodiments, x is an integer between 1 and 3, inclusive. In certain embodiments, x is an integer between 1 and 2, inclusive. In certain embodiments, x is 1. In certain embodiments, x is 2. In certain embodiments, x is 3. In certain embodiments, x is 4. In certain embodiments, x is 5.

In certain embodiments, $R^{10a}$ and $R^{10b}$ are both hydrogen. In certain embodiments, $R^{10a}$ and $R^{10b}$ are independently selected from hydrogen and —$CH_3$.

In certain embodiments, $R^9$ is selected from acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $R^9$ is a acyl, as defined herein.

In certain embodiments, $R^9$ is optionally substituted alkyl (e.g., —$CH_3$, —$CH_2CH_3$, —$CH_2CH_2CH_3$, —$CH_2CH_2CH_2CH_3$).

In certain embodiments, the alkenyl group of Formula (a) is selected from:

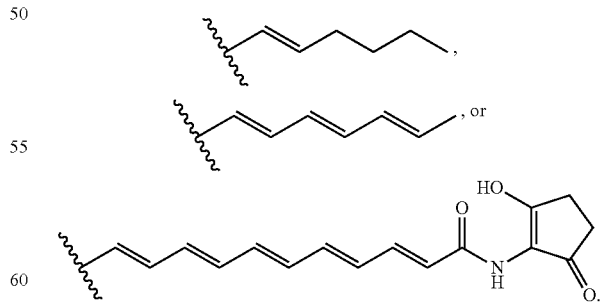

In certain embodiments, $R^5$ is optionally substituted alkynyl. In certain embodiments, $R^5$ is an unsubstituted alkynyl. In certain embodiments, $R^5$ is a substituted alkynyl. In certain embodiments, $R^5$ is optionally substituted $C_{2-30}$ alkynyl. In certain embodiments, $R^5$ is optionally substituted $C_{2-25}$ alkynyl. In certain embodiments, $R^5$ is optionally substituted $C_{2-15}$ alkynyl. In certain embodiments, $R^5$ is optionally substituted $C_{2-10}$ alkynyl. In certain embodiments, $R^5$ is optionally substituted $C_{3-8}$ alkynyl. In certain embodiments, $R^5$ is optionally substituted $C_{5-15}$ alkynyl.

As generally described above, $R^{11}$ is hydrogen, —OH, —SH, —NH$_2$, substituted hydroxyl, substituted thiol, substituted amino, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^{11}$ is hydrogen. In certain embodiments, $R^{11}$ is optionally substituted alkyl. In certain embodiments, $R^{11}$ is $C_{1-3}$ optionally substituted alkyl, e.g., —CH$_3$, —CF$_3$, —CH$_2$CH$_3$, or —CH(CH$_3$)$_2$. In certain embodiments, $R^{11}$ is —CH$_3$.

As generally described above, $R^{12}$ is hydrogen, —OH, —SH, —NH$_2$, substituted hydroxyl, substituted thiol, substituted amino, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^{12}$ is hydrogen. In certain embodiments, $R^{12}$ is optionally substituted alkyl. In certain embodiments, $R^{12}$ is $C_{1-3}$ optionally substituted alkyl, e.g., —CH$_3$, —CF$_3$, —CH$_2$CH$_3$, or —CH(CH$_3$)$_2$. In certain embodiments, $R^{12}$ is —CH$_3$.

As generally described above, each instance of $R^6$ is independently selected from halogen, —OH, —SH, —NH$_2$, —CN, —NO$_2$, —N$_3$, —SO$_2$H, —SO$_3$H, substituted hydroxyl, substituted thiol, substituted amino, sulfonyl, sulfinyl, acyl, silyl, boronyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; and m is 0 or an integer of between 1 and 5, inclusive.

In certain embodiments, m is 0. In certain embodiments, m is an integer of between 1 and 5, inclusive. In certain embodiments, m is an integer of between 1 and 4, inclusive. In certain embodiments, m is an integer of between 1 and 3, inclusive. In certain embodiments, m is an integer of between 1 and 2, inclusive. In certain embodiments, m is 1, i.e., to provide a monosubstituted phenyl. In certain embodiments, m is 2, i.e., to provide a disubstituted phenyl. In certain embodiments, m is 3, i.e., to provide a trisubstituted phenyl. In certain embodiments, m is 4, i.e., to provide a tetrasubstituted phenyl. In certain embodiments, m is 5, i.e., to provide a pentasubstituted phenyl.

In certain preferred embodiments, m is 1 or 2 to provide a monosubstituted or disubstituted phenyl. In this instance, all possible positional mono- and di-substituted isomers are contemplated herein, i.e.:

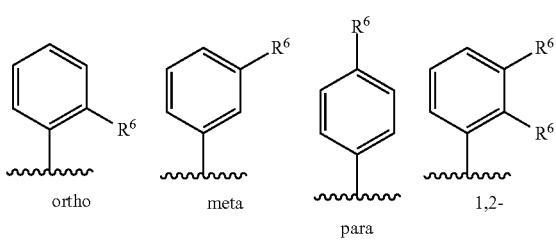

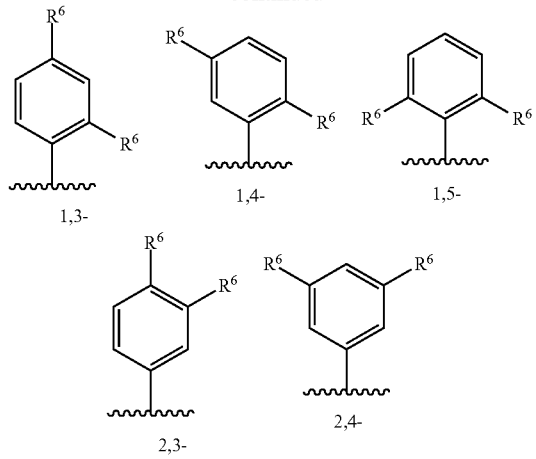

For example, in certain embodiments, m is 1, i.e., to provide a monosubstituted phenyl. In this instance, $R^6$ may be an ortho-, meta- or para-substituent relative to the point of attachment to the parent molecule. In certain embodiments, $R^6$ is an ortho-substituent. In certain embodiments, $R^6$ is a meta-substituent. In certain embodiments, $R^6$ is a para-substituent.

In certain embodiments, m is 2, i.e., to provide a disubstituted phenyl. In this instance, the two $R^6$ substituents are 1,2-substituents, 1,3-substituents, 1,4-substituents, 1,5-substituents, 2,3-substituents, or 2,4-substituents, relative to the point of attachment to the parent molecule. In certain embodiments, the two $R^6$ substituents are 1,2-substituents. In certain embodiments, the two $R^6$ substituents are 1,3-substituents. In certain embodiments, the two $R^6$ substituents are 1,4-substituents. In certain embodiments, the two $R^6$ substituents are 1,5-substituents. In certain embodiments, the two $R^6$ substituents are 2,3-substituents. In certain embodiments, the two $R^6$ substituents are 2,4-substituents.

In certain embodiments, each instance of $R^6$ is independently selected from halogen, —OH, —SH, —NH$_2$, —CN, —NO$_2$, —N$_3$, —SO$_2$H, —SO$_3$H, substituted hydroxyl, substituted thiol, substituted amino, sulfonyl, sulfinyl, acyl, and boronyl. In certain embodiments, each instance of $R^6$ is independently selected from halogen, —OH, —SH, —NH$_2$, —SO$_2$H, —SO$_3$H. In certain embodiments, each instance of $R^6$ is independently selected from halogen, —OH, or —NH$_2$.

In certain embodiments, each instance of $R^6$ is halogen, e.g., fluoro (—F), chloro (—Cl), bromo (—Br), or iodo (—I). In certain embodiments, each instance of $R^6$ is fluoro. In certain embodiments, m is 1 and $R^6$ is fluoro. In certain embodiments, m is 1 and $R^6$ is a meta fluoro substituent. In certain embodiments, m is 2 and each $R^6$ is fluoro. In certain embodiments, m is 2 and the two $R^6$ groups are 2,4-fluoro substituents.

In certain embodiments, each instance of $R^6$ is —OH. In certain embodiments, m is 1 and $R^6$ is —OH. In certain embodiments, m is 1 and $R^6$ is —OH. In certain embodiments, m is 1 and $R^6$ is a meta —OH substituent.

In certain embodiments, each instance of $R^6$ is —NH$_2$. In certain embodiments, m is 1 and $R^6$ is —NH$_2$. In certain embodiments, m is 1 and $R^6$ is a meta —NH$_2$ substituent.

For example, in certain embodiments of Formula (I), wherein m is 1 or 2, provided is a compound of Formula (I-b) or (I-c):

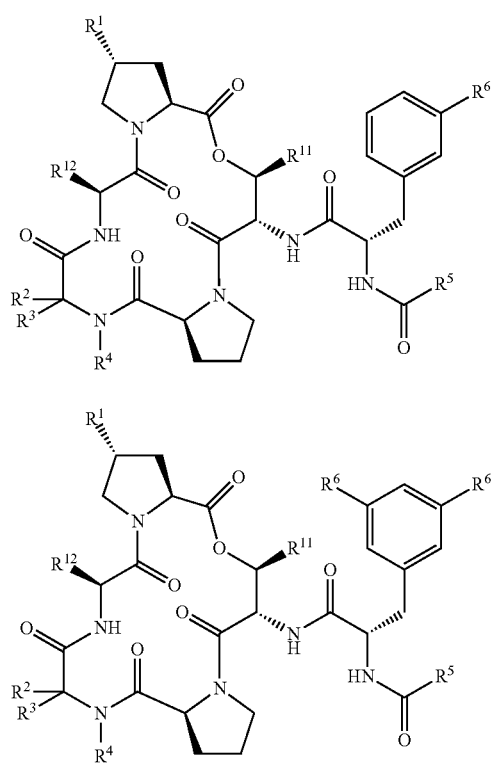
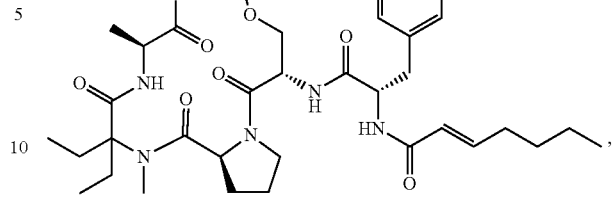
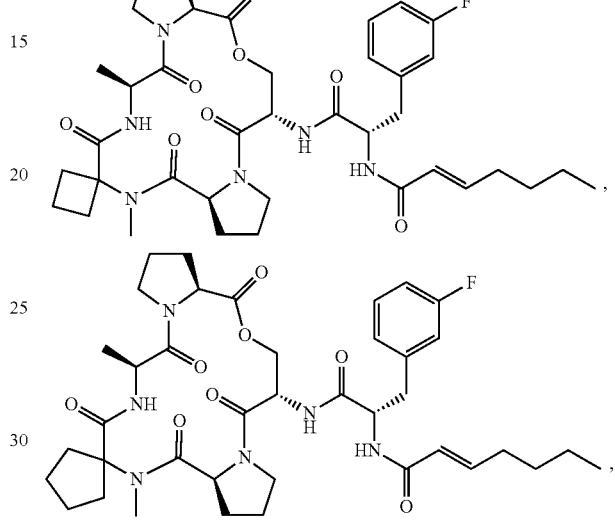
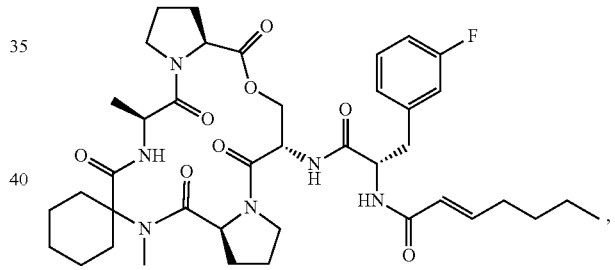
or a pharmaceutically acceptable salt thereof.
However, in certain embodiments, the compound of Formula (I) is not Enopeptin A, Enopeptin B, A54556A, A54556B, or ADEP4, or salt thereof, as depicted in FIG. 1. In certain embodiments, the compound of Formula (I) is not a compound or salt thereof as depicted in WO2003/024996.
Exemplary compounds of Formula (I) include, but are not limited to:
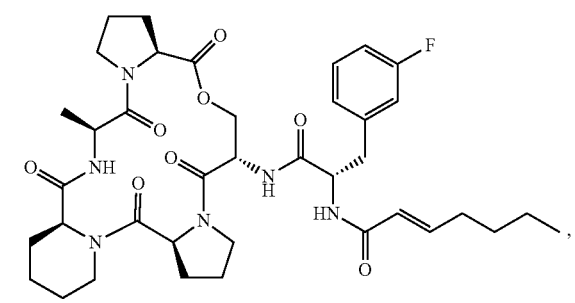
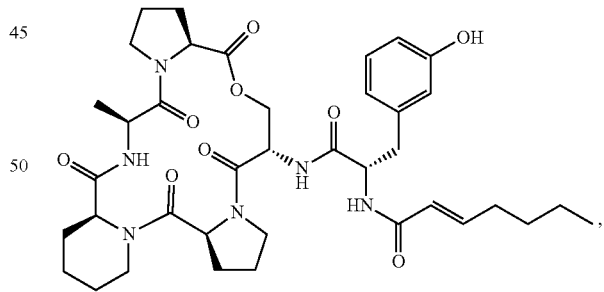
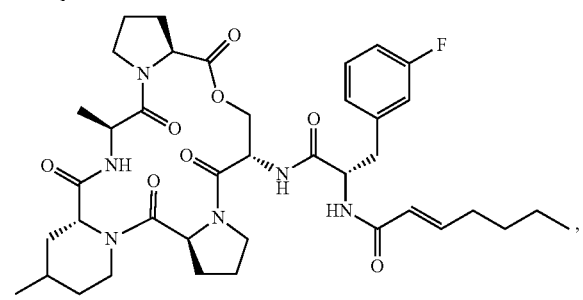
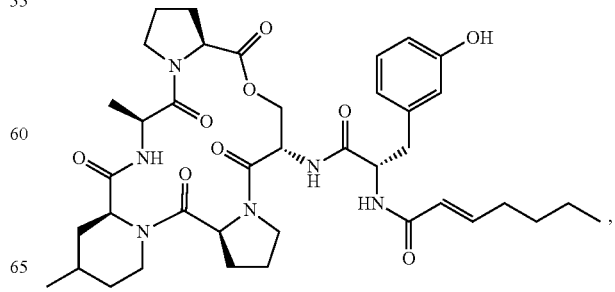

41
-continued
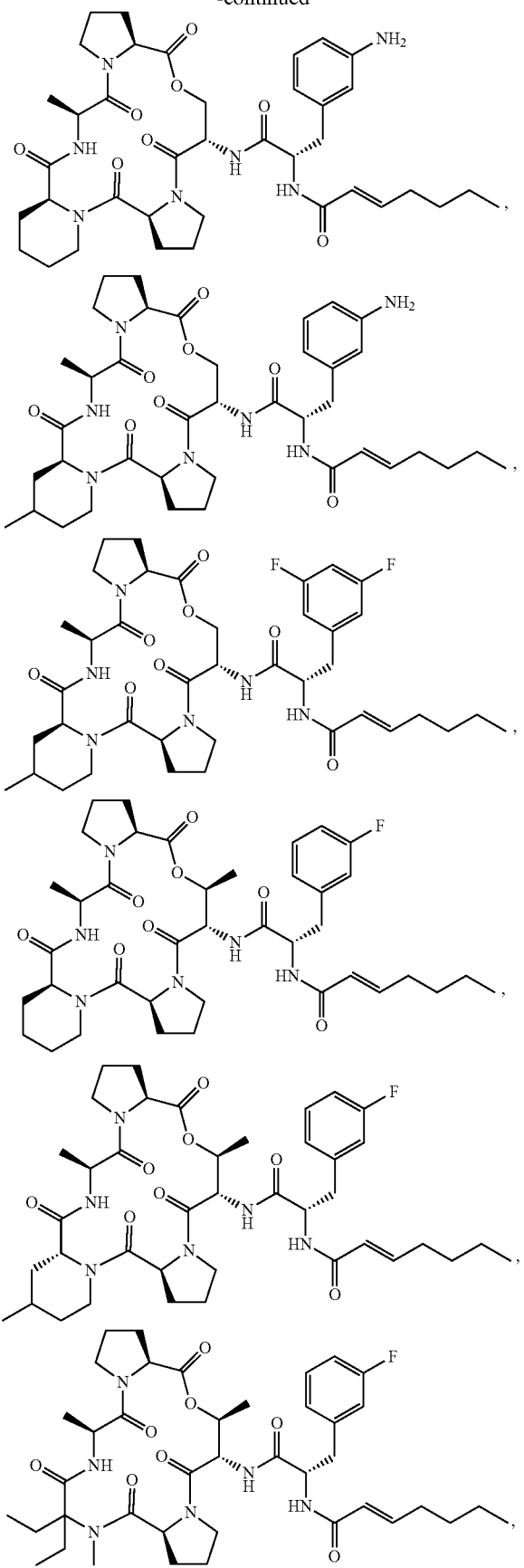
42
-continued
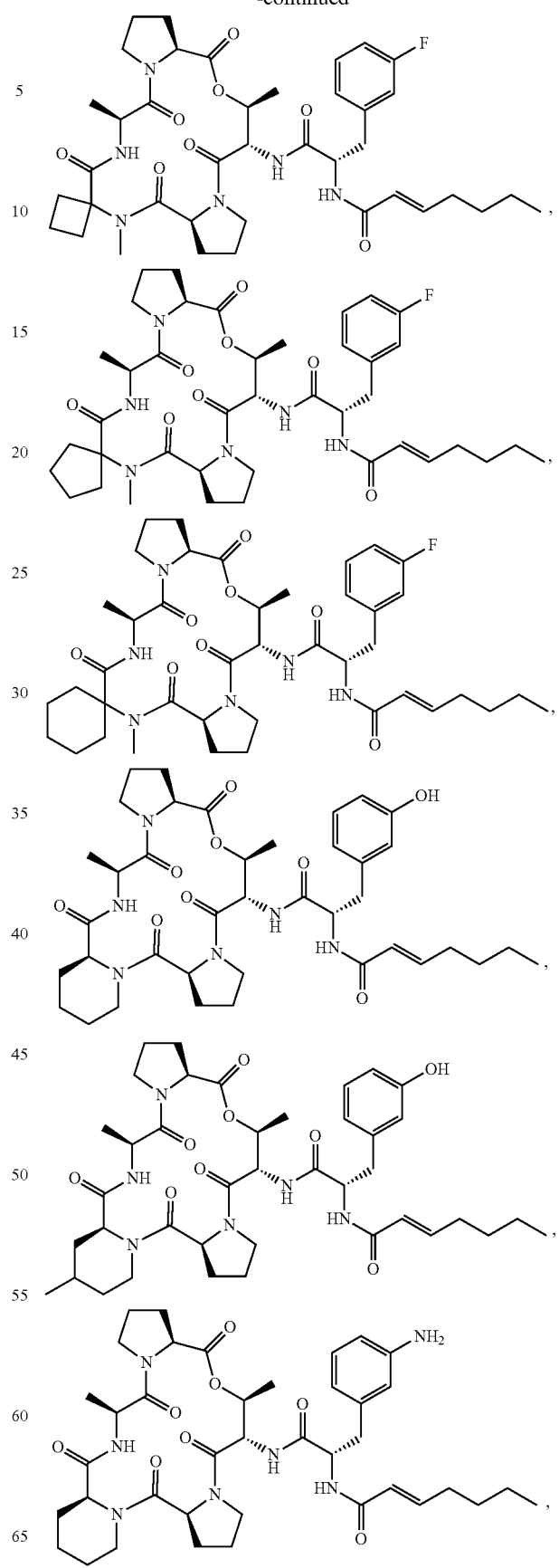

-continued

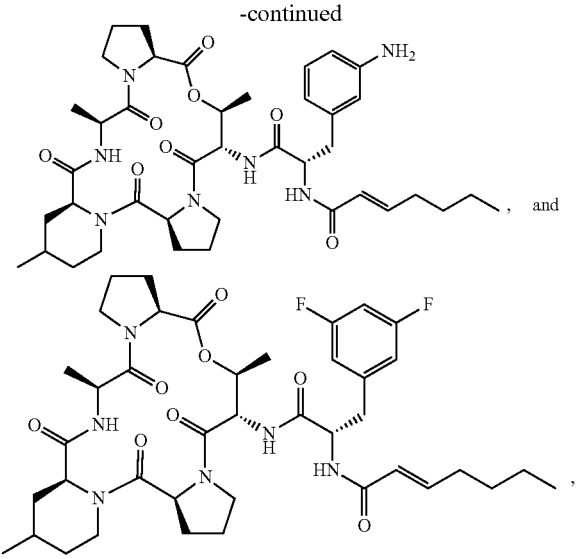

, and

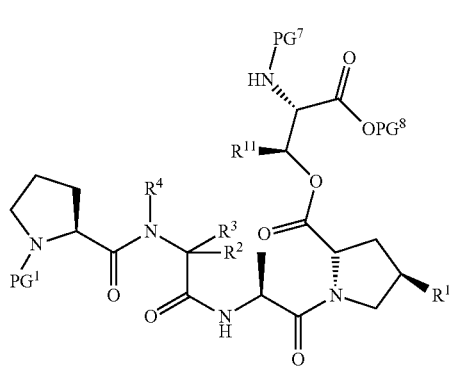

, and pharmaceutically acceptable salts thereof.

Methods of Synthesis

The present invention also provides methods of preparing compounds of Formula (I). The method is a convergent approach and employs various deprotections and peptide coupling throughout the synthesis. Deprotecting conditions are well known in the art (see, e.g., *Protecting Groups in Organic Synthesis*, T. W. Greene and P. G. M. Wuts, 3$^{rd}$ edition, John Wiley & Sons, 1999). Reagents and conditions for peptide coupling (e.g., uronium, immonium, carbodiimide, imidazolium, organophosphorous coupling reagents) are also well known in the art; see, e.g., Han and Kim, *Tetrahedron* (2004) 60:2447-2467.

For example, in one aspect, provided is a method of preparing a compound of Formula (C):

(C)

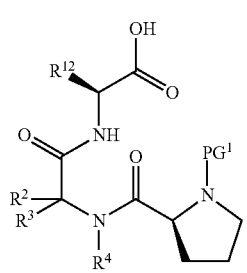

or salt thereof; comprising coupling a compound of Formula (A), or salt thereof, with a compound of Formula (B), or salt thereof:

(A)

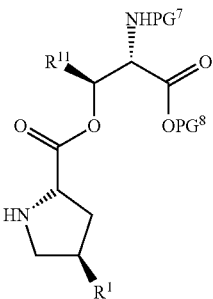

(B)

wherein PG$^1$ and PG$^7$ are amino protecting groups, as defined herein; and PG$^8$ is an oxygen protecting group, as defined herein.

In certain embodiments, PG$^1$ is a -Boc group. In certain embodiments, PG$^7$ is a Cbz group. In certain embodiments, PG$^8$ is a 2-hydroxy-1-phenylethanone (HPE) group.

In certain embodiments, the method further comprises deprotecting the compound of Formula (C), or salt thereof, to provide a compound of Formula (E):

(E)

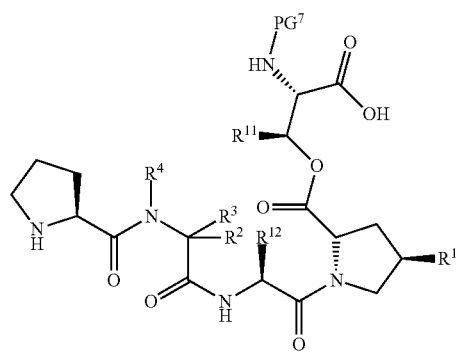

or salt thereof.

In certain embodiments, the method further comprises cyclizing the compound of Formula (E), or salt thereof, to provide a compound of Formula (F):

(F)

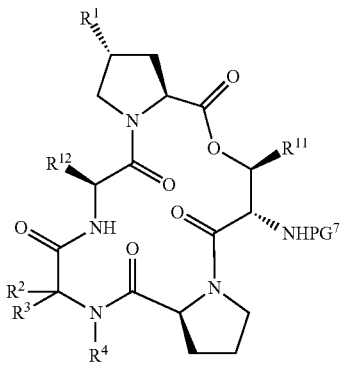

or salt thereof.

The cyclization reaction is an intramolecular peptide coupling reaction.

In certain embodiments, the method further comprises deprotecting the compound of Formula (F), or salt thereof, to provide a compound of Formula (G):

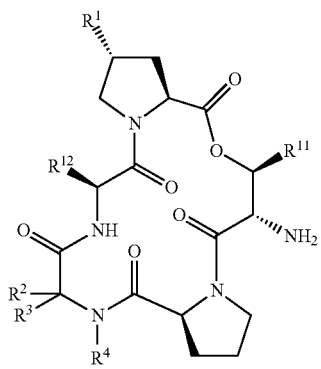

(G)

or salt thereof.

In certain embodiments, the step of deprotecting (removal of $PG^7$) involves hydrogenation, or use of hydrogen transfer conditions.

In certain embodiments, the method further comprises coupling the compound of Formula (G), or salt thereof, with a compound of Formula (H):

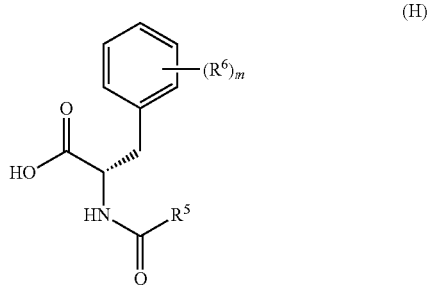

(H)

or salt thereof; to provide a compound of Formula (I) or salt thereof.

Figure 3:
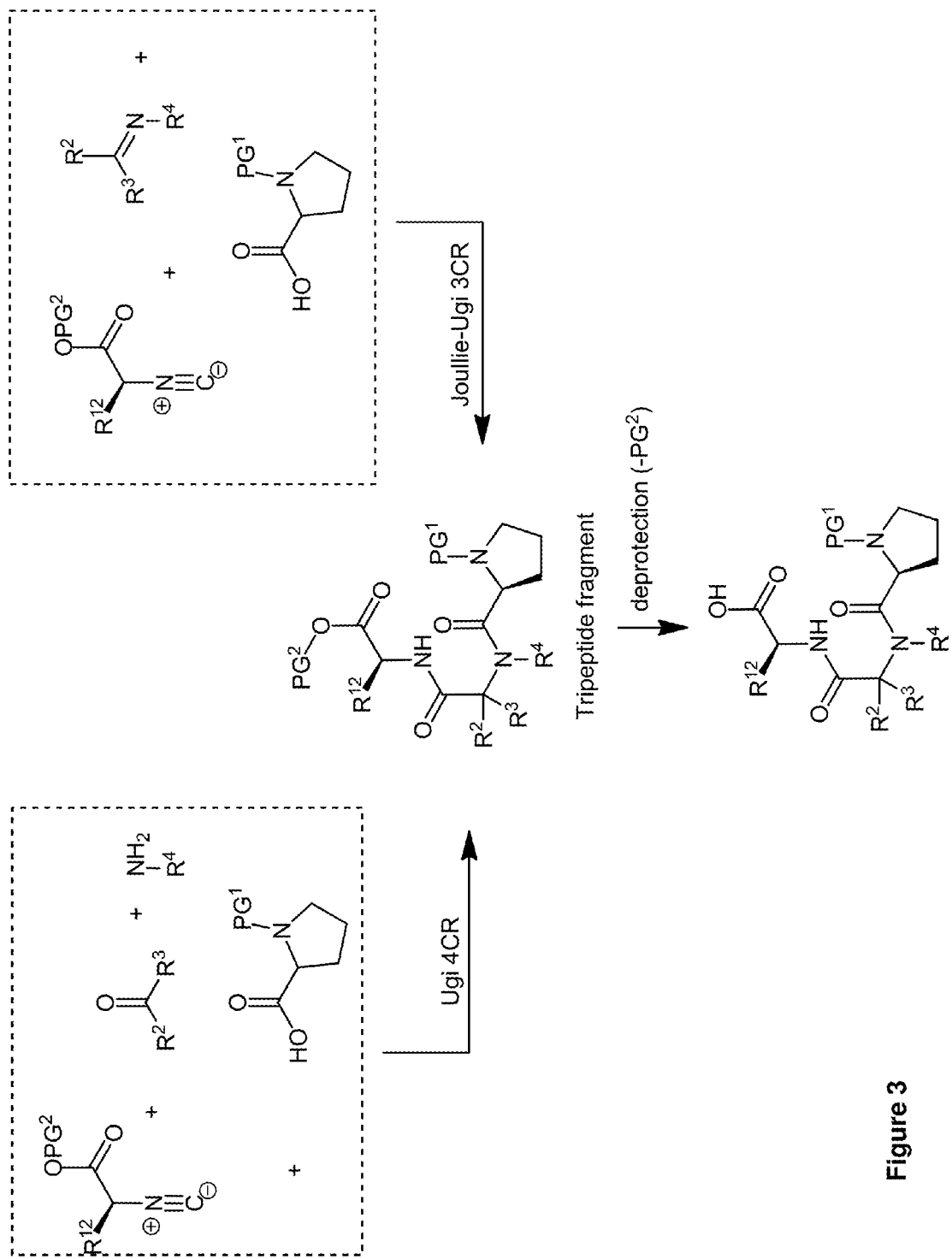
FIG. 3 depicts the two approaches used to obtain tripeptide fragments, i.e., using the Ugi four-component reaction (4CR) or the Joullié-Ugi three-component reaction (3CR).

In certain embodiments, the compound of Formula (A), or salt thereof, is prepared by a Ugi 4-component reaction or a Joulie-Ugi 3-component reaction, i.e., as depicted in FIG. 3, followed by deprotection, wherein $PG^2$ is an oxygen protecting group.

In certain embodiments, $PG^2$ is a methyl group. In certain embodiments, the step of deprotecting (removal of $PG^2$) involves basic hydrolysis (e.g., use of NaOH, LiOH).

Pharmaceutical Compositions

In certain embodiments, the present invention provides a pharmaceutical composition comprising a compound of the present invention, e.g., a compound of Formula (I) or a pharmaceutically acceptable salt thereof, and, optionally, a pharmaceutically acceptable excipient. In certain embodiments, the compound of the present invention is provided in an effective amount in the pharmaceutical composition, e.g., a therapeutically effective amount and/or a prophylactically effective amount, depending upon the intended method of treatment.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer P188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable nonirritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered. by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Still further encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Optionally, a single container may comprise one or more compartments for containing an inventive pharmaceutical composition or compound, and/or a pharmaceutically acceptable excipient for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A kit may thus comprise such multi-compartment containers providing an inventive pharmaceutical composition or compound and one or more pharmaceutically acceptable excipients.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with an additional therapeutic agent.

Methods of Use and Treatment

The present invention also provides methods of using compounds of the present invention, e.g., a compound of Formula (I) or a pharmaceutically acceptable salt thereof, as described herein.

For example, in one aspect, provided are methods of treating a microbial infection in a subject, comprising administering an effective amount of a compound of the present invention.

In another aspect, provided is a method of treating microbial virulence. Such a method can be conducted by contacting the compound of the present invention, in vivo (i.e., by administration to a subject) or in vitro (e.g., upon contact with the microorganism in a cell culture).

For example, in certain embodiments, provided is a method of treating microbial virulence comprising contacting an effective amount of the compound of the present invention with a microorganism. In certain embodiments, provided is an in vitro method of treating microbial virulence comprising contacting an effective amount of the compound of the present invention with a microorganism in a cell culture. In certain embodiments, provided is an in vivo method of treating microbial virulence comprising administering an effective amount of the compound of the present invention to a subject with a microbial infection. In certain embodiments, the compound of the present invention blocks virulence factor production. In certain embodiments, the microbial virulence is bacterial virulence, and the microorganism is a bacterium.

As used herein, a "microbial infection" refers to an infection with a microorganism, such as a fungus, bacteria or virus. In certain embodiments, the microbial infection is an infection with a fungus, i.e., a fungal infection. In certain embodiments, the microbial infection is an infection with a virus, i.e., a viral infection. In certain embodiments, the microbial infection is an infection with a bacteria, i.e., a bacterial infection. Various microbial infections include, but are not limited to, skin infections, GI infections, urinary tract infections, genito-urinary infections, sepsis, blood infections, and systemic infections.

In certain embodiments, the microbial infection is an infection with a bacteria, i.e., a bacterial infection. In certain embodiments, the compounds of the invention exhibit antibacterial activity. For example, in certain embodiments, the compound has a mean inhibitory concentration, with respect to a particular bacterium, of less than 50 µg/mL, preferably less than 25 µg/mL, more preferably less than 5 µg/mL, and most preferably less than 1 µg/mL.

Exemplary bacterial infections include, but are not limited to, infections with a gram positive bacteria (e.g., of the phylum Actinobacteria, phylum Firmicutes, or phylum Tenericutes); gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thennotogae).

In certain embodiments, the bacterial infection is an infection with a gram positive bacteria. In certain embodiments, the gram positive bacteria is a bacteria of the phylum Firmicutes. In certain embodiments, the bacteria is a member of the phylum Firmicutes and the genus *Enterococcus*, i.e., the bacterial infection is an *Enterococcus* infection. Exemplary *Enterococci* bacteria include, but are not limited to, *E. avium, E. durans, E. faecalis, E. faecium, E. gallinarum, E. solitarius, E. casseliflavus*, and *E. raffinosus*. In certain embodiments, the *Enterococcus* infection is an *E. faecalis* infection. In certain embodiments, the *Enterococcus* infection is an *E. faecium* infection.

In certain embodiments, the bacteria is a member of the phylum Firmicutes and the genus *Staphylococcus*, i.e., the bacterial infection is a *Staphylococcus* infection. Exemplary *Staphylococci* bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri*, and *S. xylosus*. In certain embodiments, the *Staphylococcus* infection is an *S. aureus* infection. In certain embodiments, the *Staphylococcus* infection is an *S. epidermis* infection.

In certain embodiments, the bacterial infection is resistant to other antibiotic therapy. For example, in certain embodiments, the bacterial infection is vancomycin resistant (VR). In certain embodiments, the bacterial infection is a vancomycin-resistant *E. faecalis* infection. In certain embodiments, the bacterial infection is a vancomycin-resistant *E. faecium* infection. In certain embodiments, the bacterial infection is a methicillin-resistant (MR). In certain embodiments, the bacterial infection is a methicillin-resistant *S. aureus* (MRSA) infection.

In yet another aspect, provided is a method of treating bacterial infection and/or virulence including the treatment of bacteria or infection caused by bacteria that are resistant to other treatments, are multi-drug tolerant or resistent and/or that neither grow nor die in the presence of or as a result of other treatments. Such a method can be conducted in vivo (i.e., by administration to a subject) or in vitro (e.g., upon contact with bacteria in a cell culture). For example, in certain embodiments, provided is a method of treating bacterial virulence comprising administering an effective amount of a compound of the present invention e.g., a compound of Formula (I) or a pharmaceutically acceptable salt thereof, to a subject with a bacterial infection. In certain embodiments, the compound blocks virulence factor production.

In another aspect, the compounds of the present invention inhibit the growth of or kill rapidly dividing cells such as stimulated inflammatory cells. Thus, the present invention also contemplates the treatment of a disease, disorder, or condition associated with abnormal cellular proliferation, such as cancer, autoimmune diseases, inflammatory diseases, and diabetic retinopathy.

Thus, in one aspect, provided is a method of treating cancer comprising administering an effective amount of the compound of the present invention or pharmaceutically acceptable salt thereof to a subject.

In another aspect, provided is a method of treating an autoimmune disease comprising administering an effective amount of the compound of the present invention or pharmaceutically acceptable salt thereof to a subject.

In yet another aspect, provided is a method of treating an inflammatory disease comprising administering the compound of the present invention or pharmaceutically acceptable salt thereof to a subject.

In yet another aspect, provided is a method of treating diabetic retinopathy comprising administering an effective amount of the compound of the present invention or pharmaceutically acceptable salt thereof to a subject.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins, etc. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutically agent is an antibiotic. Exemplary antibiotics include, but are not limited to, penicillins (e.g., penicillin, amoxicillin), cephalosporins (e.g., cephalexin), macrolides (e.g., erythromycin, clarithormycin, azithromycin, troleandomycin), fluoroquinolones (e.g., ciprofloxacin, levofloxacin, ofloxacin), sulfonamides (e.g., co-trimoxazole, trimethoprim), tetracyclines (e.g., tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline)), aminoglycosides (e.g., gentamicin, tobramycin, paromomycin), aminocyclitol (e.g., spectinomycin), chloramphenicol, sparsomycin, quinupristin/dalfoprisin (Syndercid™), In certain embodiments, the antibiotic is a ribosome-targeting antibiotic.

Antibiotics target ribosomes at distinct locations within functionally relevant sites. They exert their inhibitory action by diverse modes, including competing with substrate binding, interfering with ribosomal dynamics, minimizing ribosomal mobility, facilitating miscoding, hampering the progression of the mRNA chain, and blocking the nascent protein exit tunnel. Examples of antibiotics that reveal novel ribosomal properties or enforced otherwise observed findings include the following: decoding (paromomycin); mRNA progression (spectinomycin); A-site binding to the small (tetracycline antibiotic) and the large (chloramphenicol) subunits; PTC mobility (sparsomycin); tRNA rotatory motion (quinupristin/dalfoprisin), and tunnel gating (troleandomycin); see Yonath, *Annu. Rev. Biochem.* (2005) 74:649-679.

In certain embodiments, the ribosome-targeting antibiotic is a tetracycline antibiotic. Exemplary tetracycline antibiotics include, but are not limited to, tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline).

EXAMPLES

In order that the invention described herein may be more fully understood, the following examples are set forth. It should be understood that these examples are for illustrative purposes only and are not to be construed as limiting this invention in any manner.

Example 1. Diversity-Oriented Synthesis of Cyclic Acyldepsipeptides

In an effort to improve the pharmacological properties of the enopeptins, a research group at Bayer Pharmaceuticals carried out an intensive structure-activity-relationship (SAR) study of the enopeptins (see, e.g., Hinzen et al., *Chem Med Chem* (2006) 1:689; U.S. 20050107288). Their medicinal chemistry program was guided by the observation that the conformation of the peptidolactone core structure was constrained by two transannular hydrogen bonds to the phenylalanine moiety of the side chain. On this basis, it was anticipated that replacing the constituents of the peptidolactone with conformationally restricted amino acids would yield enopeptin derivatives with improved antibacterial activity. Although most changes in the peptidolactone decreased antibacterial activity, replacement of N-methylalanine with a rigid pipecolate moiety yielded a more potent analogue. Presumably, rigidification of the peptidolactone lowers the entropic cost of binding to the ClpP core. The stability and antibacterial activity of these rigidified enopeptin analogs were further enhanced by replacement of the exocyclic phenylalanine with 3,5-difluorophenylalanine and by substitution of the polyunsaturated side chain with a 2-heptenoyl moiety. The optimized enopeptin derivative, known as acyl depsipeptide 4 (ADEP 4), exhibited remarkable activity both in vitro and in vivo (FIG. 1). As was the case for the parent enopeptins, no cross-resistance to ADEP 4 was observed and the compound was active against multidrug resistant pathogens. The minimum inhibitory concentration (MIC) and in vivo antibacterial activity of ADEP 4 equaled or even surpassed that of established antibacterial drugs. Remarkably, mice infected with a lethal innocula of *Enterococcus faecalis* had a 100% survival rate when treated with a single dose of ADEP 4 at 0.5 mg/kg. The development of ADEP 4 clearly indicates the power of medicinal chemistry in enhancing the properties of natural products.

Figure 2:
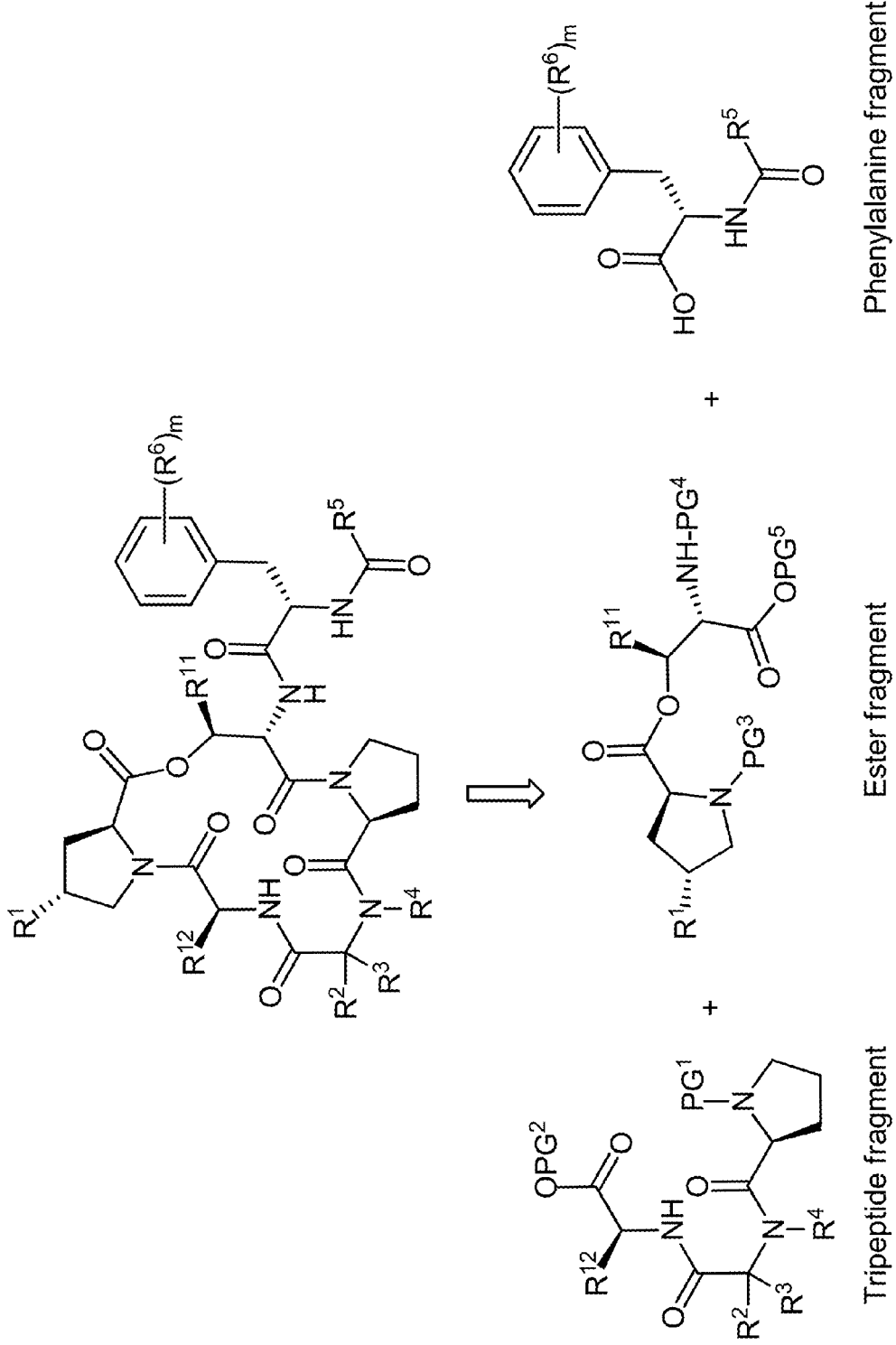
FIG. 2 depicts the retrosynthetic approach to obtain the inventive enopeptin compounds described herein.

Given the promise of ADEP 4 as an antibacterial drug, we sought to develop an efficient synthetic route to the peptidolactone core of this molecule that also allowed for the preparation of other conformationally constricted enopeptin derivatives. In the interest of expediency, we planned to capitalize on the convergent scheme used in the syntheses of ADEP 4 (and of enopeptins A and B) in which a tripeptide fragment and an ester fragment are coupled, cyclized and acylated (FIG. 2) (see, e.g., Schmidt et al., *Angew. Chem. Int. Ed. Engl.* (1997) 36:1110). Our objective was to develop an efficient and diversity-oriented synthesis of the tripeptide precursor of ADEP 4 (Ala-Pip-Pro). The published chemical synthesis of this tripeptide fragment uses standard peptide chemistry and as such is limited by three distinct steps for removal of protecting groups, a challenging acylation of a secondary amide (pipecolamide), and a dependence on commercially-available amino acids. An ideal synthesis of the tripeptide would be higher yielding, greater in atom economy, and enable facile exchange of ADEP 4's pipecolate with other conformationally rigid amino acids for SAR studies. We hypothesized that the tripeptide precursor of ADEP 4 and other conformationally restricted tripeptides could be prepared in a single step via isocyanide-based multicomponent reactions (FIG. 3) (see, e.g., Dömling et al., *Angew. Chem., Int. Ed.* (2000) 39:3168; Dömling, *Chem. Rev.* (2006) 106:17). Pipecolate containing tripeptides reminiscent of the ADEP 4 tripeptide precursor can be prepared from six-membered cyclic imines, N-Boc-proline, and an isocyanide derived from alanine methyl ester in a Joullié-Ugi three-component reaction (Joullié-Ugi 3CR) (see, e.g., Nutt et al., *J. Am. Chem. Soc.* (1982) 104:5852; Nenajdenko et al., *Tetrahedron.* (2006) 62:5922). Similarly, peptides with conformationally restricted N-methyl, α,α-disubstituted amino acids can be prepared with an Ugi four-component reaction (Ugi 4CR) from methylamine, various ketones, N-Boc-proline, and an isocyanide derived from alanine methyl ester (see, e.g., Simila et al., *Tetrahedron Lett.* (2008) 49:4501).

This Example describes a diversity-oriented synthesis of the tripeptide fragment featuring isocyanide-based multicomponent reactions that enabled the preparation of eight enopeptin derivatives. The antibacterial activity of these analogues against clinical isolates of methicillin-sensitive *S. aureus* (MSSA), methicillin-resistant *S. aureus* (MRSA), vancomycin-susceptible *E. faecalis* and vancomycin-resistant *E. faecium* (VRE) was systematically assessed. Additionally, we report for the first time the minimum bactericidal concentration (MBC) of any enopeptin derivatives. It is noteworthy that a novel ADEP 4 derivative with 4-methyl pipecolate in place of pipecolate has considerably enhanced activity against pathogenic *Enterococci*.

Synthesis and Elaboration of the ADEP 4 Peptidolactone Core Structure

Figure 4A:
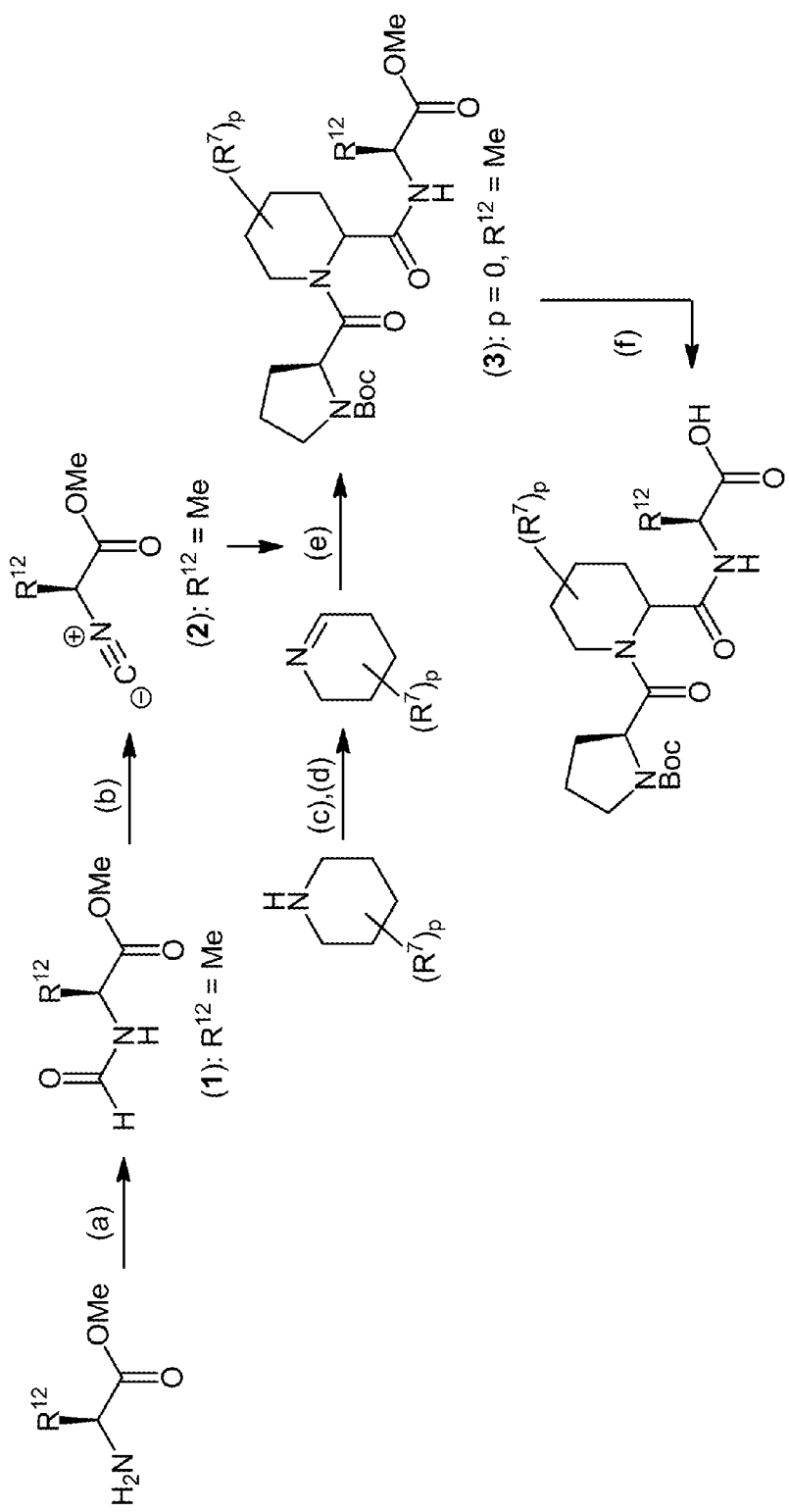
FIGS. 4A-4C depict the synthetic approach to provide pipecolate-derived enopeptin compounds.
Figure 4B:
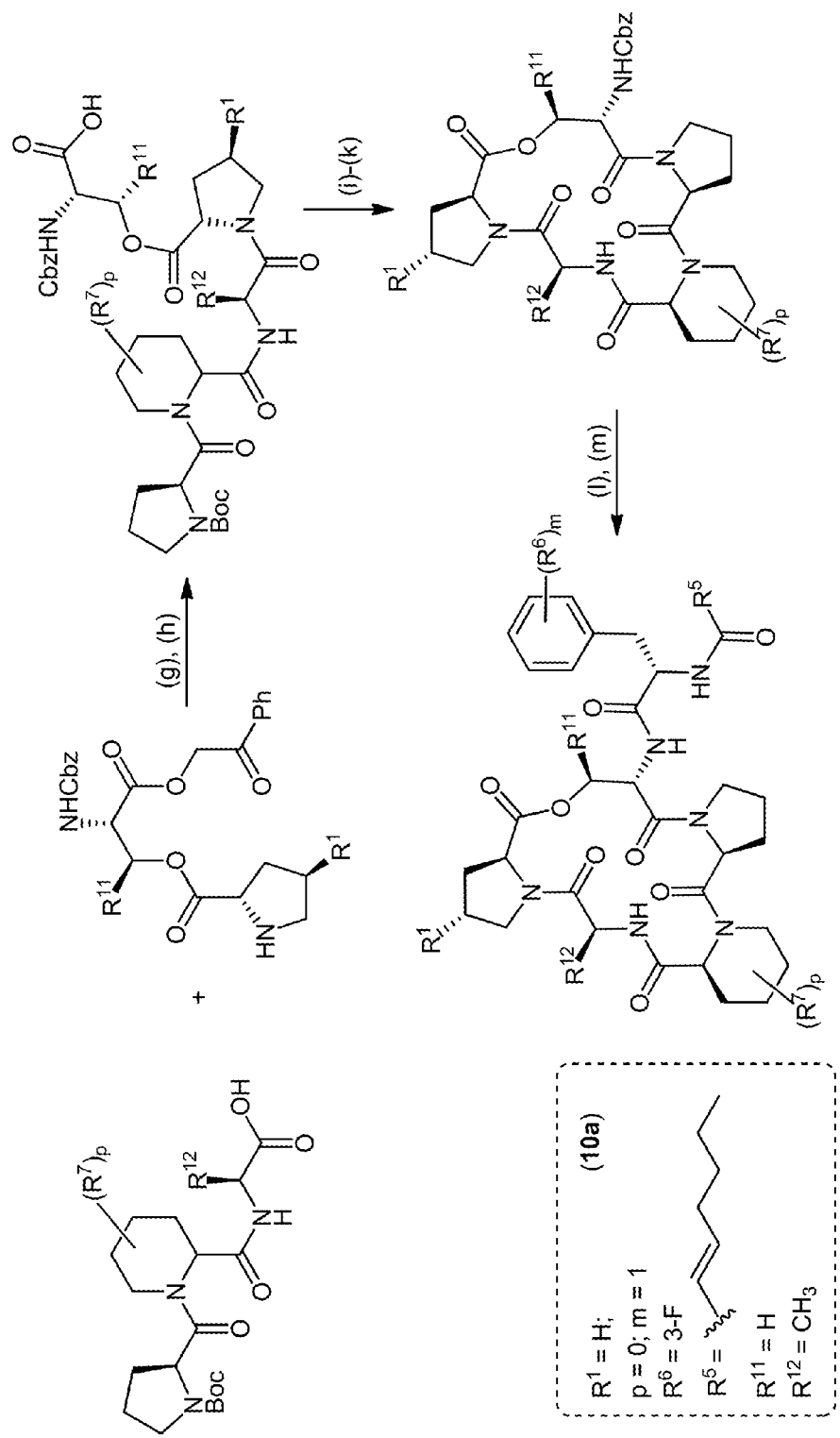

Our initial objective was to prepare 10a, a more synthetically accessible analogue of ADEP 4 in which 4-methylproline is replaced by proline and 3,5-difluorophenylalanine is replaced by 3-fluorophenylalanine (FIGS. 4A-4B). In analogy to the published synthesis of ADEP 4, our plan was to prepare 10a in a convergent fashion. We anticipated that the requisite tripeptide fragment could be synthesized via a Joullié-Ugi 3CR (FIG. 4A). The substrates of the reaction were N-Boc proline, dehydropiperidine, and an isocyanide derived from alanine methyl ester. While N-Boc proline was commercially available, the other two substrates had to be chemically synthesized. The isocyanide was prepared via the N-formylation and dehydration of alanine methyl ester under racemization-free conditions described in the literature (see, e.g., Zhu et al., *Tetrahedron Lett.* 2008, 50, 577). N-formyl-L-alanine methyl ester was synthesized from L-alanine methyl ester hydrochloride accordingly to literature procedures for the preparation of amino acid tert-butyl esters (see, e.g., Waki et al., *J. Org. Chem.* 1977, 42, 2019). Dicyclohexylcarbodiimide (DCC) activation of formic acid as the O-acylisourea derivative followed by the addition of the amino acid ester provided the desired N-formyl product 1 in good yield. Dehydration of 1 to form the isocyanide (2) was effected by triphosgene in the presence of N-methylmorpholine (NMM) (Zhu, supra). Synthesis of the isocyanide was realized in 69% yield over two steps. Chiral GC-MS analysis of the isocyanide product revealed that no racemization of the amino acid occurred during the formylation and dehydration.

We envisioned that the cyclic imine substrate of the Joullie-Ugi reaction could be prepared by halogenation and dehydrohalogenation of piperidine (FIG. 4A). N-chlorination of piperidine via in situ generation of tert-BuOCl gave the desired product in quantitative yield (Waki, supra). Dehydrohalogenation of the N-chloropiperidine was effected by sodium methoxide in methanol (Nutt, supra). Due to its instability, the crude dehydropiperidine was directly used in a Joullié-Ugi 3CR with N-Boc-proline and the isocyanide derived from alanine methyl ester (2) (see, e.g., Zhong et al., *Tetrahedron Lett.* 2005, 46, 1099; Davis et al., *Org. Lett.* 2002, 4, 103). After stirring for five days at room temperature, the expected tripeptide methyl ester, 3, was isolated in 76% yield. Analytical HPLC analysis of saponified 3 (LiOH, 1:1 THF:H$_2$O, quantitative yield) revealed that its diastereomeric ratio was 70:30. Based on the retention time of an authentic standard [(S)-Boc-Pro-(S)-Pip-(S)-Ala-COOH], we determined that the desired tripeptide was the minor diastereomer. The basis of the diastereoselectivity of this reaction is not clear and is under investigation. In spite of the undesirable stereoselectivity, the yield and the atom economy of the one-pot Joullié-Ugi 3CR make it a viable alternative to standard peptide chemistry for synthesis of the ADEP 4 tripeptide precursor.

The diastereomeric mixture of tripeptide products were saponified and carried forward to prepare the desired peptidolactone using the convergent synthetic route described in the literature (FIG. 4B) (see, e.g., Hinzen, supra; U.S. 20050107288). In contrast to the reported synthesis of ADEP 4, the diastereomeric peptidolactones were chromatograpically separated and acylated with N-2-heptenoyl, 3-fluorophenylalanine to yield 10a and its diastereomer 10b. Diversity-Oriented Synthesis of Cyclic Acyldepsipeptides with Conformationally Constrained Amino Acids.

In addition to the efficiency with which an isocyanide-based multicomponent reaction could be used to synthesize a tripeptide, a major consideration in the selection of this reaction type was its applicability in the preparation of structurally diverse peptides. Rather than preparing a random collection of tripeptides, we sought to synthesize tripeptides that were more conformationally constrained than the tripeptide precursor of ADEP 4. Our utilization of conformationally constrained amino acids was an extension of the findings of the Bayer research group wherein replacement of the N-methylalanine moiety of the natural enopeptins with pipecolate yielded the enopeptin derivative ADEP4 with enhanced antibacterial activity (see, e.g., Hinzen, supra; U.S. 20050107288).

Figure 4C:
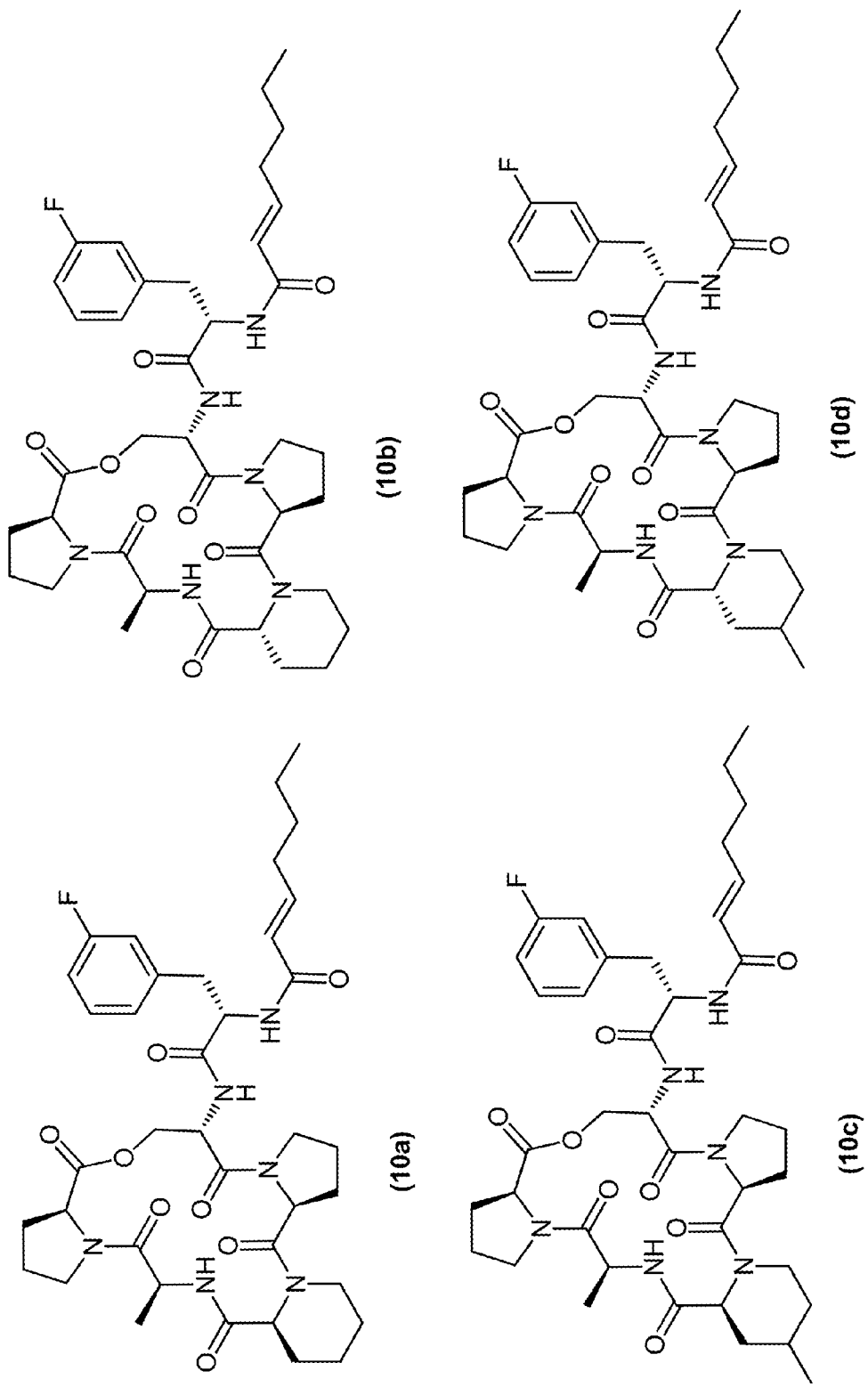

Our first synthetic target was an analog of the ADEP 4 tripeptide fragment with a substituent on the pipecolate moiety. Based on the principles of conformational analysis, we predicted that strategic placement of a substituent on the ring would increase the inversion barrier of pipecolate (see, e.g., Eliel, E; Wilen S. H. *Stereochemistry of Organic Compounds*; John Wiley and Sons: New York, 1994, Chapter 11). In particular, a substituent on the 4-position of pipecolate would be especially rigidifying since ring inversion would result in a strongly disfavored 1,3-diaxial interaction between ring substituents. To prepare such a compound, we carried out a Joullié-Ugi 3CR with N-Boc-proline, the isocyanide derived from alanine methyl ester (2), and dehydro 4-methyl piperidine (FIG. 4A). The latter compound was prepared in an analogous manner to dehydropiperidine. Interestingly, the dehydro-4-methylpiperidine was a better substrate in the Joullié-Ugi 3CR, yielding the expected tripeptide methyl ester in 84% in a reaction time of only 2 days. Analytical HPLC analysis of the saponified product revealed that its diastereomeric ratio was 70:30. As the retention time of the minor diastereomer was very similar to that of the authentic ADEP 4 tripeptide precursor, we deduced that it was the desired diastereomer containing (2S,4R)-4-methylpipecolamide. The mixture of diastereomeric peptides was carried forward in the aforementioned scheme for convergent synthesis of the peptidolactone core structure. The diastereomeric peptidolactones were chromatographically separated and acylated with N-2-heptenoyl, 3-fluorophenylalanine to yield the desired compound, 10c (FIG. 4C).

Figure 5A:
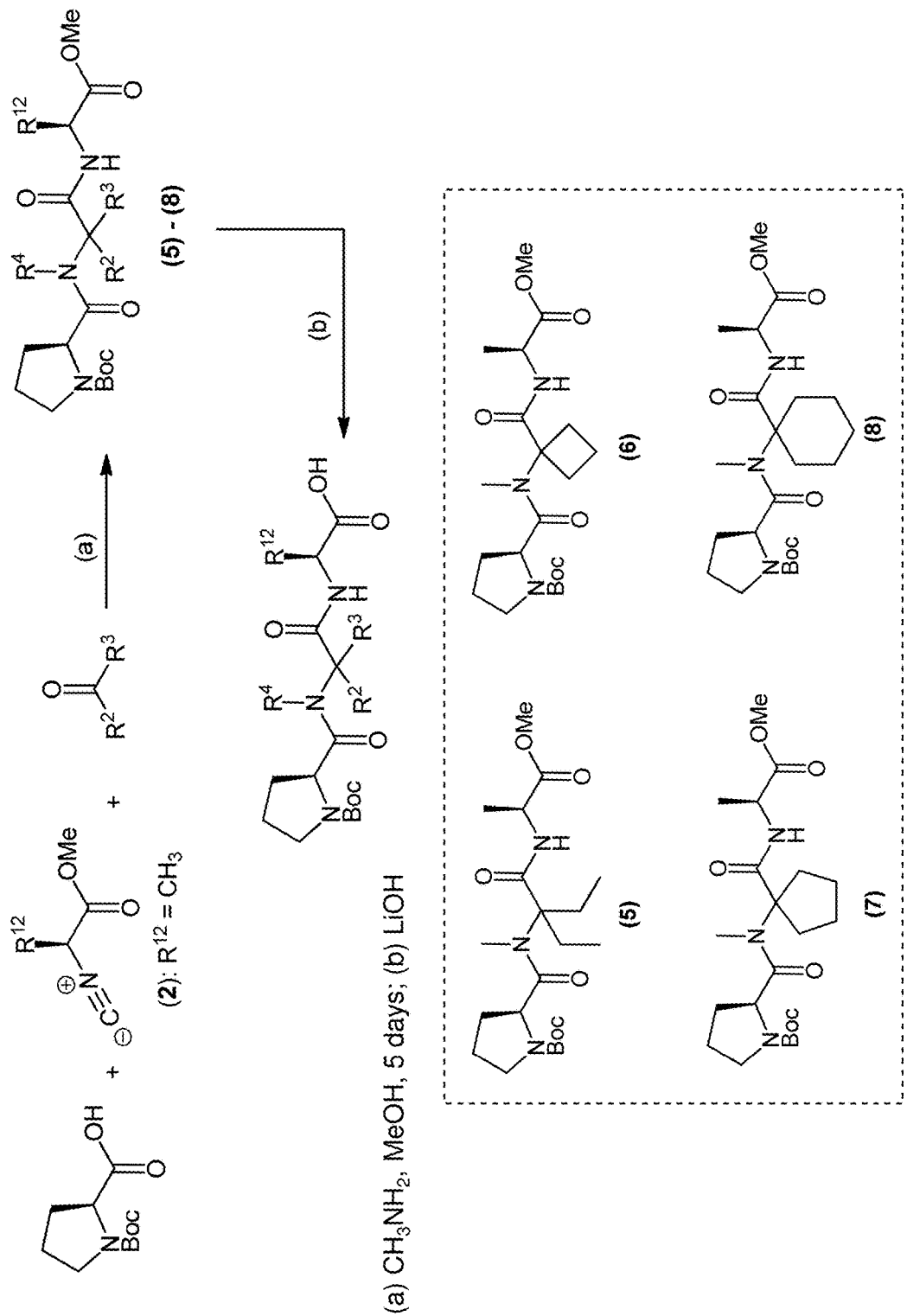
FIGS. 5A-5C depict the synthetic approach to provide α,α-disubstituted amino acid-derived enopeptin compounds.
Figure 5B:
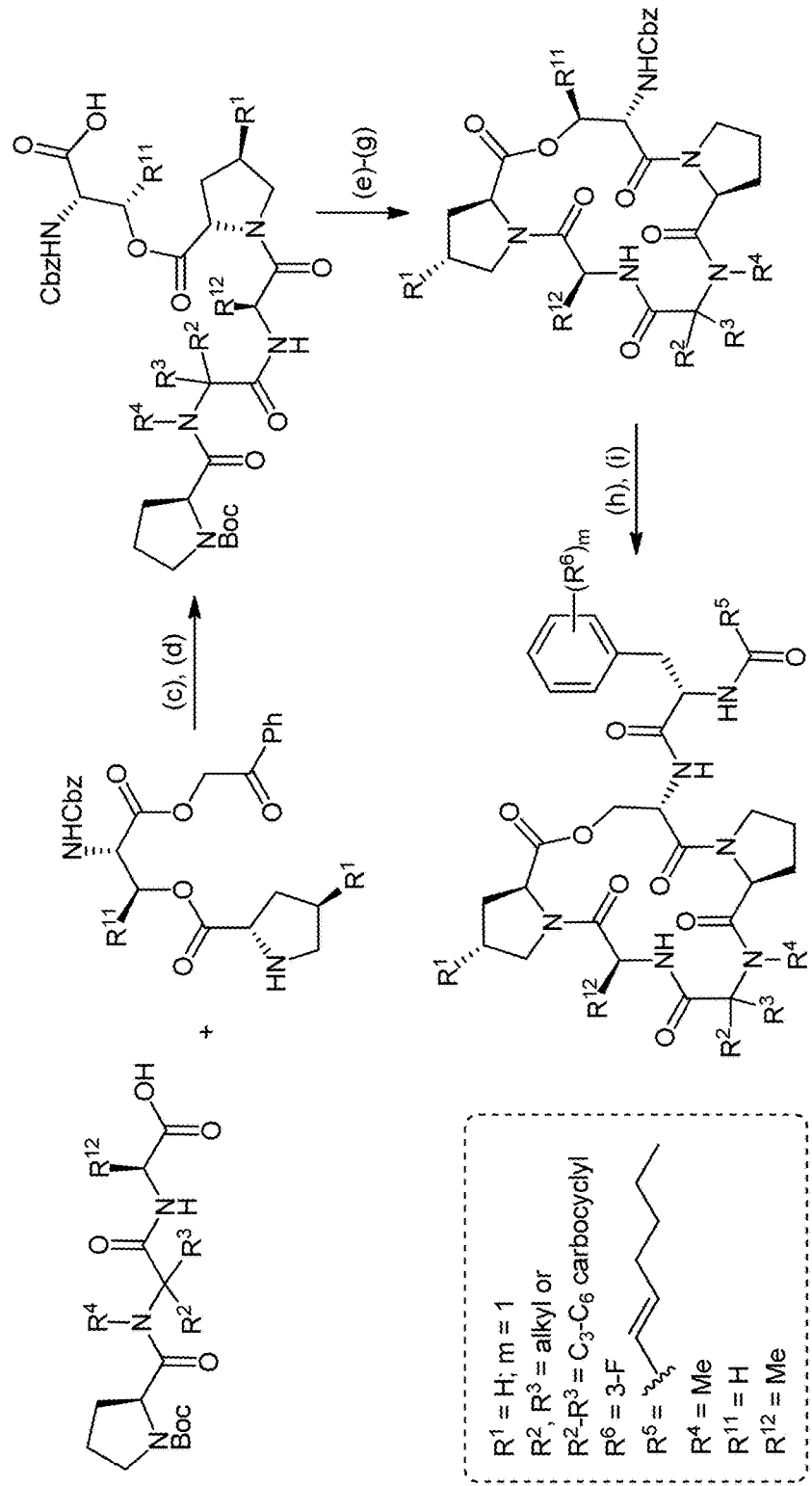
Figure 5C:
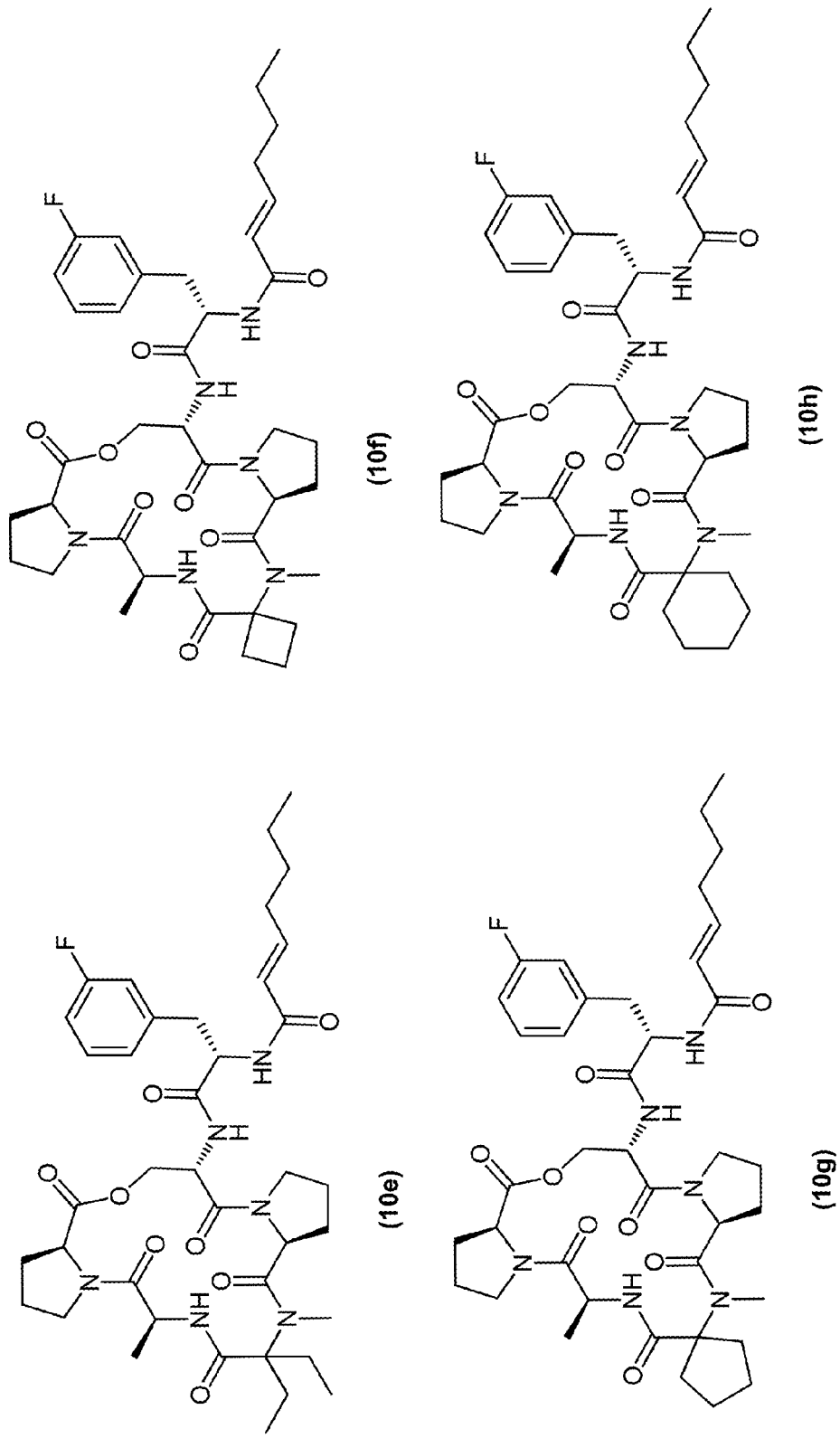

Our other synthetic targets were tripeptides containing α,α-disubstituted amino acids (FIGS. 5A-5C). These amino acids, while of limited commercial availability, are known to limit the conformation of peptides (see, e.g., Karle et al., Biochemistry. 1990, 29, 6747; Marshall et al., Proc. Natl. Acad. Sci. USA. 1990, 87, 487). We suspected that the desired tripeptides could be prepared from methylamine, N-Boc-proline, the isocyanide derived from L-alanine methyl ester (2), and various ketones in an Ugi 4CR. To avoid mixtures of diastereomeric products, we used symmetric ketones (i.e., 3-pentanone, cyclobutanone, cylopentanone, and cyclohexanone) as substrates (FIG. 5A). The reactants were stirred in MeOH for a period of 1-5 days to optimize reaction conditions. Products 5-8 were isolated in good to excellent yields. The results are summarized in Table 1. Good yields of the tripeptides were only observed with reaction times >4 days and reaction concentrations ≥1.9 M. Increasing the reaction temperature of a model reaction with cyclopentanone and methylamine to 50° C. did not significantly improve the reaction yield. Using four different ketones as substrates in the Ugi 4CR, we were able to prepare four different tripeptide methyl esters (5-8) (FIG. 5A). Those products were saponified as previously described to yield the requisite tripeptides. The tripeptides prepared via the Ugi 4CR were used in the aforementioned convergent synthesis to yield enopeptin derivatives, 10e-h (FIGS. 5B-5C).

TABLE 1

Optimized Ugi 4CR conditions for symmetric ketones

| Ugi Product | R | n | Conc. (M) | Temp. (° C.) | Time (d) | Yield (%) |
|---|---|---|---|---|---|---|
| 5 | $CH_3$ | 0 | 1.90 | 25 | 5 | 75 |
| 6 | H | 1 | 1.90 | 25 | 5 | 93 |
| 7 | H | 2 | 0.65 | 25 | 5 | 62 |
| 7 | H | 2 | 1.90 | 25 | 5 | 78 |
| 8 | H | 3 | 1.90 | 25 | 5 | 90 |

The naturally occurring enopeptins and the synthetic derivative ADEP 4 are reported to have strong antibacterial activity (see, e.g., Hinzen et al., Chem Med Chem 2006, 1, 689). Broth dilution assays were used to determine the MICs of the acyldepsipeptide derivatives 10a-h against both ATCC strains and clinical isolates of S. epidermis, S. aureus, and Enterococci obtained from patients of the Veterans Affairs Medical Center in Providence, R.I. Clinical isolates were included to gain a better indication of the potential of these new antibacterial agents (see, e.g., Clinical and Laboratory Standard Institute (CLSI) Methods for dilution antimicrobial susceptibility tests for bacteria that grow aerobically M07-A8; CLSI 8th ed., Wayne, Pa., 2009; Clinical Laboratory Standards Institute (CLSI) Performance standards for antimicrobial susceptibility testing M100-S19. CLSI 19th informational suppl., Wayne, Pa. 2009). In the interest of assessing the cell-killing ability of these compounds, the minimal bactericidal concentrations (MBC) of the compounds was also determined against the aformentioned strains. The MIC was defined as the lowest concentration of an antimicrobial agent visually inhibiting more than 99% of the colonies. The MBC was defined as the lowest antibiotic concentration to show no growth (99.9% kill) after 24 h of incubation.

Compound 10a, an analog of ADEP 4, exhibited the expected antibacterial activity against drug-resistant, pathogenic S. aureus strains. All synthetic acyldepsipeptides in which the pipecolate moiety was replaced by α,α-disubstituted amino acids lacked antibacterial activity. In contrast, compound 10c, which 4-methylpipecolate in place of pipecolate, had better activity than compound 10a against MSSA. Compound 10a was also evaluated against Staphylococcus epidermis (ATCC 25984) and showed an MIC of 1.25 µg/mL and an MBC of 1.25 µg/mL.

TABLE 2

Biological activity of synthetic acyldepsipeptides vs. S. aureus (µg/mL)

| | MSSA | | MRSA | |
|---|---|---|---|---|
| | MIC | MBC | MIC | MBC |
| 10a | 1.25 | 1.25 | 1.25 | 1.25 |
| 10b | >312 | >312 | >312 | >312 |
| 10c | 0.6 | 0.6 | 0.6 | 2.4 |
| 10d | >156 | >156 | >156 | .156 |
| 10e | 78.1 | >312 | >312 | >312 |
| 10f | 312 | >312 | >312 | >312 |
| 10g | 39.1 | >312 | >312 | >312 |
| 10h | 39.1 | >312 | >312 | >312 |

MSSA = Methicillin-susceptible S. aureus (ATCC 35556)
MRSA = Methicillin-resistant S. aureus (clinical isolate from blood)

Based on the activities of compounds 10a and 10c against the S. aureus strains, they were selected for further evaluation against a panel of pathogenic Enterococci. Remarkably, compound 10c exhibited more potent activity against E. faecalis and vancomycin-resistant E. faecium than compound 10a.

TABLE 3

Biological activity of synthetic acyldepsipeptides vs. Enterococci (µg/mL)

| | EF[1] | | EF[2] | | VRE[3] | | VRE[4] | |
|---|---|---|---|---|---|---|---|---|
| | MIC | MBC | MIC | MBC | MIC | MBC | MIC | MBC |
| 10a | 0.16 | 1.25 | 0.04 | 0.04 | 0.08 | 0.08 | 0.04 | 0.04 |
| 10c | 0.04 | 0.08 | 0.02 | 0.04 | 0.04 | 0.08 | 0.04 | 0.04 |

[1] = Enterococcus faecalis (ATCC 29212)
[2] = Enterococcus faecalis (clinical isolate from rectal swab)
[3] = Vancomycin-resistant Enterococcus faecium (clinical isolate obtained from tissue)
[4] = Vancomycin-resistant Enterococcus faecalis (clinical isolate from rectal swab)

Experimental

All amino acids and peptide coupling reagents were purchased from NovaBiochem. Additional chemicals were purchased from Sigma-Aldrich unless otherwise stated. A Biotage Initiator microwave reactor was used. GC-MS analysis was performed on a Hewlett Packard 5971A GC-MS system using an HP5-MS column and helium as the carrier gas. Splitless injections of 1 mL were made using an initial temperature of 60° C., holding 2 min, then 20° C./min ramp to 280° C., and holding 2 min. Chiral GC-MS was performed on a Hewlett Packard G1800C instrument equipped with a Varian CP-Chirasil-DEX 25 m×0.32 mm column. Low-resolution analytical LC-MS was performed in the positive ion mode on a Thermo LCQ Deca XP MAX high sensitivity MS" ion trap mass spectrometer with a Shimadzu HPLC system using a Waters X-Terra MS $C_{18}$ column (2.5 µm, 2.1×50 mm). The method consisted of 5-95% MeCN in $H_2O$+0.1% TFA over 15 min. The flow rate was 0.2 mL/min. High-resolution mass analyses were performed on a JOEL JMS-600H double focusing magnetic sector mass spectrometer using FAB ionization. NMR analyses were performed on a Bruker Avance Ultrashield spectrometer (400 MHz for $^1$H, 100 MHz for $^{13}$C). All spectra were referenced to residual solvent signals in CDCl$_3$ (7.24 ppm for $^1$H, 77.0 ppm for $^{13}$C.)

Preparation of Substrates for Multicomponent Reactions.

N-formyl-L-alanine methyl ester (1):

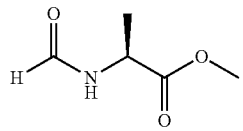

Dicyclohecylcarbodiimide (DCC) (10 g, 48.5 mmol) was dissolved in 50 mL of DCM and cooled to 0° C. for 5 min. 96% formic acid (2.6 mL, 69 mmol) was added slowly. In a separate flask, L-alanine methyl ester HCl salt (5 g, 36 mmol) was dissolved in 25 mL dichloromethane (DCM) with 7 mL NMM+1 g of DMAP. The contents of this flask were added to the DCC-formic acid mixture at 0° C. and the reaction allowed to warm to room temperature overnight with stirring. The majority of the solvent was removed in vacuo until a viscous slurry was obtained. This slurry was vacuum filtered through silica gel and the residue was washed with 25 mL DCM to ensure complete elution of product. The filtrate was concentrated in vacuo and loaded on a 75×50 mm Si gel resin bed and eluted with 4:1 EtOAc:hexanes. Yield: 3.4 g (72.1%), clear oil, R$_f$=0.6 (4:1 EtOAc:hexanes), stains white with p-anisaldehyde. $^1$H NMR (CDCl$_3$) 8.14 (1H, s), 6.43 (1H, bs), 4.54 (1H, m), 3.72 (3H, s), 1.39 (3H, d, J=7 Hz). $^{13}$C NMR (CDCl$_3$) 173.0, 160.5, 52.6, 46.7, 18.4. MS (EI, m/z): 131.0 [M]$^+$ for C$_4$H$_9$NO$_2$.

Isocyanide derived from alanine methyl ester (2):

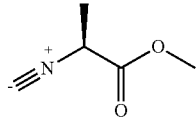

N-formyl-L-alanine methyl ester (1) (2.2 g, 16.8 mmol) was dissolved in 50 mL anhydrous DCM and solution cooled to −78° C. In a separate, dry, pear shaped flask was added triphosgene (1.7 g, 5.7 mmol) and 7 mL dry DCM. If the triphosgene begins to bubble during the addition of DCM discard it carefully, as it has become wet. The triphosgene solution was added slowly to the N-formyl amino acid ester. Then 3.6 mL (33 mmol) N-methylmorpholine (NMM) added slowly over 10 min. The reaction was stirred for 1.5 h at −78° C. then quenched with 22 mL deionized water by placing a vent needle in the septa and allowing the stirring solution to warm to room temperature. The resulting mixture was partitioned and the water layer washed with an additional 50 mL DCM. The organic fraction was collected, dried over Na$_2$SO$_4$, and solvent removed in vacuo. Crude product was loaded on a 75×50 mm Si gel resin bed and eluted with 4:1 hexanes:EtOAc (R$_f$=0.65, Iodine/Si stain). Pale yellow oil, Yield: 1.8 g (95%). $^1$H NMR (CDCl$_3$) 4.32 (1H, q), 3.81 (3H, s), 1.63 (3H, d, J=8 Hz). $^{13}$C NMR (CDCl$_3$) 167.3, 159.0, 60.0, 51.3, 19.3. MS (EI, m/z): 113.0 [M]$^+$ for C$_5$H$_7$NO$_2$.

N-chloropiperidine: 5.8 mmol (0.55 mL) of tert-BuOH, 11.7 mmol (1.39 mL) piperidine were added to 30 mL MTBE and stirred at 0° C. 11.8 mmol (23.5 mL) cleaning bleach and 11.8 mmol (0.68 mL) of acetic acid were added together slowly and reaction mixture was stirred at 0° C. for 30 min. Reaction mixture was then quenched with 15 mL of water, extracted with 20 mL MTBE, and the organic layer was washed with brine and dried with Na$_2$SO$_4$. Evaporation of solvent under reduced pressure gave the desired product 1.4 g (10.5 mmol, 89% yield) as a pale yellow oil. R$_f$=0.9 (3:1 EtOAc:hexanes) MS (EI, m/z): 119.1 [M]$^+$ for C$_5$H$_{10}$NCl.

Dehydropiperidine: 10.5 mmol (1.4 g) of N-chloropiperidine was dissolved in 3.5 mL (5.71 mmol) of 25% by wt NaOMe in MeOH. The reaction was stirred for 10 min. under N$_2$, after which a white precipitate of NaCl was formed and the reaction was complete.

Synthesis of N-2-heptenoyl-3-fluorophenylalanine-COOH (9):

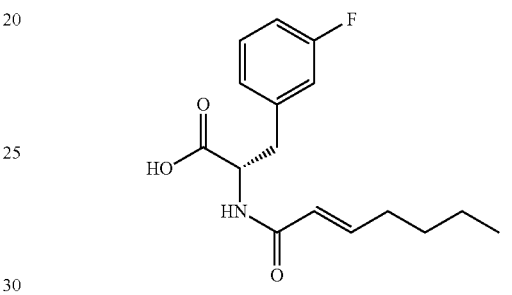

N-Boc-L-3-fluorophenyl-L-alanine (500 mg, 1.76 mmol) and NaHCO$_3$ (300 mg, 3.6 mmol) were dissolved in 10 mL DMF. MeI (1 mL, 16 mmol) was added dropwise and the mixture stirred for 24 h. Reaction mixture was then partition in 25 mL EtOAc 25 mL 0.1N HCl and 25 mL brine, then dried over Na$_2$SO$_4$ and concentrated in vacuo. Yield: 500 mg (1.68 mmol, 96%). N-Boc-L-3-fluorophenyl-L-alanine methyl ester product (500 mg, 1.7 mmol) was dissolved in 6.75 mL DCM and 4.3 mL 9:1 TFA:H$_2$O added at 0° C. Reaction was allowed to warm up to room temperature and stirred for 2 h 2×100 mL toluene successively added and removed in vacuo. Yield: 510 mg of TFA salt of L-3-fluorophenyl-L-alanine methyl ester (1.63 mmol, 93%). The product (650 mg, 2.09 mmol) was dissolved in 25 mL dry DCM and 3 mL DIEA added and was added to a separate flask containing HATU (1.14 g, 3 mmol) and trans-2-heptenoic acid (350 µL, 2.6 mmol) in 15 mL DCM and the mixture stirred overnight. The reaction mixture was then washed with 30 mL 0.1N HCl, dried over Na$_2$SO$_4$ and concentrated under vacuum, then purified by flash Si gel chromatography with 1:1 EtOAc:hexanes as eluent. R$_f$=0.95 (1:1 EtOAc:hexanes). N-2-heptenoyl-3-fluorophenylalanine methyl ester (400 mg, 1.3 mmol) was dissolved in 4 mL 1:1 THF:H$_2$O, then LiOH.H$_2$O (149 mg, 3.55 mmol) added and reaction stirred for 30 min. 1N HCl was added to adjust the pH to 1, THF removed under vacuum and the resulting aqueous layer extracted with 2×20 mL EtOAc, which was then dried with Na$_2$SO$_4$ and concentrated under vacuum. Yield: 400 mg (100%) of 9. $^1$H NMR (CDCl$_3$) 7.18 (1H, m), 6.88 (4H, m), 6.37 (1H, d, J=8 Hz), 5.77 (1H, d, J=16 Hz), 4.91 (1H, d, J=8 Hz), 3.22 (1H, m) 3.12, (1H, m), 2.13 (2H, m), 1.33 (4H, m), 0.86, (3H, m). $^{13}$C NMR (CDCl$_3$, mixture of rotamers) 174.2, 167.0, 164.1, 161.7, 147.5, 138.5, 130.3, 125.4, 122.7, 116.6, 114.4, 53.7, 37.1, 32.0, 30.2, 22.3, 13.9. HRMS (FAB): calcd for C$_{16}$H$_{20}$NO$_3$FNa [M+Na]$^+$ 316.1325, obsd 316.1306 (Δ=6.0 ppm).

Procedure for the Joullié-Ugi 3CR

The crude cyclic imines, 4 mL dry MeOH and N-Boc-L-proline (1.95 g, 8.5 mmol) were added directly to the reaction mixture, and were stirred for 15 min. The isocyanide 2 (780 mg, 6.9 mmol) was added, and the reaction stirred for 2-5 days. Solvent was removed under vacuum and crude mixture was purified on a Si gel column with 7:3 EtOAc:hexanes eluent.

Diastereomeric ratio determinations of the saponified Joullié-Ugi 3CR products were determined using a Haisil-100 C18 column (5 micron, 150 mm×4.6 mm). The flow rate was 1.5 mL/min. The method consisted of 20-65% MeCN in $H_2O$+0.1% TFA over 20 min. The detector was set to 214 nm. The retention times of the diastereomeric products were 7.63 and 8.58 min. The retention time of authentic N-Boc-L-Pro-L-Pip-L-Ala-COOH prepared according to the literature was 7.65 min (US 2005/0107288).

N-Boc-Pro-pipecolate-Ala-OMe (3):

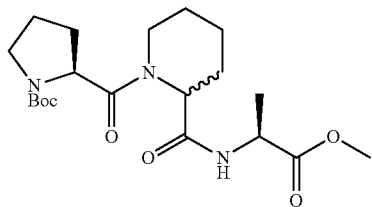 [SMILES: COC(=O)[C@H](C)NC(=O)C1CCCCN1C(=O)[C@@H]1CCCN1C(=O)OC(C)(C)C]

Yield: 2.16 g (5.2 mmol, 76%). $R_f$=0.3 (7:3 EtOAc:hexanes) $^1$H NMR (CDCl$_3$, mixture of diasteromers) 8.45 (d, 0.5H), 7.38, (d, 0.5H), 4.52 (m, 1H), 4.48 (m, 1H), 4.42 (m, 1H), 3.85 (d, 0.5H), 3.67 (s, 3H), 3.44 (1H, m), 3.40 (1H, m), 2.45 (1H, m), 2.08 (2H, m), 1.87 (3H, m), 1.64 (2H, m) 1.35 (12H, s), 0.99 (m, 2H). $^{13}$C NMR (CDCl$_3$): 173.3, 172.1, 170.0, 154.4, 79.6, 55.4, 52.0, 49.9, 48.1, 46.7, 43.4, 39.4, 34.4, 29.3, 28.0 (3C), 25.7, 24.5, 20.3, 16.6. HRMS (FAB): calcd for $C_{20}H_{33}N_3O_6Na$ [M+Na]$^+$ 434.2267, obsd 434.2267 (Δ=5.8 ppm).

N-Boc-Pro-4-methylpipecolate-Ala-OMe (4):

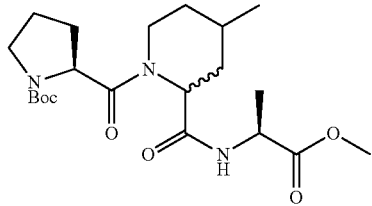 [SMILES: COC(=O)[C@H](C)NC(=O)C1CC(C)CCN1C(=O)[C@@H]1CCCN1C(=O)OC(C)(C)C]

Yield: 2.47 g (5.8 mmol, 84%). $R_f$=0.3 (7:3 EtOAc:hexanes) $^1$H NMR (CDCl$_3$, mixture of diasteromers): 8.39 (d, 0.5H), 7.28, (d, 0.5H), 4.55 (m, 1H), 4.48 (m, 1H), 4.40 (m, 1H), 3.85 (d, 0.5H), 3.65 (s, 3H), 3.49 (1H, m), 3.41 (1H, m), 2.43 (1H, m), 2.05 (2H, m), 1.83 (3H, m), 1.64 (2H, m) 1.38 (12H, s), 0.99 (m, 2H), 0.85 (3H, d). $^{13}$C NMR (CDCl$_3$): 173.4, 172.1, 170.1, 154.6, 79.8, 56.4, 52.2, 48.5, 47.0, 43.4, 34.4, 33.1, 29.5, 29.4, 28.4 (3C), 27.1, 24.9, 21.8, 16.9. HRMS (FAB): calcd for $C_{21}H_{35}N_3O_6Na$ [M+Na]$^+$ 448.2424, obsd 448.2406 (Δ=4.1 ppm).

Procedure for the Ugi 4CR

Ketones (9.48 mmol) was added to a solution of 40% methylamine in MeOH (4.75 mL, 9.48 mmol) and allowed to precondense for 1.5 h. N-Boc-L-proline (2.04 g, 9.48 mmol) added and resulting mixture stirred for 15 min., then isocyanide derived from L-alanine methyl ester (1.08 g, 9.48 mmol) was added. Reaction was left to stir for 5 days at room temperature, then concentrated in vacuo. Crude product was loaded onto a 80 mm×50 mm Si gel resin bed and eluted with 7:3 EtOAc:hexanes.

3-Pentanone Ugi Tripeptide (5):

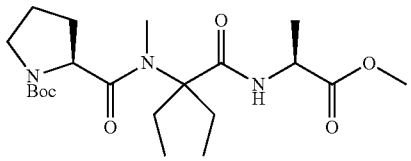 [SMILES: CCC(CC)(C(=O)N[C@@H](C)C(=O)OC)N(C)C(=O)[C@@H]1CCCN1C(=O)OC(C)(C)C]

Yield 3.03 g (7.11 mmol, 75%). $R_f$=0.25 (7:3 EtOAc:hexanes), stains white with p-anisaldehyde. $^1$H NMR (CDCl$_3$, mixture of rotamers) 6.35 (1H, d), 4.59 (1H, m), 3.70 (3H, s), 3.50 (1H, m), 3.45 (1H, m), 3.08 (3H, s), 2.23 (2H, m), 2.10 (2H, m), 1.85 (4H, m), 1.48 (3H, d), 1.38 (9H, s), 0.87 (3H, m) 0.78 (3H, m). $^{13}$C NMR (CDCl$_3$, mixture of rotamers) 173.9, 173.6, 172.9, 157.1, 154.7, 79.6, 68.7, 68.2, 58.0, 57.7, 52.0, 50.5, 48.5, 46.9, 32.5, 29.2, 28.5 (3C), 26.1, 24.2, 24.0, 17.7. HRMS (FAB): calcd for $C_{21}H_{37}N_3O_6Na$ [M+Na]$^+$ 450.2580, obsd 450.2566 (Δ=3.1 ppm).

Cyclobutanone Ugi Tripeptide (6):

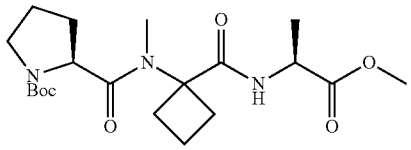 [SMILES: COC(=O)[C@H](C)NC(=O)C1(N(C)C(=O)[C@@H]2CCCN2C(=O)OC(C)(C)C)CCC1]

Yield: 3.62 g (8.81 mmol, 93%). $R_f$=0.25 (7:3 EtOAc:hexanes), stains white with p-anisaldehyde. $^1$H NMR (CDCl$_3$, mixture of rotamers) 7.65 (1H, d), 4.42 (2H, m), 3.52 (3H, s), 3.45 (1H, m), 3.40 (1H, m), 2.87 (3H, s), 2.54 (4H, m), 2.03 (3H, m), 1.65 (2H, m), 1.54 (1H, m), 1.38 (3H, d), 1.28 (9H, s). $^{13}$C NMR (CDCl$_3$, mixture of rotamers) 173.7, 173.3, 173.2, 154.7, 153.6, 79.7, 65.6, 60.5, 56.7, 53.6.0, 52.2, 48.1, 46.9, 33.2, 31.8, 28.5 (3C), 24.5, 23.4, 17.5, 14.5. HRMS (FAB): calcd for $C_{20}H_{33}N_3O_6Na$ [M+Na]$^+$ 434.2267, obsd 434.2282 (Δ=3.4 ppm).

Cyclopentanone Ugi Tripeptide (7):

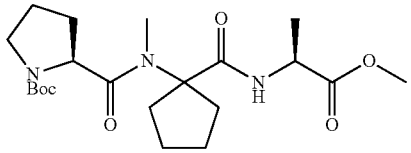 [SMILES: COC(=O)[C@H](C)NC(=O)C1(N(C)C(=O)[C@@H]2CCCN2C(=O)OC(C)(C)C)CCCC1]

Yield: 3.12 g (7.33 mmol, 78%). $R_f$=0.25 (7:3 EtOAc:hexanes), stains white with p-anisaldehyde. $^1$H NMR (CDCl$_3$, mixture of rotamers) 7.65 (1H, d), 4.54 (1H, m), 4.40 (1H, m), 3.65 (3H, s), 3.60 (1H, m), 3.45 (1H, m), 3.00 (3H, s), 2.52 (1H, m), (2.11-1.52 (12H, m) 1.43 (9H, s), 1.38 (3H, d). $^{13}$C NMR (CDCl$_3$, mixture of rotamers) 175.4, 173.6, 171.0, 154.7, 153.5, 79.4, 73.4, 73.0, 60.2, 58.0, 57.9, 52.0, 50.5, 48.2, 46.9, 36.2, 35.5, 34.8, 33.0, 29.2, 28.3 (3C), 24.2, 24.0, 23.1, 22.4, 17.6, 14.1. HRMS (FAB): calcd for $C_{21}H_{35}N_3O_6Na$ [M+Na]$^+$ 448.2424, obsd 448.2432 (Δ=1.8 ppm).

Cyclohexanone Ugi Tripeptide (8):

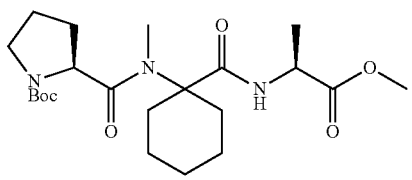 [SMILES: COC(=O)[C@H](C)NC(=O)C1(N(C)C(=O)[C@@H]2CCCN2C(=O)OC(C)(C)C)CCCCC1]

Yield: 3.75 g (8.53 mmol, 90%). $R_f$=0.25 (7:3 EtOAc: hexanes), stains white with p-anisaldehyde. $^1$H NMR (CDCl$_3$, mixture of rotamers) 6.72 (1H, m), 4.51 (1H, m), 4.37 (1H, m) 3.54 (3H, s), 3.45 (1H, m), 3.35 (1H, m), 2.98 (3H, s), (2.11-1.52 (14H, m) 1.43 (9H, s), 1.38 (3H, d). $^{13}$C NMR (CDCl$_3$, mixture of rotamers) 175.6, 173.7, 171.1, 154.5, 79.4, 66.6, 65.8, 60.2, 58.6, 52.2, 48.1, 46.7, 32.9, 32.4, 31.8, 30.4, 29.5, 28.5 (3C), 24.2, 22.8, 21.9, 20.9, 18.1, 17.7, 14.1. HRMS (FAB): calcd for $C_{22}H_{37}N_3O_6Na$ [M+Na]$^+$ 462.2580, obsd 462.2562 (Δ=3.9 ppm).

Procedure for the saponification of tripeptides: The tripeptide methyl esters (1.55 g, 3.62 mmol) were dissolved in 10.4 mL 1:1 THF:H$_2$O solution and LiOH.H$_2$O (356 mg, 8.47 mmol) added. Reaction was stirred for 2.5 h then quenched with 10 mL 1N HCl. THF was removed under vacuum and aqueous layer was extracted with 2×20 mL EtOAc. Organic layer was dried over Na$_2$SO$_4$ and concentrated under vacuum.

Procedure for Synthesis of Acyldepsipeptides (10a-h)

Linear Pentapeptolide Formation and Deprotection: Tripeptides (3.9 mmol), TPTU (1.45 g, 4.88 mmol), HOBt (770 mg, 5.7 mmol) and DIEA (2 mL, 11.5 mmol) were dissolved in 20 mL dry DCM and allowed to stir under N$_2$, at RT for 10 min. Depsipeptide (NH$_2$-Pro-N-CBz-Ser-phenacylester) (2.2 g, 3.9 mmol) was dissolved in 10 mL dry DCM and added dropwise over 5 min (see, e.g., US 20050107288). After 15 h the reaction mixture was concentrated in vacuo and then redissolved in 50 mL EtOAc. The EtOAc solution was extracted sequentially with 20 mL each of 0.2N HCl, saturated NaHCO$_3$ and brine. The organic layer was dried over Na$_2$SO$_4$ and concentrated in vacuo. The product was purified over a 110×55 mm bed of silica gel using 20:0.5 EtOAc:MeOH. Blue spots with $R_f$ 0.3 were visualized with ceric ammonium molybdenate.

Pentapeptolides (1.3 mmol) were phenacyl deprotected by dissolving in 1.45 mL 90% AcOH in H$_2$O, then Zn dust (580 mg, 9.07 mmol) added and reaction stirred for 30 min. Zn was filtered through cotton and residue washed with 10 mL EtOAc and 10 mL 1N HCl. 30 mL EtOAc was added to the filtrate and it was washed with 3×20 mL 1N HCl. Organic layer was dried with Na$_2$SO$_4$ and concentrated under vacuum. Yield: 945 mg (100%). $R_f$=0.2 (20:1 EtOAc:MeOH).

Macrocyclization: Pentafluorophenol esters were prepared from phenacyl deprotected linear peptides (1.37 mmol), by dissolving in 5.25 mL dry DCM and adding pentafluorophenol (1 g, 5.43 mmol) and EDC (285 mg, 1.64 mmol) at −78° C. Reaction was allowed to warm to room temperature overnight with stirring, then concentrated under vacuum. Crude pentafluorophenol esters (approximately 2 g) were Boc deprotected by treatment with 8.35 mL 3N HCl in EtOAc at 0° C. and stirred at 0° C. for 3.5 h. For cyclization the crude reaction mixture is diluted into 417 mL DCM and added dropwise at a rate of ~1 drop/sec to a vigorously stirring solution of 324 mL sat. NaHCO$_3$ and 557 mL DCM. Reaction was left to stir overnight. Organic layer was collected and dried over Na$_2$SO$_4$ and concentrated in vacuo, then purified over a 100×25 mm Si gel column with 20:1 EtOAc:MeOH eluent. In the case of diastereomers derived from 3 and 4, the compound with an $R_f$=0.3 has (2S)-pipecolate and the compound with an $R_f$=0.2 has (2R)-pipecolate.

Spectral data for S-Pip-CBz-macrocycle derived from 3:

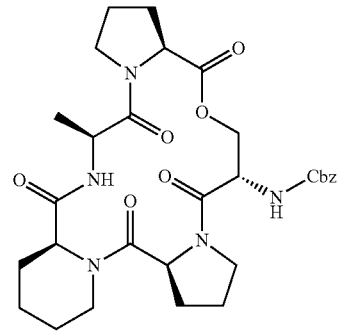 [SMILES: C[C@@H]1NC(=O)[C@@H]2CCCCN2C(=O)[C@@H]2CCCN2C(=O)[C@@H](NC(=O)OCc2ccccc2)COC(=O)[C@@H]2CCCN2C1=O]

$^1$H NMR (CDCl$_3$) 8.30 (1H,d, J=8 Hz), 7.28 (4H, m), 5.68 (1H, d, J=8 Hz), 5.15 (1H, m), 5.03 (2H, m), 4.99 (1H, m), 4.74 (1H, d, J=8 Hz), 4.66 (1H, s), 4.49 (2H, m), 4.17 (1H, t), 4.06 (1H, dd), 3.72 (2H, m), 3.65 (1H, m), 3.50 (2H, m), 2.68 (1H, d, J=12 Hz), 2.52 (1H, m), 2.31 (1H, m), 2.11 (3H, m), 1.91 (7H, m), 1.68 (1H, m), 1.58 (1H, m), 1.36 (5H, m). $^{13}$C NMR (CDCl$_3$) 173.3, 171.5, 169.6, 168.5, 166.2, 156.2, 135.9, 128.5, 128.3 (3H), 128.0, 67.9, 65.8, 60.3, 58.9, 57.1, 56.6, 53.9, 53.4, 48.0, 46.8, 46.3, 41.0, 30.9, 30.6, 28.2, 24.8, 23.1, 21.3, 18.0, 14.1. HRMS (FAB): calcd for $C_{30}H_{39}N_5O_8Na$ [M+Na]$^+$ 620.2696, obsd 620.2681 (Δ=2.4 ppm).

Spectral data for S-4-Me-Pip-CBz-macrocycle derived from 4:

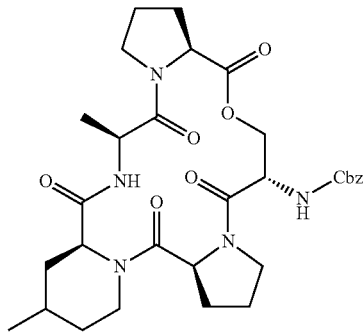

$^1$H NMR (CDCl$_3$) 8.31 (1H,d, J=8 Hz), 7.28 (4H, m), 5.63 (1H, d, J=8 Hz), 5.17 (1H, m), 5.03 (2H, m), 4.99 (1H, m), 4.76 (1H, d, J=8 Hz), 4.67 (1H, s), 4.50 (2H, m), 4.19 (1H, t), 4.08 (1H, dd), 3.72 (2H, m), 3.66 (1H, m), 3.49 (2H, m), 2.68 (1H, d, J=12 Hz), 2.53 (1H, m), 2.31 (1H, m), 2.12 (3H, m), 1.94 (7H, m), 1.56 (2H, m), 1.36 (3H, m), 1.02 (2H, m), 0.96 (3H, m). $^{13}$C NMR (CDCl$_3$) 173.2, 171.5, 169.7, 168.6, 166.2, 156.2, 135.8, 128.4, 128.3 (3H), 128.0, 67.9, 65.8, 60.3, 58.8, 57.1, 56.7, 53.9, 48.0, 46.9, 46.3, 40.7, 36.3, 33.1, 30.8, 30.5, 27.9, 23.0, 21.7, 21.2, 17.9. HRMS (FAB): calcd for $C_{30}H_{39}N_5O_8Na$ [M+Na]$^+$ 634.2853, obsd 634.2868 (Δ=2.4 ppm).

Deprotection of Macrocycles: Cbz-protected macrocycles (0.16 mmol) were deprotected using 75 mg 10% Pd/C and 100 mg NH$_4$COOH were dissolved in 4 mL isopropanol heated in a microwave reactor for 8 min at 85° C. (Daga et al., *Tetrahedron Lett.* 2001, 42, 5191). The reaction mixture was then filtered through celite, the residue washed with MeOH and the filtrate concentrated under vacuum. The CBz deprotected macrocycles (0.1 mmol) were coupled to 9 (44 mg, 0.15 mmol) in 800 μL DMF containing TPTU (50 mg, 0.17 mmol), HOBt (20 mg, 0.15 mmol), and 60 μL diisopropylethyamine. The reaction was stirred overnight at room temperature.

Purification of acyldepsipeptides (10a-h) compounds was accomplished using a Phenomenex Gemini C18 (10 micron, 150×10 mm, 110 Å). The method consisted of 20-80% MeCN in H₂0+0.1% TFA over 20 min. The detector was set to 214 nm. The flow rate was 10 mL/min.

Acyldpesipeptide 10a:

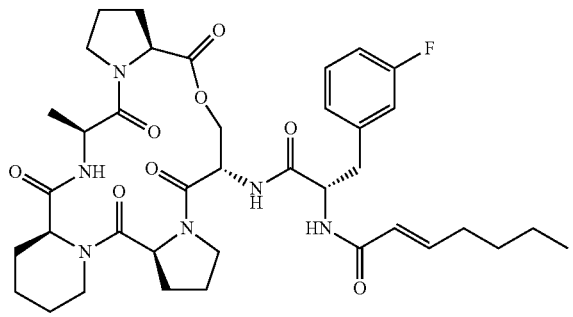 [SMILES: CCCC/C=C/C(=O)N[C@@H](Cc1cccc(F)c1)C(=O)N[C@H]1COC(=O)[C@@H]2CCCN2C(=O)[C@H](C)NC(=O)[C@@H]2CCCCN2C(=O)[C@@H]2CCCN2C1=O]

Isolated yield from deprotected peptidolactone: 25 mg (0.034 mmol, 34%) white amorphous powder. $^1$H NMR (CDCl$_3$) 8.55 (1H, d, J=8 Hz), 7.26 (0.5H, m), 7.22 (0.5H, m), 6.99 (1H, m), 6.89 (3H, m), 6.52 (1H, d, J=12 Hz), 6.17 (1H, d, J=16 Hz), 5.12 (1H, m), 4.98 (1H, m), 4.75 (1H, d, J=12 Hz), 4.67 (2H, m), 4.55 (1H, m), 4.48 (2H, m), 3.73 (1H, m), 3.61 (1H, m), 3.51 (2H, m), 3.30 (1H, m), 2.94 (2H, m), 2.71 (1H, m), 2.62 (1H, m), 2.34 (1H, m), 2.38 (4H, m), 1.92 (6H, m), 1.75 (1H, m), 1.64 (1H, m), 1.40 (1H, m), 1.38 (3H, m), 1.32 (4H, m), 0.88 (3H, m). $^{13}$C NMR (CDCl$_3$) 172.5, 171.2, 170.9, 169.4, 166.4, 165.0, 164.0, 161.5, 146.2, 138.6, 130.0, 125.2, 123.1, 116.5, 116.4, 113.8, 113.6, 65.0, 59.0, 57.1, 56.8, 54.7, 51.2, 47.8, 47.0, 46.4, 41.3, 38.4, 31.8, 30.7, 30.4, 28.0, 24.9, 23.1, 22.2, 21.3, 18.0, 13.8. HRMS (FAB): calcd for C$_{38}$H$_{51}$N$_6$O$_8$FNa [M+Na]$^+$ 761.3650, obsd 761.3625 (Δ=3.3 ppm).

Acyldpesipeptide 10b:

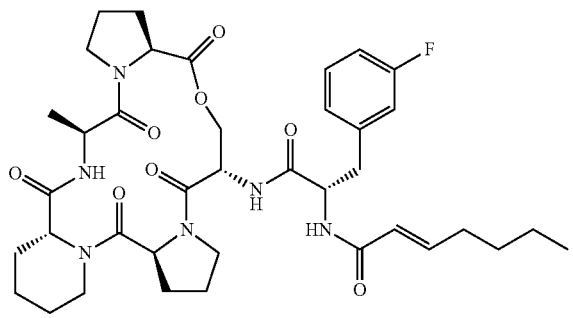 [SMILES: CCCC/C=C/C(=O)N[C@@H](Cc1cccc(F)c1)C(=O)N[C@H]1COC(=O)[C@@H]2CCCN2C(=O)[C@H](C)NC(=O)[C@H]2CCCCN2C(=O)[C@@H]2CCCN2C1=O]

Isolated yield from deprotected peptidolactone: 26 mg (0.035 mmol, 35%) white amorphous powder. $^1$H NMR (CDCl$_3$, mixture of rotamers) 8.03 (1H, m), 7.45 (1H, m), 7.18 (1H, m), 6.99 (4H, m), 6.85 (1H, m), 6.75 (1H, m), 6.56 (0.6H, m), 5.90 (1H, d), 5.80 (1H, d), 5.38 (1H, d), 5.30 (2H, m), 4.92 (3H, m), 4.76 (2H, m), 4.37 (1H, m), 4.33 (1H, m), 3.97 (1H, m), 3.80 (1H, m), 3.75 (2H, m), 3.63 (3H, m), 3.25 (3H, m), 3.10 (1H, m), 2.92 (1H, m), 2.65 (1H, m), 2.10 (4H, m), 2.01 (10H, m), 1.52 (2H, m), 1.45 (4H, m), 1.38 (3H, m), 0.85 (3H, m). $^{13}$C NMR (CDCl$_3$, mixture of rotamers) 172.2, 170.9, 170.3, 167.7, 167.3, 166.0, 163.8, 161.1, 129.7, 129.6, 125.0, 123.3, 116.3, 113.3, 61.2, 60.0, 56.1, 53.1, 48.5, 47.5, 47.2, 46.3, 44.7, 31.7, 30.1, 28.8, 28.7, 26.2, 25.6, 25.5, 25.0, 22.1, 20.6, 17.3, 13.4. HRMS (FAB): calcd for C$_{38}$H$_{51}$N$_6$O$_8$FNa [M+Na]$^+$ 761.3650, obsd 761.3638 (Δ=1.6 ppm).

Acyldpesipeptide 10c:

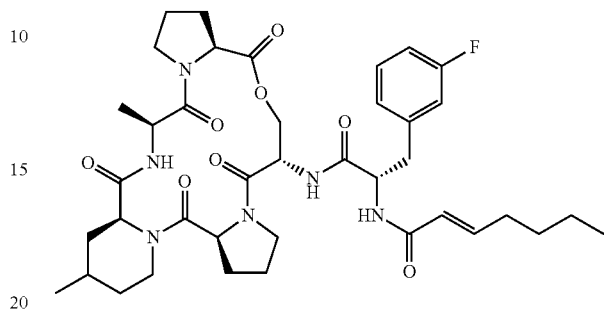

Isolated yield from deprotected peptidolactone: 23.4 mg (0.034 mmol, 31%) white amorphous powder. $^1$H NMR (CDCl$_3$) 8.89 (1H, bs), 8.51 (1H, d, J=12 Hz), 8.42 (0.5H, bs) 7.93 (0.5H, bs), 7.16 (1H, m), 6.88 (4H, m), 6.20 (1H, d, J=16 Hz), 5.14 (1H, m), 4.98 (1H, m), 4.73 (3H, m), 4.67 (1H, m), 4.50 (2H, m), 3.75 (1H, m), 3.55 (3H, m), 3.30 (1H, m), 2.94 (2H, m), 2.70 (2H, m), 2.31 (1H, m), 2.14 (3H, m), 1.88 (5H, m), 1.62 (2H, m), 1.38 (3H, m), 1.30 (5H, m), 0.94 (3H, m), 0.86 (3H, m). $^{13}$C NMR (CDCl$_3$) 172.5, 171.1, 170.8, 169.6, 167.1, 165.1, 164.0, 161.6, 147.0, 138.4, 130.2, 125.2, 122.9, 116.5, 114.0, 65.0, 59.1, 57.1, 57.2, 57.0, 55.2, 51.1, 47.9, 47.1, 46.6, 41.0, 38.4, 36.2, 33.3, 31.9, 30.8, 30.4 (2C), 28.0, 23.1, 22.2, 21.9, 18.0, 13.8. HRMS (FAB): calcd for C$_{39}$H$_{53}$N$_6$O$_8$FNa [M+Na]$^+$ 775.3807, obsd 775.3820 (Δ=1.7 ppm).

Acyldpesipeptide 10d:

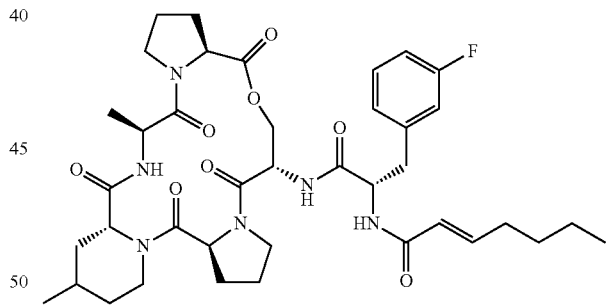

Isolated yield from deprotected peptidolactone: 22.1 mg (0.03 mmol, 30%) white amorphous powder. $^1$H NMR (CDCl$_3$, mixture of rotamers) 8.02 (1H, m), 7.74 (1H, bs), 7.51 (2H, m), 7.16 (1H, m), 6.96 (4H, m), 6.74 (1H, m), 5.96 (1H, m), 5.35 (0.5H, m), 5.30 (1H, m), 5.20 (0.5H, m), 4.82 (3H, m), 4.75 (1H, m), 4.40 (1H, m), 4.22 (1H, m), 4.01 (1H, m), 3.56 (3H, m), 3.25 (2H, m), 2.94 (1H, m), 2.62 (1H, m), 2.25 (3H, m), 2.02 (6H, m), 1.86 (5H, m), 1.62 (1H, m), 1.38 (3H, m), 1.30 (4H, m), 0.93 (3H, m), 0.85 (3H, m). $^{13}$C NMR (CDCl$_3$, mixture of rotamers) 172.1, 171.8, 171.3, 170.5, 170.2, 168.8, 161.5, 145.4, 140.2, 129.7, 124.8, 123.4, 116.4, 116.1, 113.4, 61.0, 60.3, 57.6, 56.6, 54.2, 53.3, 50.9, 47.5, 47.2, 46.4, 44.4, 40.9, 38.0, 33.9, 33.2, 32.8, 31.9, 30.4, 29.7, 28.9, 28.2, 27.3, 26.2, 25.7, 22.2, 21.7, 18.1, 15.1, 13.9. MS (ESI, m/z): 775.8 [M+Na]$^+$ for C$_{39}$H$_{53}$N$_6$O$_8$F.

Acyldpesipeptide 10e:

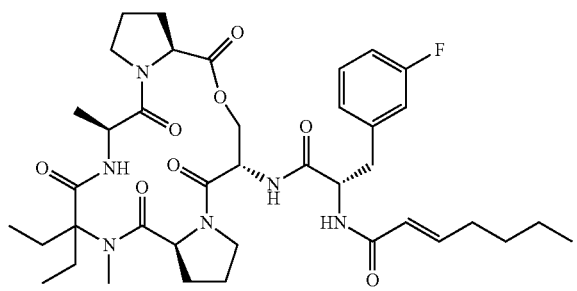 [SMILES: CCCC/C=C/C(=O)N[C@@H](Cc1cccc(F)c1)C(=O)N[C@H]1COC(=O)[C@@H]2CCCN2C(=O)[C@H](C)NC(=O)C(CC)(CC)N(C)C(=O)[C@@H]2CCCN2C1=O]

Isolated yield from deprotected peptidolactone: 22.0 mg (0.037 mmol, 37%) white amorphous powder. $^1$H NMR (CDCl$_3$, mixture of rotamers) 7.69 (1H, d), 6.99 (1H, d), 7.18 (1H, m), 6.94 (4H, m), 6.75 (1H, m), 5.94 (1H, d), 5.75 (1H, m), 5.58 (1H, m), 5.02 (1H, m), 4.90 (1H, m), 4.80 (2H, m), 4.62 (2H, m), 4.00 (1H, m), 3.70 (3H, m), 3.60 (2H, m), 3.28 (2H, m), 2.92 (1H, m), 2.60 (1H, m), 2.27 (3H, m), 2.02 (6H, m), 1.86 (5H, m), 1.72 (1H, m), 1.38 (3H, m), 1.30 (4H, m), 0.93 (3H, m), 0.85 (3H, m). MS (ESI, m/z): 777.4 [M+Na]$^+$ for C$_{39}$H$_{53}$N$_6$O$_8$F.

Acyldpesipeptide 10f:

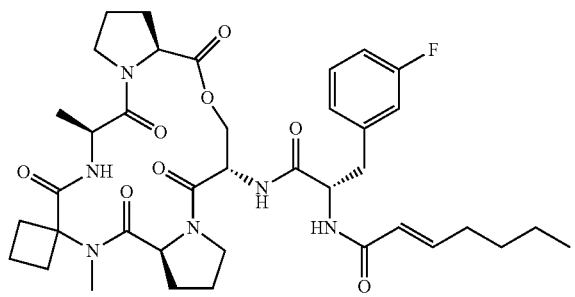 [SMILES: CCCC/C=C/C(=O)N[C@@H](Cc1cccc(F)c1)C(=O)N[C@H]1COC(=O)[C@@H]2CCCN2C(=O)[C@H](C)NC(=O)C2(CCC2)N(C)C(=O)[C@@H]2CCCN2C1=O]

Isolated yield from deprotected peptidolactone: 25 mg (0.034 mmol, 34%) white amorphous powder. $^1$H NMR (CDCl$_3$, mixture of rotamers) 7.52 (1H, d), 7.47 (1H, d), 7.15 (1H, m), 6.82 (4H, m), 5.90 (1H, d, J=16 Hz), 5.30 (1H, d), 4.92 (2H, m), 4.54 (1H, m), 4.40 (1H, m), 4.23, 1H, m), 3.85 (1H, d, J=12 Hz), 3.58 (3H, m), 3.34 (1H, m), 2.91 (3H, s), 2.85 (1H, m), 2.62 (2H, m), 2.06 (4H, m), 1.98 (4H, m), 1.81 (2H, d), 1.23 (4H, m), 0.85 (3H, m). $^{13}$C NMR (CDCl$_3$, mixture of rotamers) 172.4, 172.2, 171.0, 166.6, 161.6, 145.5, 140.2, 129.9, 125.3, 123.3, 116.5, 113.6, 66.8, 61.1, 60.2, 58.0, 56.9, 54.3, 51.2, 47.5, 38.0, 34.2, 32.9, 31.9, 30.3, 29.7, 29.4, 28.6, 28.1, 26.4, 26.2, 25.7, 23.3, 22.7, 22.2, 15.6, 15.3, 14.1, 13.9. MS (ESI, m/z): 761.3 [M+Na]$^+$ for C$_{38}$H$_{51}$N$_6$O$_8$F.

Acyldpesipeptide 10g:

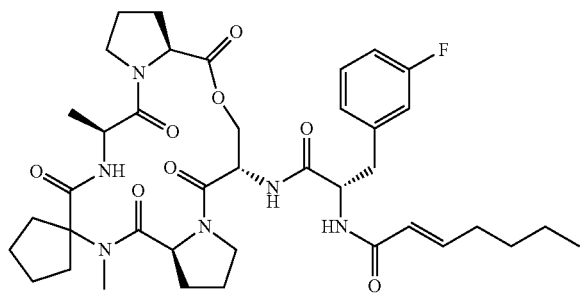 [SMILES: CCCC/C=C/C(=O)N[C@@H](Cc1cccc(F)c1)C(=O)N[C@H]1COC(=O)[C@@H]2CCCN2C(=O)[C@H](C)NC(=O)C2(CCCC2)N(C)C(=O)[C@@H]2CCCN2C1=O]

Isolated yield from deprotected peptidolactone: 23 mg (0.030 mmol, 30%) white amorphous powder. $^1$H NMR (CDCl$_3$, mixture of rotamers) 7.70 (1H, m), 7.49 (1H, m), 7.20 (1H, m), 6.97 (2H, m), 6.88 (1H, m), 6.72 (1H, m), 5.92 (1H, d, J=16 Hz), 5.35 (1H, d, J=12 Hz), 4.90 (2H, m), 4.83 (1H, m), 4.61 (1H, d), 4.37 (1H, m), 3.86 (1H, d, J=12 Hz), 3.69 (2H, m), 3.58 (1H, m), 3.49 (1H, m), 3.40 (1H, m), 3.19 (3H, s), 2.91 (1H, m), 2.60 (1H, m), 2.21 (2H, m), 2.10 (2H, m), 2.00 (2H, m), 1.92 (2H, m), 1.33 (3H, m), 0.85 (3H, m). $^{13}$C NMR (CDCl$_3$, mixture of rotamers) 174.0, 173.2, 172.6, 171.8, 171.2, 170.2, 167.3, 166.7, 163.9, 161.5, 155.6, 140.5, 129.6, 125.1, 116.4, 113.2, 79.5, 74.6, 61.0, 60.8, 60.0, 59.4, 59.0, 56.2, 51.1, 47.5, 46.1, 38.5, 37.9, 36.9, 35.5, 35.1, 33.4, 31.9, 29.4, 28.2, 27.9, 26.4, 25.8, 25.0, 24.6, 23.5, 22.6, 18.2, 15.6, 14.1. MS (ESI, m/z): 775.6 [M+Na]$^+$ for C$_{39}$H$_{55}$N$_6$O$_8$FNa.

Acyldpesipeptide 10h:

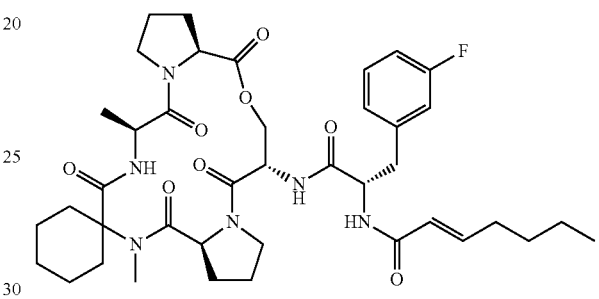

Isolated yield from deprotected peptidolactone: 24 mg (0.032 mmol, 32%) white amorphous powder. $^1$H NMR (CDCl$_3$, mixture of rotamers) 7.76 (1H, d, J=8 Hz), 7.48 (1H, d, J=4 Hz), 7.20 (1H, m), 6.82 (4H, m), 5.90 (1H, d, J=16 Hz), 5.36 (1H, d, J=8 Hz), 4.92 (2H, m), 4.72 (1H, m), 4.37 (1H, m), 3.70 (1H, m), 3.58 (2H, m), 3.39 (2H, m), 3.18 (3H, s), 2.24 (2H, m), 2.05 (6H, m), 1.83 (1H, m), 1.63 (1H, m), 1.38 (3H, m), 0.85 (3H, m). $^{13}$C NMR (CDCl$_3$, mixture of rotamers) 174.7, 171.4, 170.7, 170.3, 167.2, 166.4, 145.9, 140.3, 129.7, 124.9, 123.3 (2C), 116.3, 113.4, 69.9, 61.1, 60.2, 60.0, 59.2, 54.4, 51.0, 47.4, 46.4, 40.3, 38.1, 34.5, 33.8, 33.4, 31.9, 29.4, 26.3, 25.7, 23.3, 22.7, 22.2, 18.5, 18.1, 14.2, 13.8. MS (ESI, m/z): 789.6 [M+Na]$^+$ for C$_{40}$H$_{55}$N$_6$O$_8$FNa.

Synthesis of allo-threonine Analongs

Synthesis of enopeptide analogs containing allo-threonine instead of serine, i.e., wherein R$^{11}$ is —CH$_3$ instead of hydrogen, is further contemplated. Synthesis of such an analog will follow the synthetic method as detailed herein. Allo-threonine may be synthesized following the procedure of Liang et al., *Bioorganic and Medicinal Chemistry* (2011) 19:852-860. Synthesis of the prolyl-allo-threonine ester fragment may be generated following the procedure of Hinzen et al., *Chem Med Chem* (2006) 1:689.

Biological Assays

Minimum inhibitory concentrations (MIC) were determined in duplicate using methods outlined by The Clinical and Laboratory Standards Institute. Compounds were dissolved in DMSO and fresh cation-adjusted Mueller-Hinton broth (SMHB; Difco Laboratories, Sparks, Md., USA; 25 µg/mL calcium and 12.5 µg/mL magnesium) was used to dilute antimicrobial agents in a serial 2-fold schedule. Colony counts for the inoculum verification was determined using Tryptic Soy Agar plates (TSA, Difco, Becton Dickinson Co., Sparks, Md., USA). Following incubation, 100 µL of broth was subcultured onto TSA for MBC determination. MIC and MBC determination can be found in Table 2 and 3. Control isolates were obtained from the American Type Culture Collection (ATCC) and were as follows: Methicillin-resistant *S. epidermidis* (MRSE ATCC 35984); MSSA (ATCC 35556) and, VRE (ATCC 2030).

Example 2. Enopeptins and Virulence

Figure 6:
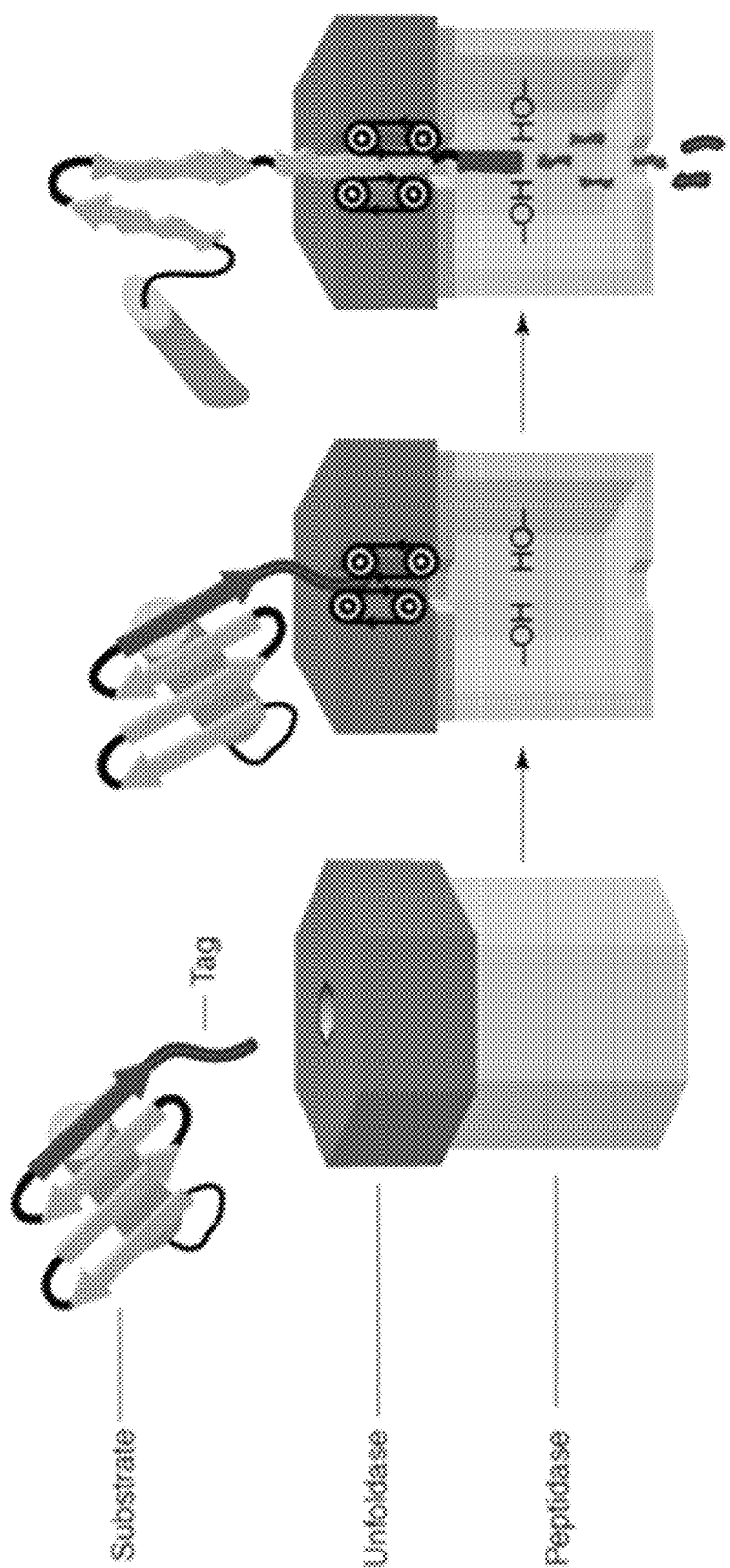
FIG. 6 depicts an illustration of the mechanism of action of ClpP (peptidase). ClpP is a multi-subunit protease with internally oriented active sites. ATP-dependent unfoldases unfold proteins (substrates) that are targeted for proteolysis and translocate them into the proteolytic chamber of ClpP (see Baker et al., *Trends Biochemical Sciences* (2006) 31:647-653).

Enopeptins do not suffer from cross-resistance to all antibacterial agents on the market or those in clinical development because their mechanism of action is distinct from all clinically used antibacterial drugs they bind and deregulate the activity of the ClpP protease (see, e.g., Brötz-Oesterhelt et al., *Nature Medicine,* 10, 1082-1087 (2005); Kirstein et al., *EMBO Molecular Medicine.* 1, 3-49; Lee et al., *Nature Structural Biology* (2010) 17:471-479). ClpP (caseinolytic protease) is structurally and functionally analogous to the eukaryotic proteasome (see, e.g., Gottesman, *Annual Review of Cell and Developmental Biology.* 19, 565-587 (2003); Baker et al., *Trends Biochemical Sciences.* 31, 647-653 (2006); Singh et al., *Proceedings of the National Academy of Science, USA.* 97, 8898-8903 (2000); Hsiung et al., *FEBS Letters.* 581, 3749-3757 (2007); Kessel et al., *Journal of Molecular Biology.* 250, 587-594 (1995)). As is the case for the proteasome, ClpP monomers self-assemble into two heptameric rings that dimerize to form a large barrel-shaped structure (see, e.g., Hsiung et al., *FEBS Letters.* 581, 3749-3757 (2007); Wang et al., *Cell.* 91, 447-456 (1997); Wang et al., *Journal of Structural Biology.* 124, 151-163 (1998); Szyk et al., *Journal of Structural Biology.* 156, 165-174 (2006)). The internal chamber of this tetradecamer is decorated with fourteen serine protease active sites and is large enough to accommodate a 50 kDa protein. Twelve angstrom-wide pores at both poles of the complex are too narrow to allow entry of most folded proteins into the proteolytic chamber. Thus, accessory ATPases like ClpA, ClpX, ClpL, and ClpC are required to unfold protein substrates of the ClpP protease (see, e.g., Maurizi et al., *Methods in Enzymology.* 244, 314-331 (1994); Thompson et al., *Journal of Biological Chemistry.* 269, 18209-18215 (1994); Maurizi et al., *Biochemistry.* 37, 7778-7786 (1998); Kessel et al., *Journal of Molecular Biology.* 250, 587-594 (1995)). Under normal conditions, this fourteen-subunit protease selectively degrades damaged and misfolded proteins through a physical and functional association with accessory ATPases that recognize and unfold its substrates (FIG. 6) (see, e.g., Gottesman, *Annual Review of Cell and Developmental Biology.* 19, 565-587 (2003); Baker et al., *Trends Biochemical Sciences.* 31, 647-653 (2006); Singh et al., *Proceedings of the National Academy of Science, USA.* 97, 8898-8903 (2000); Hsiung et al., *FEBS Letters.* 581, 3749-3757 (2007)). The binding of the enopeptins to ClpP blocks its association with accessory ATPases (see, e.g., World Health Organization (WHO) Geneva, World Health Report 2002; Nathan, *Nature,* 431, 899 (2004)). Instead of inhibiting the ATPase-dependent activity of ClpP, the enopeptins apparently reprogram ClpP, switching it from a regulated to an uncontrolled protease. The bactericidal activity of the enopeptins results from the fact that enopeptin-bound ClpP indiscriminately degrades nascent peptides as they emerge from the ribosome (see, e.g., Brötz-Oesterhelt et al., *Nature Medicine,* 10, 1082-1087 (2005); Kirstein et al., *EMBO Molecular Medicine.* 1, 37-49; Lee et al., *Nature Structural Biology* (2010) 17:471-479). Unlike most antibiotics which inhibit macromolecular function, the enopeptins activate their cellular target.

The exceptionally low MICs of the enopeptins against bacteria implies that they have a very high affinity for ClpP. Recent structural studies revealed the manner in which an enopeptin and a synthetic derivative thereof bind to ClpP (see, e.g., Lee supra). In the crystal structures of enopeptin-Clp complexes, the antibiotics bind at the interfaces between ClpP monomers in the tetradecameric complex. They make extensive contacts with the N-terminal hairpin region of ClpP that interacts with accessory ATPases. The proline-rich peptidolactone core structures make multiple hydrophobic contacts with ClpP involving Ile28, Ile90, Tyr112, and Leu189. Additionally, the N-acyl-phenylalanine side chains of the peptidolactones bind in the innermost region between adjacent ClpP monomers. While the N-acyl-phenylalanine side chain of the enopeptins is deeply buried in ClpP, approximately half of their peptidolactone core is solvent accessible. Because it is so deeply buried at the interface between ClpP monomers, we suspect that the N-acyl-phenylalanine side chain of the enopeptins strongly contributes to their high affinity for ClpP. In any case, a comparison of the structures of free ClpP and the enopeptin-bound ClpP makes it clear that the antibiotics induce a "closed-to-open gate" transition of the ClpP N-terminal domains, which exposes the proteolytic chamber of the tetradecamer.

Although the enopeptin natural products have remarkable antibacterial activity in vitro, their chemical lability and poor solubility limit their efficacy in vivo (see, e.g., Brötz-Oesterhelt et al., *Nature Medicine,* 10, 1082-1087 (2005); Hinzen et al., *Chem Med Chem.* 1, 689-693 (2006)). In an effort to improve the pharmacological properties of the enopeptins, a research group at Bayer Healthcare AG carried out an intensive effort to optimize the structures of the enopeptins. Their medicinal chemistry program was guided in part by the observation that the conformation of the peptidolactone core structure was constrained by two transannular hydrogen bonds to the phenylalanine moiety of the side chain. On this basis, it was anticipated that replacing the constituents of the peptidolactone with conformationally restricted amino acids would yield enopeptin derivatives with improved antibacterial activity. Most amino acid substitutions in the peptidolactone core structure decreased antibacterial activity, but replacement of the N-methylalanine moiety with a more conformationally restricted pipecolate moiety yielded a more potent analogue. Presumably, rigidification of the peptidolactone lowers the entropic cost of binding to the ClpP core. The stability and antibacterial activity of these rigidified enopeptin analogs were further enhanced by replacement of the exocyclic phenylalanine with 3,5-difluorophenylalanine and by substitution of the polyunsaturated side chain with long chain α,β-unsaturated amides. One optimized enopeptin derivative, known as acyldepsipeptide 4 (ADEP 4) (FIG. 1), exhibited remarkable activity both in vitro and in vivo. As was the case for the parent enopeptins, no cross-resistance to ADEP 4 and the other synthetic derivatives of the enopeptins was observed; the compounds were active against multi-drug resistant pathogens (see, e.g., Brötz-Oesterhelt et al., *Nature Medicine,* 10, 1082-1087 (2005); Hinzen et al., *Chem Med Chem.* 1, 689-693 (2006); Kirstein et al., *EMBO Molecular Medicine.* 1, 37-49; Lee et al., *Nature Structural Biology* (2010) 17:471-479). ADEP4 and other synthetic derivatives of the enopeptins were shown to clear methicillin-resistant *Staphylococcus aureus,* vancomycin-resistant *E. faecalis,* and *Streptococcus pneumoniae* infections in both mice and rats. Mice infected with a lethal innocula of *Enterococcus faecalis* had a 100% survival rate when treated with a single dose of ADEP 4 at 0.5 mg/kg. Remarkably, the minimum inhibitory concentration (MIC) and in vivo antibacterial activity of ADEP 4 equaled or even surpassed that of linezolid, an FDA approved antibacterial drug.

Despite their promising activity and efficacy in mouse models of infection, Bayer Healthcare AG has not pursued clinical development of the acyldepsipeptides. The group at Bayer predicted that the acyldepsipeptides would have limited clinical utility because enopeptin-resistant bacteria are observed at a relatively high frequency ($10^{-6}$) (see, e.g., Brötz-Oesterhelt, supra). The high frequency of spontaneous enopeptin resistance may be reflective of the fact that clpP is dispensable for viability (see, e.g., Kwon et al., *Infection and Immunity.* 71, 2757-3765 (2003); Kwon et al., *Infection and Immunity.* 72, 56460-5653 (2004); Robertson et al., *Journal of Bacteriology.* 184, 3508-3520 (2002); Gaillot et al., *Molecular Microbiology.* 35, 1286-1294 (2000); Webb et al., *Molecular Microbiology.* 34, 112-123 (1999); Frees et al., *Molecular Microbiology.* 48, 1565-78 (2003); Frees et al., *Infection Immunity.* 73, 8100-8 (2005)). Using *E. coli* as a model system, Bayer found that enopeptin-resistant strains often have loss-of-function mutations in the clpP gene. One enopeptin-resistant mutant of *E. coli* that they characterized had a missense mutation in the clpP gene that resulted in a threonine to alanine substitution at position 182 (see, e.g., Brötz-Oesterhelt, supra). The proximity of this substitution to the ClpP active site was invoked to explain the catalytic inactivity of the protease. Because ClpP is not essential for viability and the antibacterial activity of the enopeptins requires a functional ClpP, it is anticipated that loss-of-function mutations in the clpP gene will be common in enopeptin-resistant bacteria. As is the case for other antibacterial drugs with high rates of resistance (e.g., rifampicin), it has been proposed that the enopeptins may be most effective as part of combination therapy with other antibacterial drugs (see, e.g., Kirstein, supra). However, systematic studies of the enopeptin derivatives in complex with other antibacterial drugs has not yet been reported.

The enopeptin antibiotics and their synthetic derivatives are a remarkable group of drug leads that satisfy many of the criteria of conventional drug discovery programs. They have potent activity against troublesome, multi-drug resistant pathogens (i.e., MICs are less than 1 mg/mL) (see, e.g., Brötz-Oesterhelt et al., *Nature Medicine,* 10, 1082-1087 (2005); Hinzen et al., *Chem Med Chem.* 1, 689-693 (2006)). They target a protein that is not bound by any other clinically used antibacterial drugs (i.e., the ClpP protease is a novel target) and have an unprecedented mechanism of action (i.e., activation of proteolysis). They are not toxic to eukaryotes and can be safely used to treat infections in mice. In the context of conventional drug discovery programs, the critical flaw of the enopeptin antibiotics is that resistant-bacteria are observed at a high frequency. We propose that these acyldepsipeptides have two features that make them great candidates for anti-virulence programs. First, the antibiotics bind to the accessory ATPase binding site on ClpP that is must be accessible for ClpP to have its normal physiological function. Any compound that blocks the association of ClpP with its accessory ATPases will be an inhibitor of ClpP function and as such will be an inhibitor of virulence factor production. Mechanism-based inhibitors of ClpP are known to block virulence factor production in MRSA and infectivity in *L. monocytogenes* (see, e.g., Böttcher et al., *Journal of the American Chemical Society.* 130, 14400-14401 (2008); Böttcher et al., *Chem Bio Chem,* 10, 663-666 (2009); Böttcher et al., *Chem Med Chem.* 4, 1260-1263 (2009); Osada et al., *Journal of Antibiotics.* 44, 1463-1466 (1991)). Thus, we hypothesize that the structure of the enopeptin-ClpP complex can be used as the basis for the design of novel ClpP ligands that do not activate the enzyme's proteolytic activity. One would anticipate that such compounds would lack antibacterial activity, but would block virulence factor production by pathogens. Second, while drug resistance is generally has disastrous consequences in clinical settings, we hypothesize that resistance to the acyldepsipeptides will be advantageous with respect to clearing infections. Since resistance to the acyldepsipeptides has been ascribed to loss of function mutations in the clpP gene and a functional clpP gene is required by many pathogenic bacteria for virulence factor production (including *Salmonella typhimurium, Listeria monocytogenes, Streptococcus pneumonia,* and *Staphylococcus aureus* strains) (see, e.g., Kwon et al., *Infection and Immunity.* 71, 2757-3765 (2003); Kwon et al., *Infection and Immunity.* 72, 56460-5653 (2004); Robertson et al., *Journal of Bacteriology.* 184, 3508-3520 (2002); Gaillot et al., *Molecular Microbiology.* 35, 1286-1294 (2000); Webb et al., *Molecular Microbiology.* 34, 112-123 (1999); Frees et al., *Molecular Microbiology.* 48, 1565-78 (2003); Frees et al., *Infection Immunity.* 73, 8100-8 (2005)), we hypothesize that acyldepsipeptide-resistant bacteria will be avirulent. Thus, the use of acyldepsipeptides as antibacterial drugs could initially cure bacterial infections and ultimately drive the evolution of drug-resistant bacteria that do not cause disease.

(i) Synthesize and Evaluate the Capacity of Acyldepsipeptide Derivatives to Affect Antibacterial Activity and/or Virulence Factor Production in Pathogenic Bacteria.

Figure 7A:
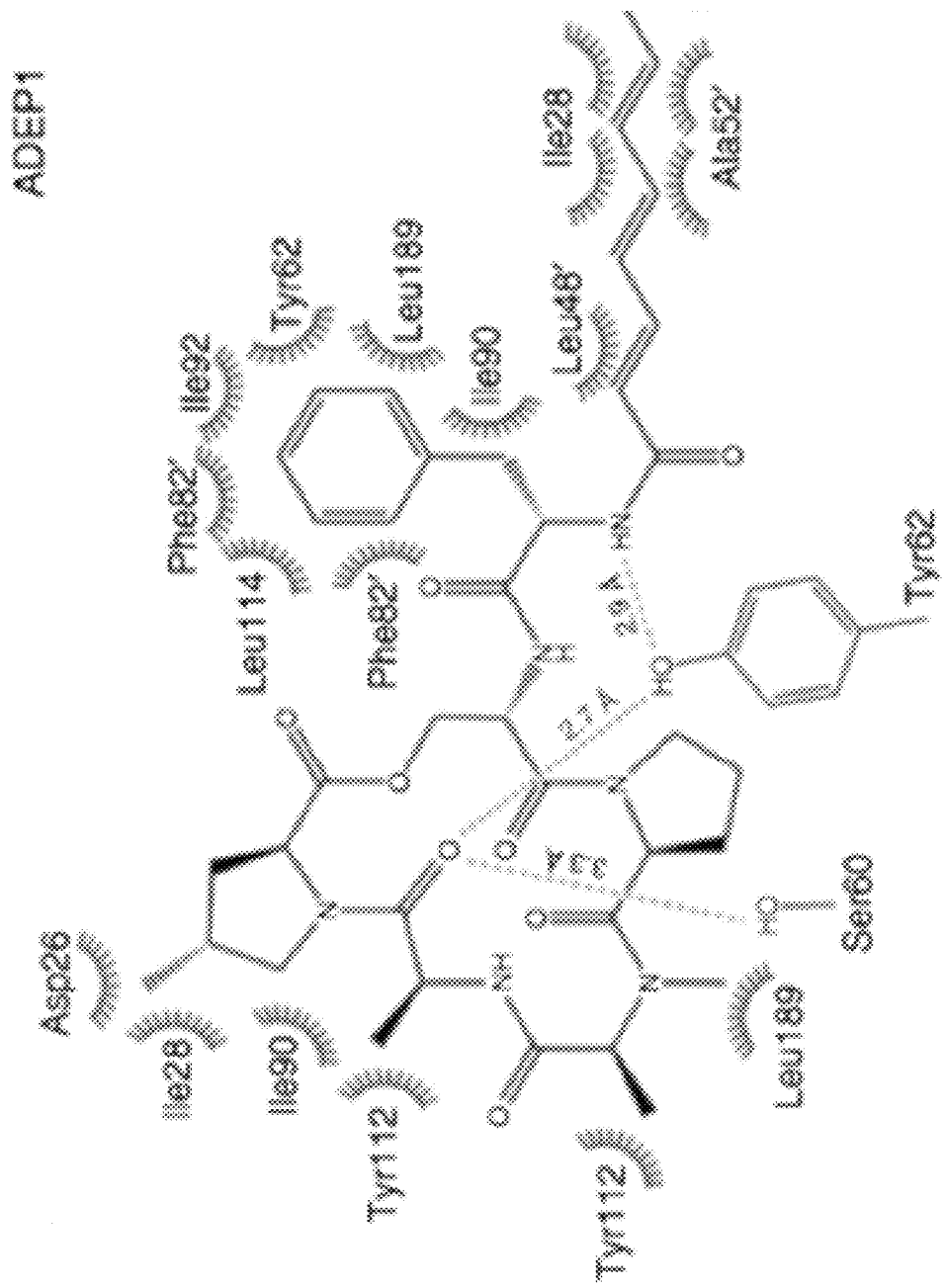
FIGS. 7A-7B illustrate the crystal structure of enopeptin derivatives in complex with *B. subtilis* ClP. These molecules make extensive hydrophobic contacts with ClpP.
Figure 7B:
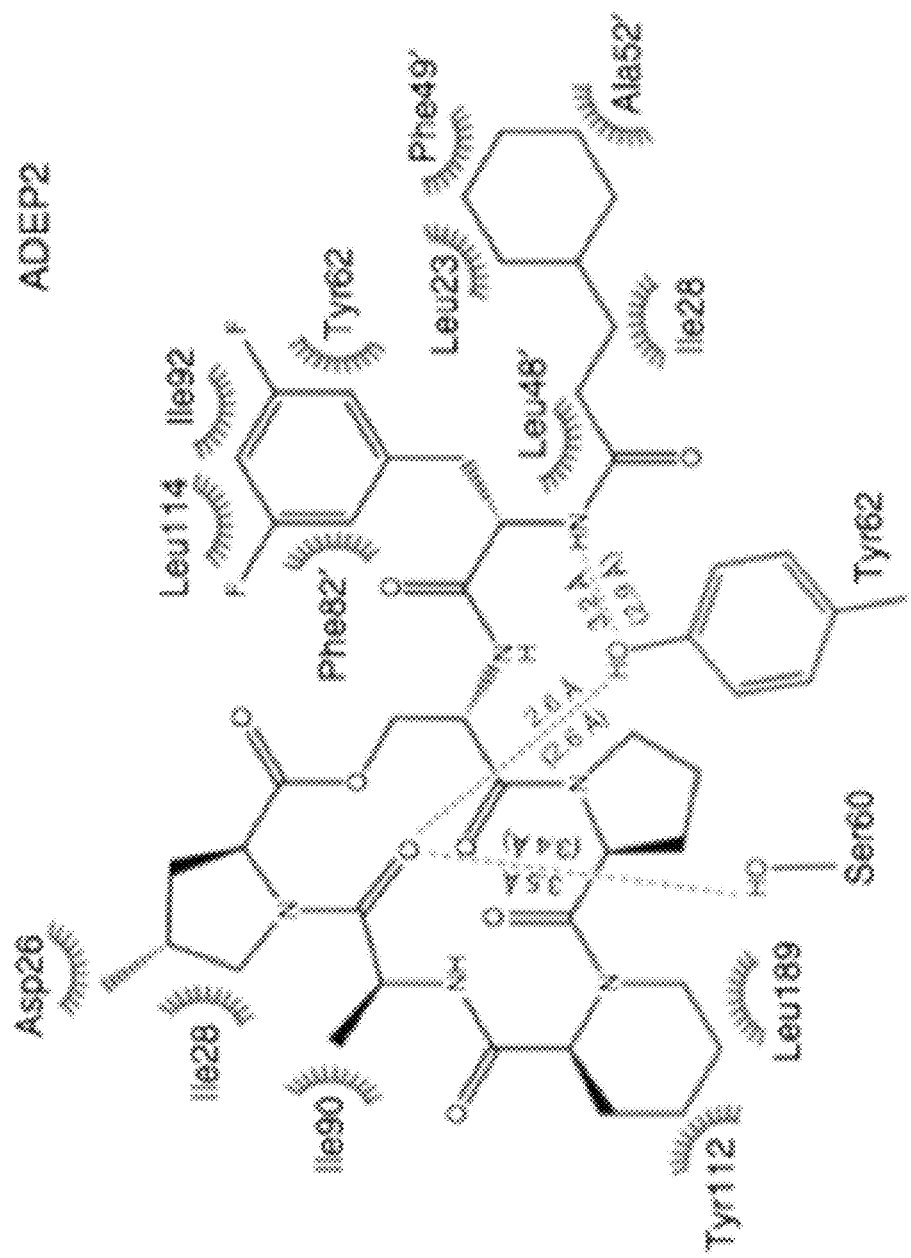

Based on the structure of the enopeptins, we successfully designed an analog with enhanced antibacterial activity. The recently published crystal structure of the acyldepsipeptide in complex with *B. subtilis* ClpP provides additional opportunities for structure-based design (FIGS. 7A-7B) (see, e.g., Lee et al., *Nature Structural Biology* (2010) 17:471-479). It is likely that structure-based design and synthesis will be able to yield either enhanced activators of ClpP activity or inhibitors of ClpP activity. Enopeptin analogs that form additional contacts with ClpP will bind more tightly and thus activate its activity more strongly. In contrast, enopeptin analogs that have lower affinity for the ATPase binding site of ClpP than the parent compounds are likely to be inhibitors of the protease's activity. These compounds will not have antibacterial activity, but they will block the ClpP-dependent virulence. Inhibition of ClpP is known to block virulence in *S. aureus* and *L. monocytogenes* (see, e.g., Böttcher et al., *Journal of the American Chemical Society.* 130, 14400-14401 (2008); Böttcher et al., *Chem Bio Chem,* 10, 663-666 (2009); Böttcher et al., *Chem Med Chem.* 4, 1260-1263 (2009); Osada et al., *Journal of Antibiotics.* 44, 1463-1466 (1991)).

(ii) Rational Modification of the N-acyl-phenylalalnine Moiety will Yield Enopeptin Analogs having Enhanced Antibacterial Activity or Anti-Virulence Activity.

Figure 8:
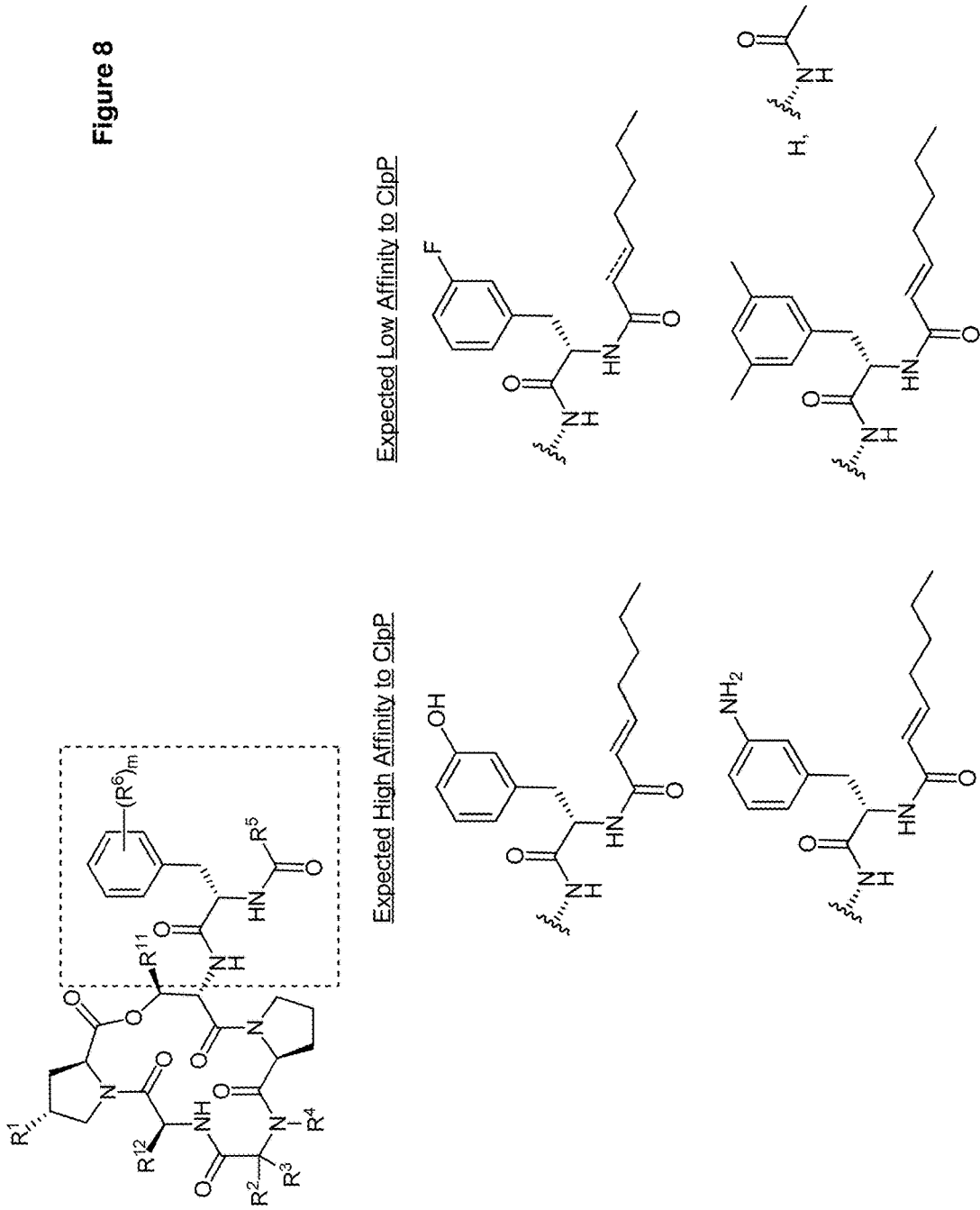
FIG. 8 depicts synthetic enopeptin analogs of interest. Targeted changes to the N-acyl phenylalanine side chain that are expected to affect ClpP binding and thus the biological mechanism.

We will examine a variety of enopeptin derivatives, including those that we recently reported do not have antibacterial activity. The structurally similarities of these compounds to those that have antibacterial activity suggests that they may retain their ability to bind ClpP. Additional ClpP ligands will be rationally designed and synthesized. The recently published structure of *B. subtilis* ClpP in complex with an optimized enopeptin derivative called ADEP 2 will be used in the rational design (FIG. 7B) (see, e.g., Lee et al., *Nature Structural Biology* (2010) 17:471-479). We hypothesize that the ideal target for modification is the acyl 3,5-difuorophenylalanine moiety of ADEP 2. As it is deeply buried at the interface between ClpP monomers, the acyl 3,5-difluorophenylalanine side chain of ADEP2 is a significant contributor to high affinity binding of the molecule to ClpP. The α,β-unsaturation of the acyl group is critical for activity and the two fluorine atoms dramatically enhance activity of ADEP 2. Targeted modifications of (1) the unsaturated unit or (2) the 3,5-difluorophenyl moiety should yield small molecules with either higher and lower affinity for ClpP. For example, a compound containing a saturated acyl group may bind ClpP with insufficient for ClpP activation,but sufficient affinity to compete for the ATPase binding site. This same analysis can be applied to the difluorophenylalanine appended to ADEP 2. One fluorine atom is well accommodated in a polar environment formed by the main chain acyl of Asp78 and the β-hydroxy group of Thr79. Replacement of this group with hydrogen bond donors, like an amino group or a hydroxyl group, could yield higher affinity ClpP ligands since they will likely form hydrogen bonds to Asp78 and Thr79 (FIG. 8). In contrast, derivatives lacking the side chain entirely or with bulky non-polar substituents on the phenyalanine moiety are likely to have lower affinity for ClpP (FIG. 8). We hypothesize that the enopeptin derivatives with low affinity for ClpP will not have bactericidal activity, but inhibit virulence factor production via competitive binding to the ATPase site of ClpP. Accordingly, hypothesize that the enopeptin derivatives with high affinity for ClpP will have enhanced bactericidal activity.

Minimum inhibitory concentration (MIC) determinations will be conducted using proven methodologies described in documents published by The Clinical and Laboratory Standards Institute (CLSI). MICs will be determined in duplicate using serial dilution (see, e.g., Performance standards for antimicrobial susceptibility testing; Sixteenth informational supplement. M100-S16. Clinical Laboratory Standards Institute (formerly NCCLS), Wayne, Pa. (2006)). Prototype ATCC strains of *Enterococcus faecium* (ATCC 29212), methicillin-susceptible *Staphylococcus aureus* (ATCC 35556), and methicillin-resistant *Staphylococcus aureus* (ATCC 43300). We will measure the properties of novel antibiotics against panels of clinical isolates (i.e., those obtained from hospitalized patients). The clinical isolates provide a better assessment of the true potential of an investigational agent. The panel of clinical isolates, numbering in the hundreds and representing diverse types of Gram-positive bacteria, was obtained by random samplings from patient blood, sputum, tissue, and urine at the Veterans Affairs Medical Center in Providence, R.I. (June 2004 through July 2010).

To follow up on our finding that the minimal bactericidal concentrations of the enopeptin derivatives are nearly identical to the minimal inhibitory concentrations, we plan to carry out time kill kinetic assays. These time-kill experiments will be used to more fully measure and classify antibiotic activities. These studies will use the prototype ATCC isolates described above. Each time-kill will be preformed in duplicate and bacterial quantification of all samples were preformed as previously described (see, e.g., Socha et al., *Bioorg Med Chem.* 14: 8446-54 (2006)). All antimicrobial agents will be tested at two times their respective MIC with a starting inoculum of $5\times10^5$ CFU/mL. Colony counts will be determined by plating 20 µL of each diluted sample onto TSA plates in triplicate, followed by incubation at 35° C. for 24 h. This methodology has a lower limit of detection of 2.0 $\log_{10}$ CFU/ml. Growth control wells for each organism will be prepared without antibiotic and run in parallel to the antibiotic test wells. Bactericidal activity (99.9% kill) is defined as a ≥3 $\log_{10}$ CFU/ml reduction in bacterial density from the starting inoculum (see, e.g., LaPlante et al., *Antimicrob Agents Chemother* 48:4665-72 (2004)). Time to 99.9% kill will be determined by linear regression of the sample points if $r^2 \geq 0.95$ or by visual inspection.

We hypothesize that any enopeptin derivative that does not have antibacterial activity may still retain the ability to bind to ClpP in vitro and in vivo. The acyldepsipeptide analogs lacking antibacterial activity will be tested for their ability to block the binding of ClpP to accessory ATPases in vitro. For these analyses, we will use size exclusion chromatography using purified ClpP, MecA, and ClpC, as described by Kirstein et al., *EMBO Molecular Medicine.* 1, 37-49. These three proteins are known to form a high molecular weight complex that dissociates in the presence of the acyldepsipeptides. In the presence of the enopeptin-binding acyldepsipeptides, two discrete species corresponding to the ClpP tetradecamer and the MecA-ClpC complex are observed. Compounds of interest are those that trigger disassembly of the complex via competition for the ATPase binding site of ClpP. This analytical method will unambiguously determine if any synthetic compounds trigger disruption of this complex. The successes of size exclusion chromatography in biophysical analyses of ClpP suggest that these approaches will be an ideal means by which to identify ClpP ligands. The shape of the curve and other data from these analyses will also reveal differences in the degrees to which enopeptin derivatives trigger ClpP complex disassembly (kinetic analyses). These experiments, which are well described and straightforward, will be carried out with a fast protein liquid chromatograph (FPLC). Although this is not a high-throughput assay, the small number of compounds (<15) makes this approach tenable.

Any compounds of interest identified as ClpP ligands in the primary screen will be tested to determine if they affect viability and virulence factor production in the aforementioned in vivo and in vitro assays (see, e.g., Böttcher et al., *Journal of the American Chemical Society,* 130, 14400-14401 (2008); Böttcher et al., *Chem Bio Chem,* 10, 663-666 (2009); Brötz-Oesterhelt et al., *Nature Medicine,* 10, 1082-1087 (2005)). For the in vitro experiments, virulence factor expression by *S. aureus* will be assessed using plate-based assays based on pathogen-mediated hemolysis and proteolysis, as well as in lipase and DNase activity assays. In parallel, it will be determined if the compounds interfere with the virulence of pathogens in mouse models of *Staphylococcus aureus* infections. As described by the research group at Bayer Healthcare AG, we plan to intraperitoneally inoculate CFW-1 mice with bacterial loads above and below the lethal infective doses (see, e.g., Brötz-Oesterhelt, supra). The mice will be treated with small molecules of interest once intraperitoneally 30 minutes after the infection. Five animals will be used per treatment group and monitored for five days to assess survival. For determination of colony-forming units in the mice, their organs will be removed 6 h after infection and homogenized. The bacteria in the homogenates will be counted on agar plates. Statistical analyses using the Mann-Whitney test will be used for CFU determination and the log-rank test will be used to generate survival models.

Other Embodiments

All patents, patent applications, and literature references cited herein are incorporated herein by reference.

The foregoing has been a description of certain nonlimiting embodiments of the invention. Those of ordinary skill in the art will appreciate that various changes and modifications to this description may be made without departing from the spirit or scope of the present invention, as defined in the following claims.

What is claimed is:
1. A compound of Formula (III-a):

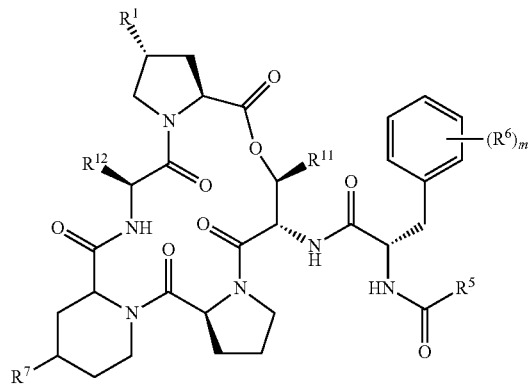

(III-a)

or a pharmaceutically acceptable salt thereof;
wherein:
$R^1$ is hydrogen or $CH_3$;
$R^7$ is halogen, OH, —SH, —$NH_2$, —CN, —$NO_2$, —$N_3$, —$SO_2H$, —$SO_3H$, substituted hydroxyl, substituted thiol, substituted amino, sulfonyl, sulfinyl, acyl, silyl, boronyl, optionally substituted $C_{2-6}$ alkyl, substituted $C_1$ alkyl, optionally substituted alkenyl, optionally substituted alkynyl, optionally substituted carbocyclyl, optionally substituted heterocyclyl, optionally substituted aryl, or optionally substituted heteroaryl;
$R^5$ is:

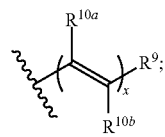

(a)

x is an integer between 1 and 10, inclusive;
$R^{10a}$ and $R^{10b}$ are independently hydrogen or optionally substituted alkyl;
$R^9$ is hydrogen, halogen, —CN, —$NO_2$, —$N_3$, substituted hydroxyl, substituted thiol, sulfonyl, sulfinyl, acyl, silyl, boronyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
each instance of $R^6$ is independently halogen, —OH, —SH, —$NH_2$, —CN, —$NO_2$, —$N_3$, —$SO_2H$, —$SO_3H$, substituted hydroxyl, substituted thiol, substituted amino, sulfonyl, sulfinyl, acyl, silyl, boronyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
m is 0 or an integer of between 1 and 5, inclusive;
$R^{11}$ is hydrogen; and
$R^{12}$ is —$CH_3$.

2. The compound of claim 1, or a pharmaceutically acceptable salt thereof, wherein x is 1.

3. The compound of claim 2, or a pharmaceutically acceptable salt thereof, wherein each of $R^{10a}$ and $R^{10b}$ is hydrogen; and $R^9$ is optionally substituted alkyl.

4. The compound of claim 1, or a pharmaceutically acceptable salt thereof, wherein m is 2 and the group:

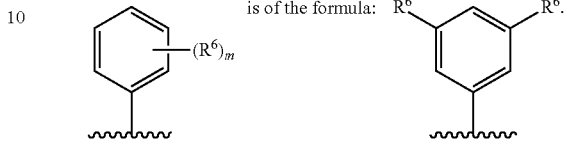 is of the formula: 

5. The compound of claim 1, or a pharmaceutically acceptable salt thereof, wherein m is 1 and the group:

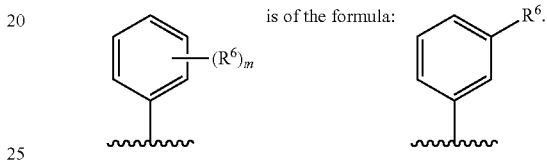 is of the formula: 

6. The compound of claim 1, or a pharmaceutically acceptable salt thereof, wherein $R^7$ is halogen, optionally substituted $c_{2-6}$ alkyl, substituted $C_1$ alkyl, optionally substituted alkenyl, or optionally substituted alkynyl.

7. The compound of claim 1, or a pharmaceutically acceptable salt thereof, wherein $R^7$ is halogen.

8. The compound of claim 1, or a pharmaceutically acceptable salt thereof, wherein $R^7$ is optionally substituted $C_{2-6}$ alkyl.

9. The compound of claim 1, or a pharmaceutically acceptable salt thereof, wherein $R^7$ is halogen, —OH, —SH, —$NH_2$, —CN, —$NO_2$, —$N_3$, —$SO_2H$, —$SO_3H$, substituted hydroxyl, substituted thiol, substituted amino, sulfonyl, sulfinyl, acyl, silyl, boronyl, optionally substituted $C_{2-6}$ alkyl, optionally substituted alkenyl, optionally substituted alkynyl, optionally substituted carbocyclyl, optionally substituted heterocyclyl, optionally substituted aryl, or optionally substituted heteroaryl.

10. The compound of claim 1, or a pharmaceutically acceptable salt thereof, wherein $R^7$ is substituted $C_1$ alkyl.

11. The compound of claim 1, or a pharmaceutically acceptable salt thereof, wherein $R^7$ is fluoro or chloro.

12. The compound of claim 1, or a pharmaceutically acceptable salt thereof, wherein $R^7$ is halogen, —OH, —SH, —$NH_2$, —CN, —$NO_2$, —$N_3$, —$SO_2H$, —$SO_3H$, substituted hydroxyl, substituted thiol, substituted amino, sulfonyl, sulfinyl, acyl, silyl, boronyl, optionally substituted alkenyl, optionally substituted alkynyl, optionally substituted carbocyclyl, optionally substituted heterocyclyl, optionally substituted aryl, or optionally substituted heteroaryl.

13. The compound of claim 1, or a pharmaceutically acceptable salt thereof, wherein $R^7$ is fluoro.

14. A pharmaceutical composition comprising a compound of claim 1, or pharmaceutically acceptable salt thereof, and a pharmaceutically acceptable excipient.

15. A method of preparing a compound of claim 1, the method comprising providing a compound of Formula (G):

(G)

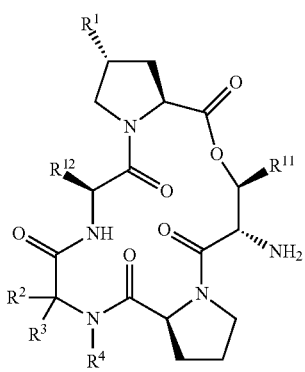

or salt thereof; and coupling the compound of Formula (G), or salt thereof, with a compound of Formula (H):

(H)

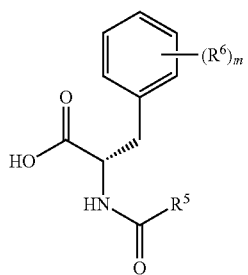

or salt thereof; to provide a compound of Formula (I):

(I)

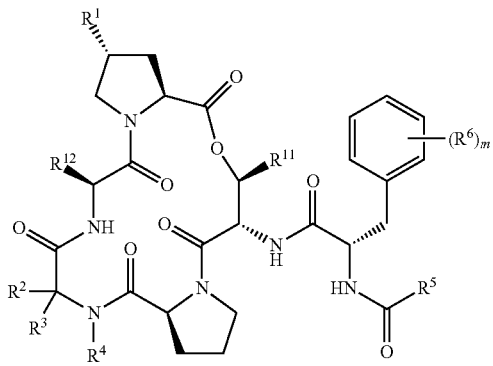

or pharmaceutically acceptable salt thereof;
wherein:

$R^2$ is hydrogen and the stereochemistry of the carbon attached to $R^2$ and $R^3$ is:

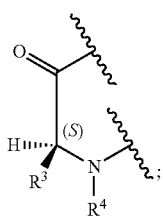

$R^1$ is hydrogen or —CH$_3$;

$R^3$ and $R^4$ are joined to form a substituted 6-membered heterocyclyl of formula:

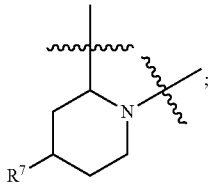

each instance of $R^7$ is independently halogen, —OH, —SH, —NH$_2$, —CN, —NO$_2$, —N$_3$, —SO$_2$H, —SO$_3$H, substituted hydroxyl, substituted thiol, substituted amino, sulfonyl, sulfinyl, acyl, silyl, boronyl, optionally substituted C$_{2-6}$ alkyl, substituted C$_1$ alkyl, optionally substituted alkenyl, optionally substituted alkynyl, optionally substituted carbocyclyl, optionally substituted heterocyclyl, optionally substituted aryl, or optionally substituted heteroaryl;

$R^5$ is:

(a)

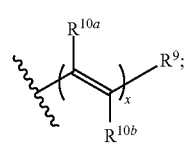

x is an integer between 1 and 10, inclusive;
$R^{10a}$ and $R^{10b}$ are independently hydrogen or optionally substituted alkyl;
$R^9$ is hydrogen, halogen, —CN, —NO$_2$, —N$_3$, substituted hydroxyl, substituted thiol, sulfonyl, sulfinyl, acyl, silyl, boronyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
each instance of $R^6$ is independently halogen, —OH, —SH, —NH$_2$, —CN, —NO$_2$, —N$_3$, —SO$_2$H, —SO$_3$H, substituted hydroxyl, substituted thiol, substituted amino, sulfonyl, sulfinyl, acyl, silyl, boronyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
m is 0 or an integer of between 1 and 5, inclusive;
$R^{11}$ is hydrogen; and
$R^{12}$ is —CH$_3$.

16. A method of treating a microbial infection in a subject comprising administering an effective amount of a compound of claim 1, or pharmaceutically acceptable salt thereof, to the subject.

17. The method of claim 16, wherein the microbial infection is a bacterial infection.

18. The method of claim 17, further comprising administering the compound, or pharmaceutically acceptable salt thereof, in combination with an antibiotic.

19. The method of claim 18, wherein the antibiotic is a ribosome-targeting antibiotic.

20. The method of claim 17, wherein the bacterial infection is resistant to other treatments.

21. The method of claim 17, wherein the bacterial infection is multi-drug tolerant or multi-drug resistant.

22. A method of treating microbial virulence comprising contacting an effective amount of a compound of claim 1, or pharmaceutically acceptable salt thereof, to a microorganism.

23. The method of claim 22, wherein the compound, or pharmaceutically acceptable salt thereof, blocks virulence factor production.

\* \* \* \* \*